US008299247B2

(12) United States Patent
Morishita

(10) Patent No.: US 8,299,247 B2
(45) Date of Patent: *Oct. 30, 2012

(54) MATERIAL FOR ORGANIC ELECTROLUMINESCENCE DEVICE AND ORGANIC ELECTROLUMINESCENCE DEVICE

(75) Inventor: Hironobu Morishita, Sodegaura (JP)

(73) Assignee: Idemitsu Kosan Co., Ltd., Tokyo (JP)

( * ) Notice: Subject to any disclaimer, the term of this patent is extended or adjusted under 35 U.S.C. 154(b) by 131 days.

This patent is subject to a terminal disclaimer.

(21) Appl. No.: 13/185,283

(22) Filed: Jul. 18, 2011

(65) Prior Publication Data

US 2011/0275814 A1    Nov. 10, 2011

Related U.S. Application Data

(63) Continuation of application No. 12/373,788, filed as application No. PCT/JP2008/062675 on Jul. 14, 2008.

(30) Foreign Application Priority Data

Jul. 18, 2007 (JP) ................................ 2007-186912

(51) Int. Cl.
C07D 487/04 (2006.01)
C07D 401/10 (2006.01)
C07C 255/35 (2006.01)
C07C 255/37 (2006.01)
C07C 255/51 (2006.01)
C07C 255/61 (2006.01)

(52) U.S. Cl. ........ 544/341; 428/690; 428/917; 313/504; 313/506; 564/270; 558/420; 558/427; 558/419; 546/264

(58) Field of Classification Search ........................ None
See application file for complete search history.

(56) References Cited

U.S. PATENT DOCUMENTS

| 6,423,429 | B2 | 7/2002 | Kido et al. |
| 6,597,012 | B2 | 7/2003 | Kido et al. |
| 2001/0046611 | A1 | 11/2001 | Kido et al. |
| 2003/0006411 | A1 | 1/2003 | Kido et al. |
| 2003/0180575 | A1 | 9/2003 | Ise |
| 2005/0255334 | A1 | 11/2005 | Kang et al. |
| 2006/0208221 | A1 | 9/2006 | Gerhard et al. |
| 2007/0160871 | A1 | 7/2007 | Morishita et al. |
| 2008/0160342 | A1 | 7/2008 | Meng et al. |
| 2009/0036643 | A1 | 2/2009 | Marks et al. |
| 2009/0315022 | A1 | 12/2009 | Morishita et al. |

FOREIGN PATENT DOCUMENTS

| JP | 2-146050 | 6/1990 |
| JP | 4-297076 | 10/1992 |
| JP | 11-251067 | 9/1999 |
| JP | 2000-196140 | 7/2000 |
| JP | 2001-297883 | 10/2001 |
| JP | 2003-31365 | 1/2003 |
| JP | 2004-514257 | 5/2004 |
| JP | 2005-215677 | 8/2005 |
| JP | 2006-49907 | 2/2006 |
| WO | WO 02/41414 A1 | 5/2002 |
| WO | WO 2004/093207 A2 | 10/2004 |
| WO | WO 2007/077766 A1 | 7/2007 |
| WO | WO 2009/011327 A1 | 1/2009 |

OTHER PUBLICATIONS

Journal of the American Chemical Society, (2008), vol. 130, No. 27, pp. 8580-8581.
Organic Letters, (2008), vol. 10, No. 7, pp. 1385-1388.
Wolfgang Frank, et al., "Electron-Rich and Electron-Poor Pentalene Derivatives", Tetrahedron Letters, vol. 28, No. 27, Pergamon Journal Ltd., 1987, pp. 3083-3086.

*Primary Examiner* — Dawn L Garrett
(74) *Attorney, Agent, or Firm* — Oblon, Spivak, McClelland, Maier & Neustadt, L.L.P.

(57) ABSTRACT

A material for an organic electroluminescence device including an indenofluorenedione derivative shown by the following formula (I):

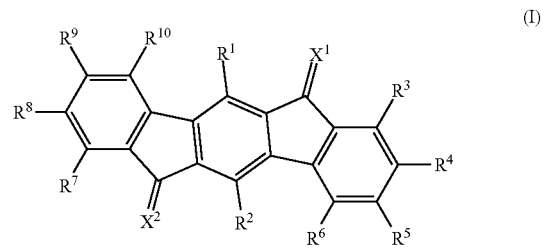

wherein $X^1$ and $X^2$, which may be the same or different, are any of specific divalent groups; $R^1$ to $R^{10}$, which may be the same or different, are a hydrogen atom, an alkyl group, an aryl group, a heterocycle, a halogen atom, a fluoroalkyl group, an alkoxy group, an aryloxy group or a cyano group; and $R^3$ to $R^6$ or $R^7$ to $R^{10}$ may be bonded to each other to form a ring.

9 Claims, 1 Drawing Sheet

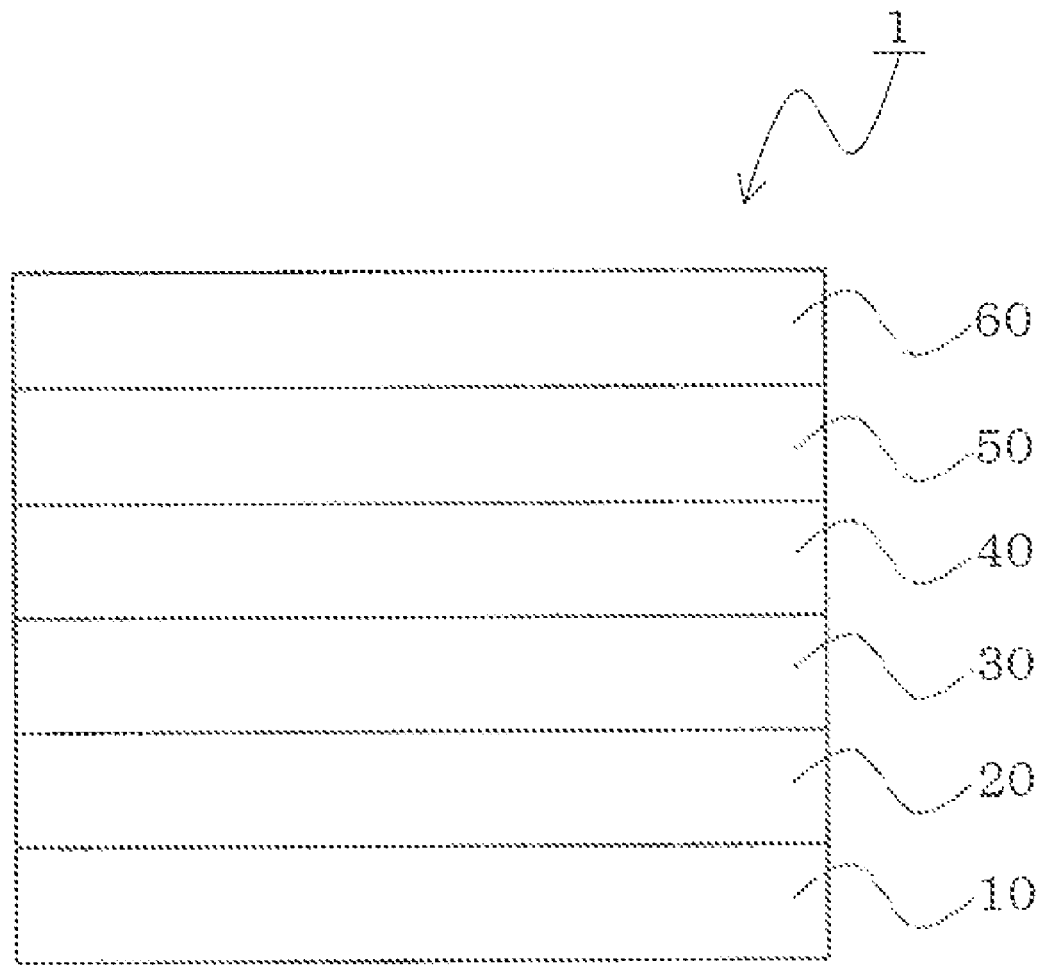

MATERIAL FOR ORGANIC ELECTROLUMINESCENCE DEVICE AND ORGANIC ELECTROLUMINESCENCE DEVICE

CROSS-REFERENCE TO RELATED APPLICATIONS

The present application is a continuation of U.S. patent application Ser. No. 12/373,788, filed on Jan. 14, 2009, which is a 35 U.S.C. §371 National Stage patentapplication of International patent application PCT/JP2008/062675, filed on Jul. 14, 2008, which claims priority to Japanese patent application JP 2007-186912, filed on Jul. 18, 2007.

TECHNICAL FIELD

The invention relates to a material for an organic electroluminescence device and an organic electroluminescence device.

BACKGROUND ART

An organic electroluminescence device (hereinafter the term "electroluminescence" is often abbreviated as "EL") is a self-emission device utilizing the principle that a fluorescent compound emits light by the recombination energy of holes injected from an anode and electrons injected from a cathode when an electric field is impressed.

Since C. W. Tang et al. of Eastman Kodak Co. reported a low-voltage driven organic EL device in the form of a stacked type device, studies on organic EL devices wherein organic materials are used as the constituting materials has actively been conducted.

The organic EL device reported by Tang et al. has a multilayer structure in which tris(8-hydroxyquinolinol)aluminum is used as an emitting layer and a triphenyldiamine derivative is used as a hole-transporting layer. The advantages of the multilayer structure include increased injection efficiency of holes to the emitting layer, increased generation efficiency of excitons generated by recombination by blocking electrons injected from the cathode, confinement of the generated excitons in the emitting layer, and so on.

As the multilayer structure of the organic EL device, a two-layered type of a hole-transporting (injecting) layer and an electron-transporting emitting layer, and a three-layered type of a hole-transporting (injecting) layer, an emitting layer and an electron-transporting (injecting) layer are widely known. In such multilayer structure devices, their device structures and fabrication methods have been contrived to increase recombination efficiency of injected holes and electrons.

Conventionally, aromatic diamine derivatives or aromatic condensed ring diamine derivatives have been known as hole-transporting materials used in the organic EL device.

However, in order to attain sufficient luminance in an organic EL device in which these aromatic diamine derivatives are used as a hole-transporting material, problems such as shortened device life and increased consumption power occur, since an applied voltage is required to be increased.

As the method to solve these problems, a method has been proposed in which an electron-acceptable compound such as Lewis acid is doped to the hole-injecting layer of the organic EL device (Patent Document Nos. 1 to 7, or the like). However, the electron-accepting compound used in Patent Document Nos. 1 to 4 suffers from a problem in which it becomes unstable when handling during the production process of the organic EL device or the device life is shortened due to insufficient stability such as heat resistance at the time of driving of the organic EL device.

In addition, tetrafluorotetracyanoquinodimethane (TC-NQF$_4$), which is an electron-accepting compound exemplified in Patent Documents 3 and 5 to 7 or the like, has a small molecular weight and is substituted with fluorine. Therefore, it has a high sublimation property, and may diffuse within an apparatus when fabricating an organic EL device by vacuum vapor deposition, thereby contaminating the apparatus or the device.

Patent Document 1: JP-A-2003-031365
Patent Document 2: JP-A-2001-297883
Patent Document 3: JP-A-2000-196140
Patent Document 4: JP-A-H11-251067
Patent Document 5: JP-A-H4-297076
Patent Document 6: JP-T-2004-514257
Patent Document 7: US2005/0255334A1

The invention has been made based on the above-mentioned problems, and an object thereof is to provide an electron-acceptable material which is suitable as a material constituting an organic EL device.

DISCLOSURE OF THE INVENTION

As a result of intensive studies, the inventors noted an indenofluorenedione skeleton. Even when the quinone site thereof is converted to a dicyanomethylene group or a cyanoimino group, these compounds suffer a small degree of steric hindrance, maintain their molecular planarity, are thermally stable, have a high sublimation temperature, and are capable of producing an organic EL device by vapor deposition. Furthermore, due to the presence of two quinone sites in the molecule, they have a high degree of electron acceptability. In addition, by incorporating a specific substituent, electron acceptability can be enhanced or crystallinity can be changed. For example, since an unsubstituted indenofluorenedione skeleton has a high degree of crystallinity, leak current may be generated due to crystallization when the thickness is increased. Therefore, in fabricating an organic EL device, crystallization can be suppressed by reducing the film thickness or by mixing with a hole-transporting material such as an amine-based compound. If this compound is used in a film with an increased thickness, or crystallization caused by the device fabrication conditions becomes problematic, a derivative of which the crystal condition has been changed by introducing into an indenofluorenedione skeleton a bulky substituent such as a phenyl group can be obtained.

The inventors have found that, if the indenofluorenedinone derivatives of the invention with the above-mentioned properties are used in an organic EL device, in particular, in a hole-transporting layer, a lowered driving voltage, prolonged device life and suppression of increases in voltage can be attained.

The invention can provide the following material for an organic EL device or the like.

1. A material for an organic electroluminescence device comprising an indenofluorenedione derivative shown by the following formula (I):

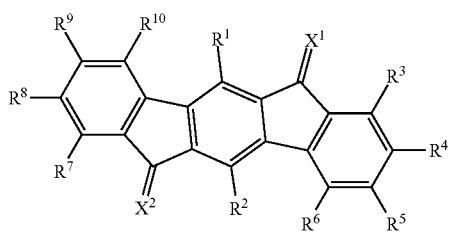

(I)

wherein $X^1$ and $X^2$, which may be the same or different, are any of divalent groups shown by the following formulas (a) to (e); $R^1$ to $R^{10}$, which may be the same or different, are a hydrogen atom, an alkyl group, an aryl group, a heterocycle, a halogen atom, a fluoroalkyl group, an alkoxy group, an aryloxy group or a cyano group; and $R^3$ to $R^6$ or $R^7$ to $R^{10}$ may be bonded to each other to form a ring;

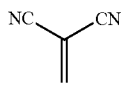 (a)

 (b)

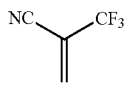 (c)

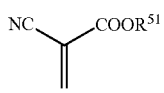 (d)

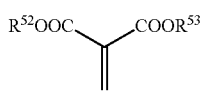 (e)

wherein $R^{51}$ to $R^{53}$, which may be the same or different, are a hydrogen atom, a fluoroalkyl group, an alkyl group, an aryl group or a heterocycle; and $R^{52}$ and $R^{53}$ may be bonded to each other to form a ring.

2. The material for an organic electroluminescence device according to 1, wherein the indenofluorendione derivative contains at least one of compounds shown by the following formulas (IIa), (IIb), (IIc) or (III):

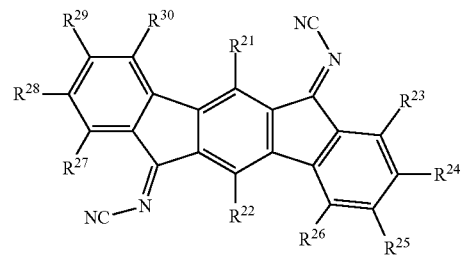

(IIa)

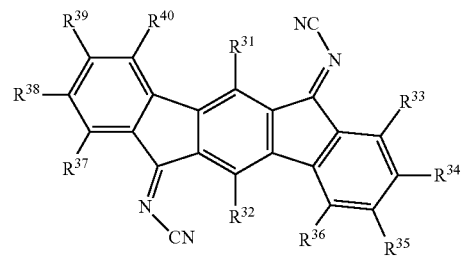

(IIb)

(IIc)

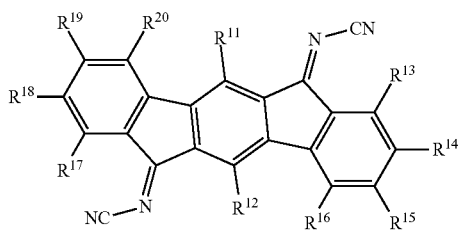

(III)

wherein $R^{11}$ to $R^{50}$, which may be the same or different, are a hydrogen atom, an alkyl group, an aryl group, a heterocycle, a fluorine atom, a fluoroalkyl group, an alkoxy group, an aryloxy group or a cyano group, provided that a case where all of $R^{11}$ to $R^{50}$ are a hydrogen atom is excluded; and $R^{11}$ to $R^{50}$ may be bonded to each other to form a ring.

3. The material for an organic electroluminescence device according to 1 or 2, which has a reduction potential in an acetonitrile solution of −1.0V or more (vsFc$^+$/Fc; wherein Fc indicates ferrocene).

4. The material for an organic electroluminescence device according to any one of 1 to 3, which is a hole-injecting material.

5. An organic electroluminescence device comprising organic thin film layers between an anode and a cathode; the organic thin film layers being a multilayer stack in which a hole-injecting layer, a hole-transporting layer, an emitting layer and an electron-transporting layer are stacked sequentially from the anode; and the hole-injecting layer containing the material for an organic electroluminescence device according to any one of 1 to 4.

6. The organic electroluminescence device according to 5, wherein the hole-injecting layer further contains a phenylenediamine compound shown by the following formula (IV):

(IV)

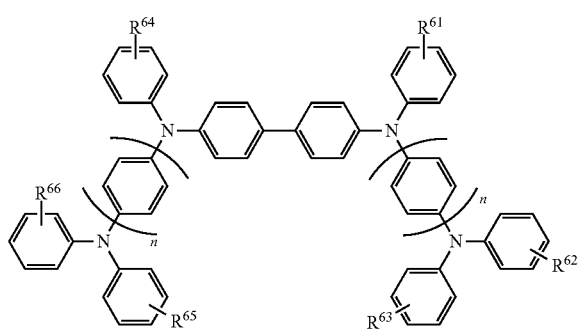

wherein $R^{61}$ to $R^{66}$, which may be the same or different, are a hydrogen atom, a halogen atom, a trifluoromethyl group, an alkyl group, an aryl group or a heterocycle, or may form a naphthalene skeleton, a carbazole skeleton or a fluorene skeleton with a phenyl group to which $R^{61}$ to $R^{66}$ bond; and n is 1 or 2.

7. An indenofluorenedione derivative which is shown by the following formula (I):

(I)

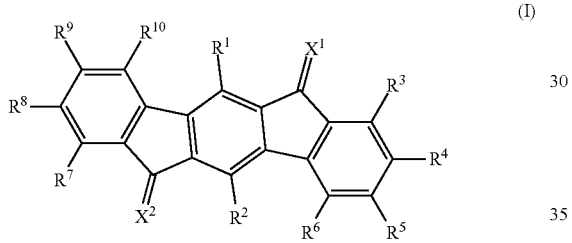

wherein $X^1$ and $X^2$, which may be the same or different, are any of divalent groups shown by the following formulas (a) to (e); and $R^1$ to $R^{10}$, which may be the same or different, are a hydrogen atom, an alkyl group, an aryl group, a heterocycle, a halogen atom, a fluoroalkyl group, an alkoxy group, an aryloxy group or a cyano group; and $R^3$ to $R^6$ or $R^7$ to $R^{10}$ may be bonded to each other to form a ring;

(a)
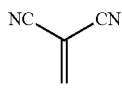

(b)
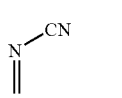

(c)
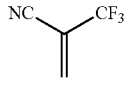

(d)
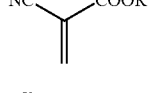

(e)
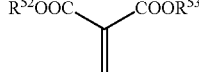

wherein $R^{51}$ to $R^{53}$, which may be the same or different, are a hydrogen atom, a fluoroalkyl group, an alkyl group, an aryl group or a heterocyclic group; and $R^{52}$ and $R^{53}$ may be bonded to each other to form a ring.

8. The indenofluorenedione derivative according to 7, which is any of compounds shown by the following formulas (IIa), (IIb), (IIc) or (III):

(IIa)
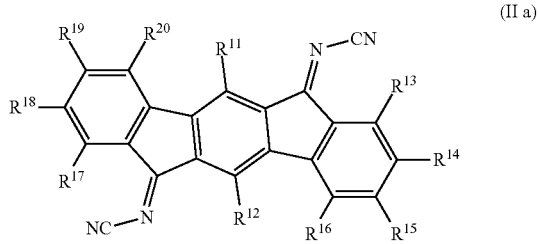

(IIb)
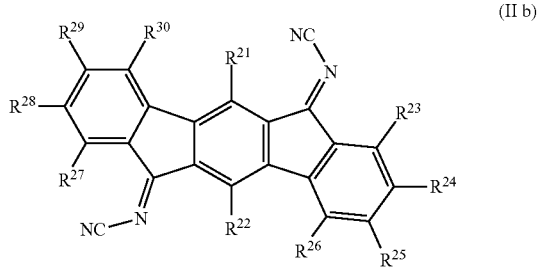

(IIc)
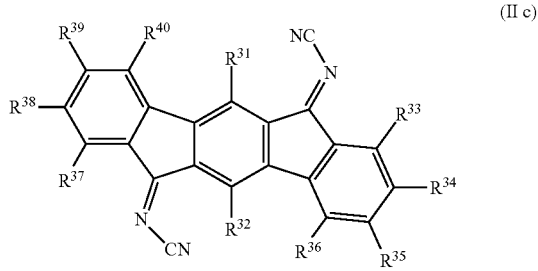

(III)
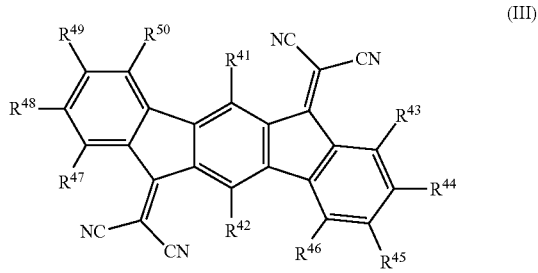

wherein $R^{11}$ to $R^{50}$, which may be the same or different, are a hydrogen atom, an alkyl group, an aryl group, a heterocycle, a fluorine atom, a fluoroalkyl group, an alkoxy group, an aryloxy group or a cyano group, provided that a case where all of $R^{11}$ to $R^{50}$ are a hydrogen atom is excluded; and $R^{11}$ to $R^{50}$ may be bonded to each other to form a ring.

According to the invention, it is possible to provide a novel material for an organic EL device. Also, it is possible to provide an organic EL device which can be driven at a low driving voltage and has a long life.

BRIEF DESCRIPTION OF THE INVENTION

FIG. 1 is a schematic cross-sectional view showing one embodiment of the organic EL device of the invention.

BEST MODE FOR CARRYING OUT THE INVENTION

At first, the material for an organic EL device of the invention is described.

The material for an organic EL device comprises an indenofluorenedione derivative shown by the following formula (I):

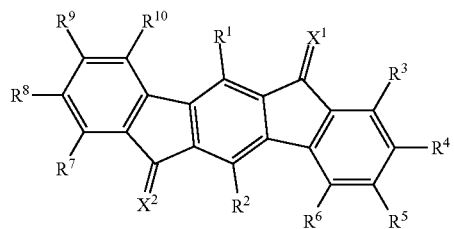

wherein $X^1$ and $X^2$, which may be the same or different, are any one of divalent groups shown by the following formulas (a) to (e); and $R^1$ to $R^{10}$, which may be the same or different, are a hydrogen atom, an alkyl group, an aryl group, a heterocycle, a halogen atom, a fluoroalkyl group, an alkoxy group, an aryloxy group or a cyano group; and $R^3$ to $R^6$ or $R^7$ to $R^{10}$ may be bonded to each other to form a ring;

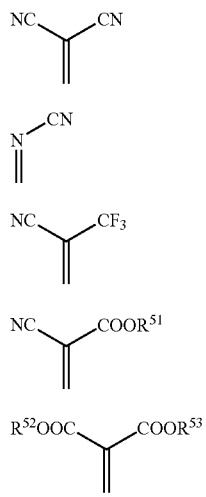

wherein $R^{51}$ to $R^{53}$, which may be the same or different, are independently a hydrogen atom, a fluoroalkyl group, an alkyl group, an aryl group or a heterocyclic group; and $R^{52}$ and $R^{53}$ may be bonded to each other to form a ring.

As examples of the halogen atom shown by $R^1$ to $R^{10}$, a fluorine atom, a chlorine atom, a bromine atom or an iodine atom can be given.

Examples of the alkyl group include a methyl group, an ethyl group, an n-propyl group, an iso-propyl group, an n-butyl group, an iso-butyl group, a tert-butyl group, a cyclopentyl group and a cyclohexyl group.

Examples of the aryl group include a phenyl group, a biphenyl group, a naphthyl group, a fluorophenyl group and a trifluoromethylphenyl group.

Examples of the fluoroalkyl group include a trifluoromethyl group, a pentafluoroethyl group, a perfluorocyclohexyl group and a perfluoroadamantyl group.

Examples of the alkoxy group include a methoxy group, an ethoxy group and a trifluoromethoxy group.

Examples of the aryloxy group include a benzyloxy group, a pentafluorobenzyloxy group and a 4-trifluoromethylbenzyloxy group.

Examples of the heterocycle include pyridine, pyrazine, furane, imidazole, benzimidazole and thiophene.

Each of the alkyl group, aryl group, fluoroalkyl group or heterocycle shown by $R^1$ to $R^{10}$ may be further substituted by a substituent. These substituents may be the same as the halogen atom, the cyano group, the alkyl group, the aryl group, the fluoroalkyl group or the heterocycle as mentioned above. The same can be applied to the fluoroalkyl group, the alkyl group, the aryl group or the heterocyclic group shown by $R^{51}$ to $R^{53}$.

$R^3$ to $R^6$ or $R^7$ to $R^{10}$ may be bonded to each other to form a ring. Examples of the ring include a benzene ring, a naphthalene ring, a pyrazine ring, a pyridine ring and a furan ring.

Similarly, $R^{52}$ and $R^{53}$ may be bonded to each other to form a ring.

Due to the structure shown by the formula (I), stability such as the heat resistance and sublimation property or electron acceptability can be enhanced. This compound has electron acceptability and improved heat resistance. Also, due to its capability of being purified through sublimation, the purity thereof can be enhanced. By using the compound in an organic EL device, driving voltage can be reduced and the life can be prolonged. Furthermore, since the compound does not scatter inside the film-forming apparatus during the production of a device, there is no fear that the film-forming apparatus or the organic EL device may be contaminated by the compound.

For the above-mentioned reason, the compound is suitable as the material for an organic EL device, in particular, as the hole-injecting material.

It is preferred that the compound shown by the above formula (I) be any compounds shown by the following formulas (IIa), (IIb), (IIc) or (III).

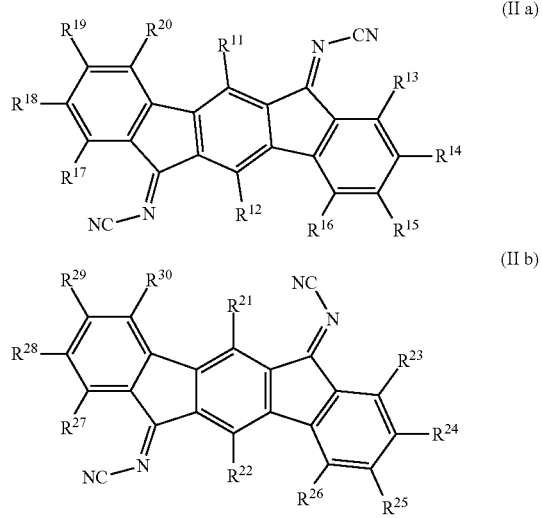

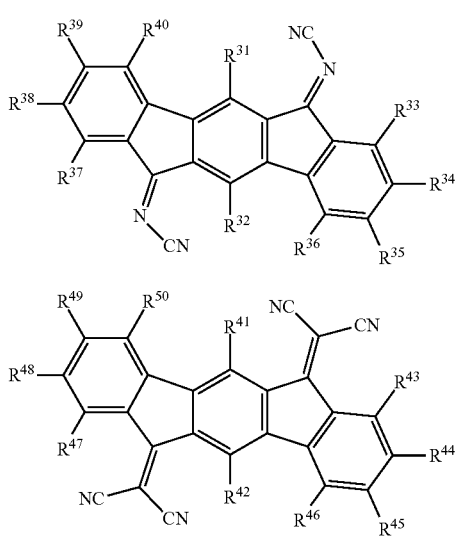

wherein $R^{11}$ to $R^{50}$, which may be the same or different, are independently a hydrogen atom, an alkyl group, an aryl group, a heterocycle, a fluorine atom, a fluoroalkyl group, an alkoxy group, an aryloxy group or a cyano group, provided that a case where all of $R^{11}$ to $R^{50}$ are a hydrogen atom is excluded; and $R^{11}$ to $R^{50}$ may be bonded to each other to form a ring.

Examples of the alkyl group, the aryl group, the fluoroalkyl group, the alkoxy group, the aryloxy group or the heterocycle shown by $R^{11}$ to $R^{50}$ are the same as those exemplified above for $R^1$ to $R^{10}$.

Depending on the type of the substituent of $X^1$ and $X^2$ in the formula (I), isomers are present. For example, in the case of the compound shown by the formula (IIa), the isomers (IIb) (IIc) are present which have different bonding positions of the two cyano groups of the cyanoimine groups. The material of the invention is not restricted to a specific isomer. It may be a compound having no isomers, a syn-type isomer, an anti-type isomer, or a mixture thereof.

It is preferred that the material for an organic EL device of the invention have a reduction potential in an acetonitrile solution of $-1.0V$ ($vsFc^+/Fc$) or more, particularly preferably $-0.8V$ ($vsFc^+/Fc$) or more. Here, Fc indicates ferrocene. Electron acceptability is further increased by using a compound with a reduction potential of $-1.0V$ or more.

An increase in electron-acceptability has the following merits. Electron transfer with an anode formed of ITO or a material having a work function smaller than that of ITO is facilitated. In addition, since the HOMO level of a hole-transporting material and the LUMO level of an electron-transporting material get close to each other, holes can be injected more easily.

Specific examples of the material for an organic EL device of the invention will be shown below.

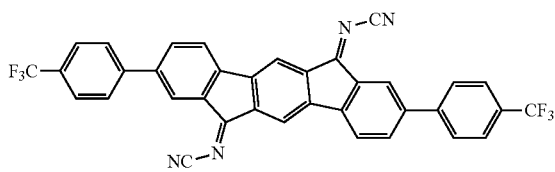

(A-1)

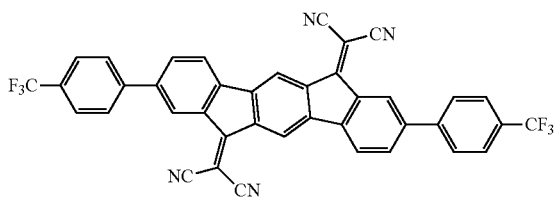

(A-2)

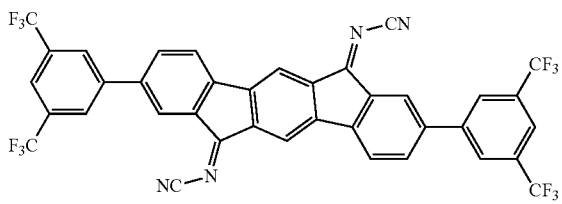

(A-3)

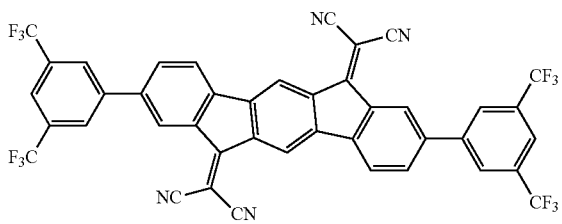

(A-4)

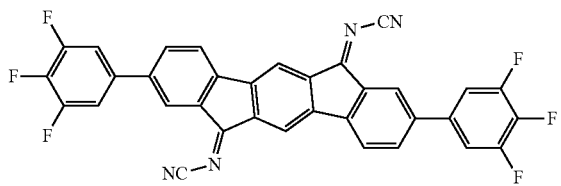

(A-5)

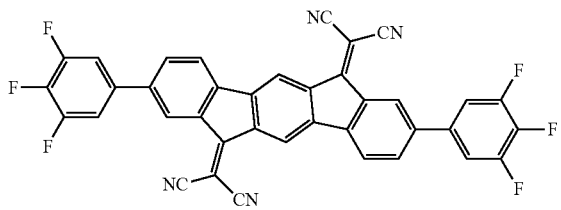

(A-6)

-continued
(A-7)
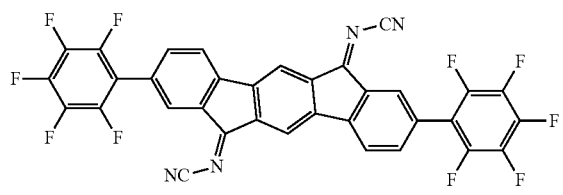
(A-8)
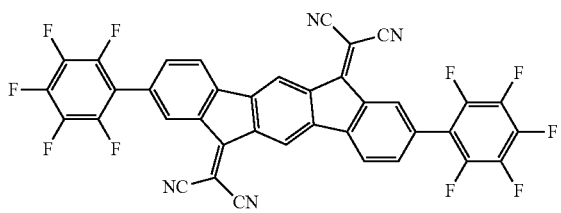
(A-9)
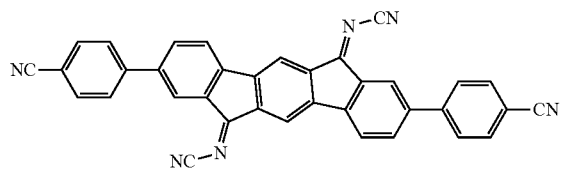
(A-10)
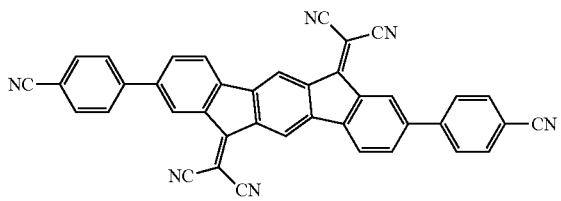
(A-11)
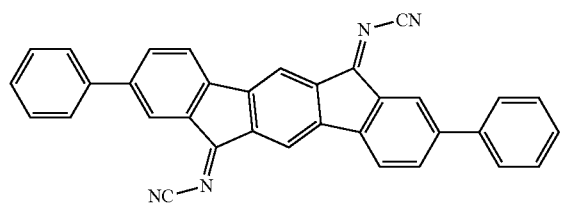
(A-12)
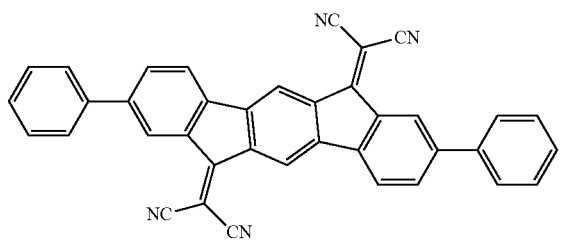
(A-13)
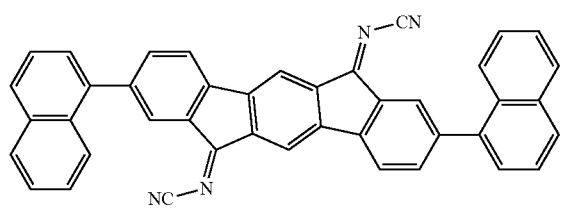
(A-14)
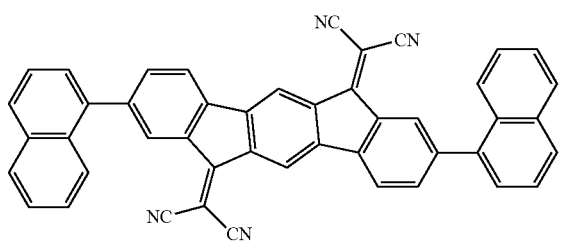
(A-15)
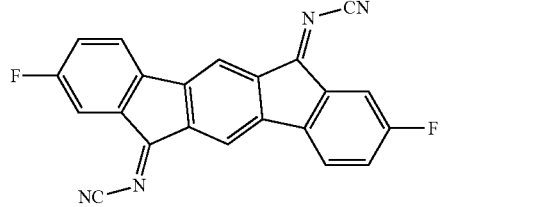
(A-16)
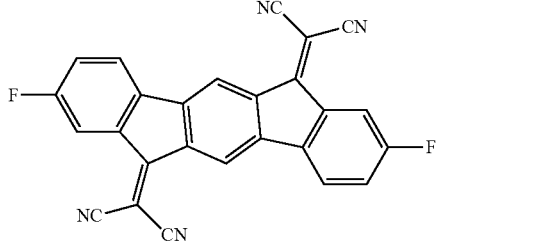
(A-17)
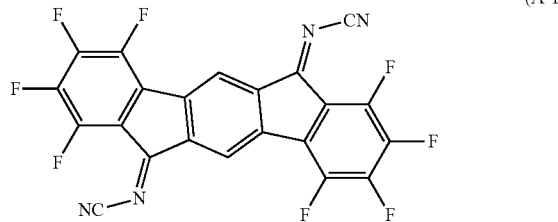
(A-18)
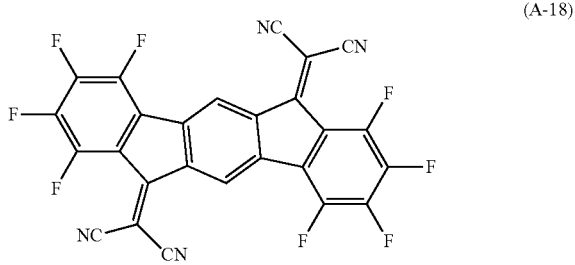

-continued
(A-19) 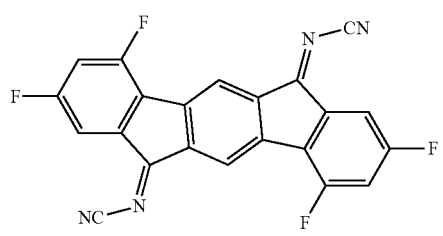
(A-20) 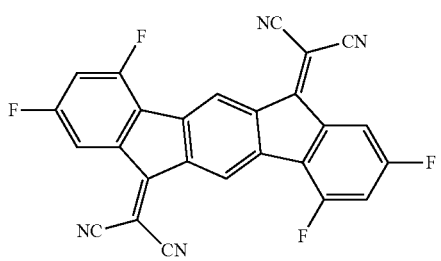
(A-21) 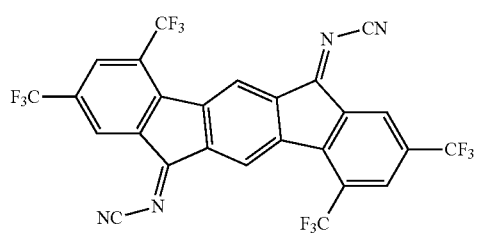
(A-22) 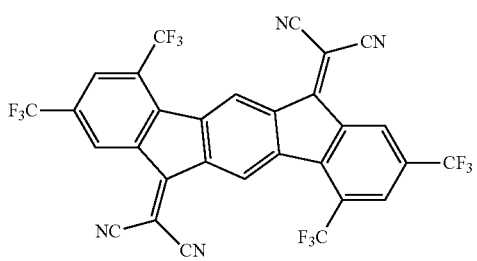
(A-23) 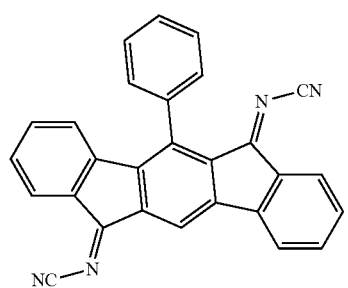
(A-24) 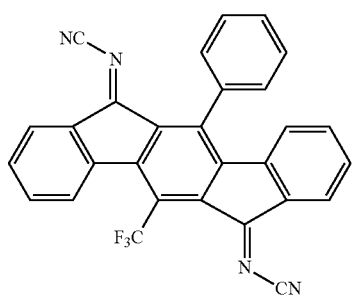
(A-25) 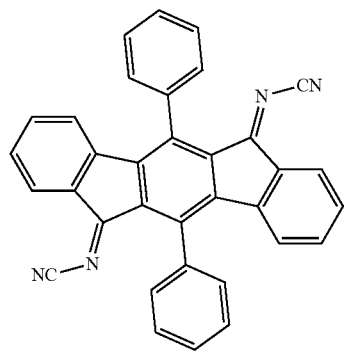
(A-26) 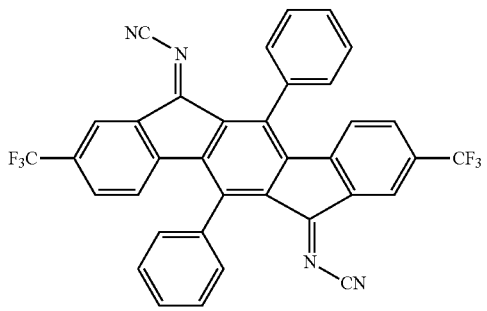
(A-27) 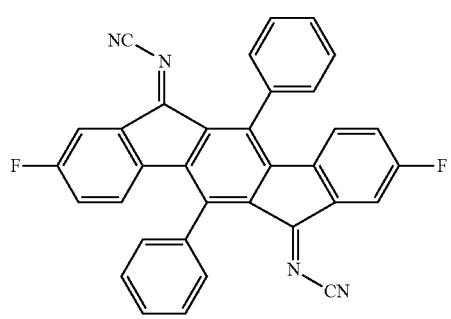
(A-28) 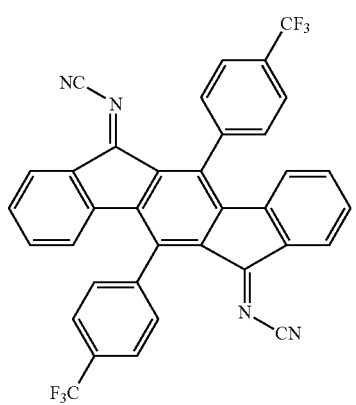

-continued
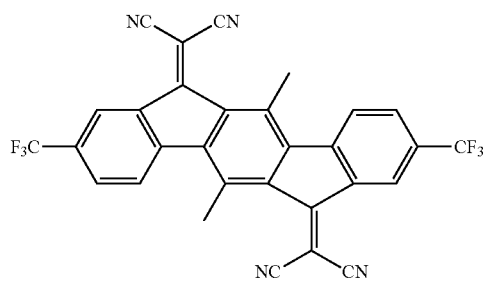
(A-29)
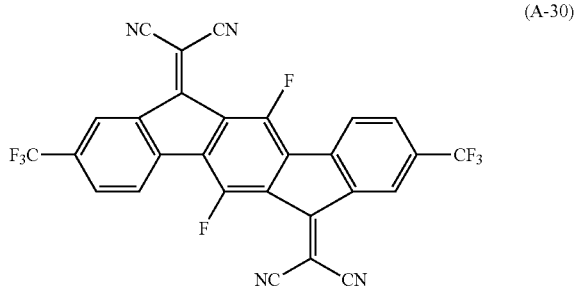
(A-30)
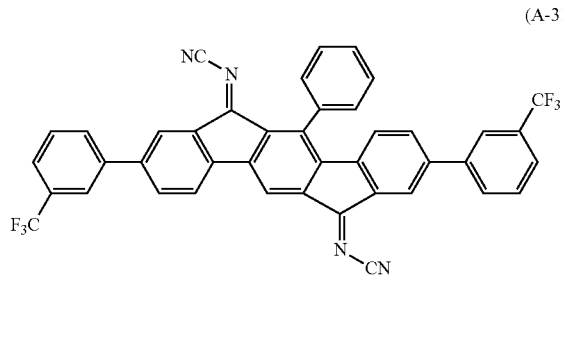
(A-31)
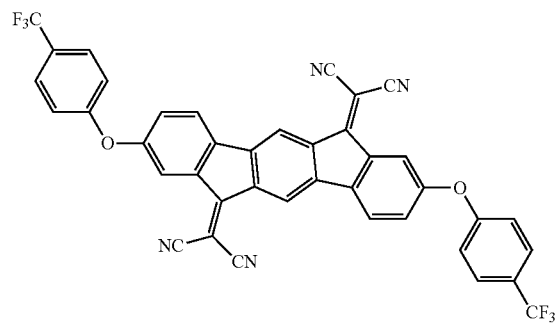
(A-32)
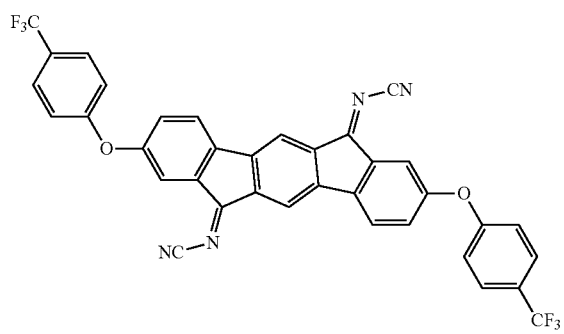
(A-33)
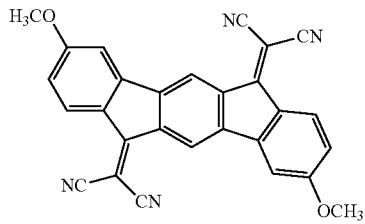
(A-34)
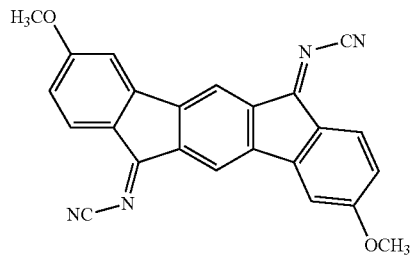
(A-35)
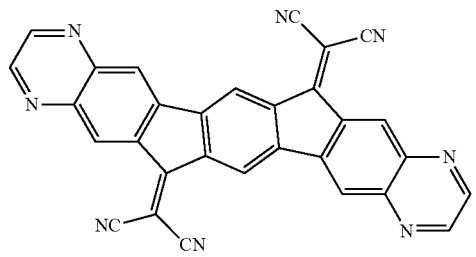
(A-36)
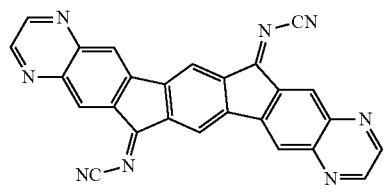
(A-37)
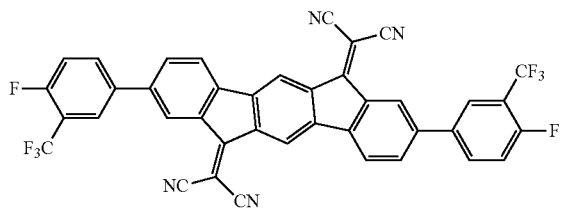
(A-38)

-continued
(A-39)
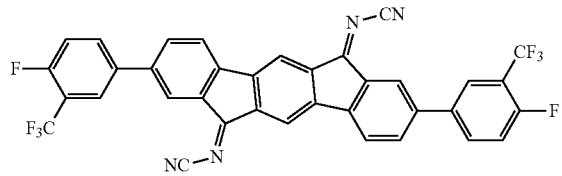
(A-40)
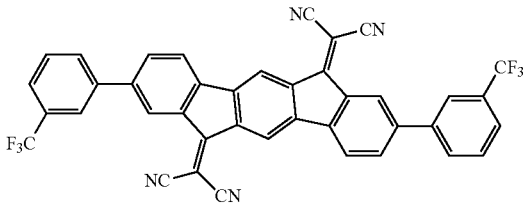
(A-41)
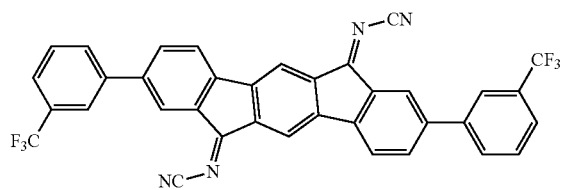
(A-42)
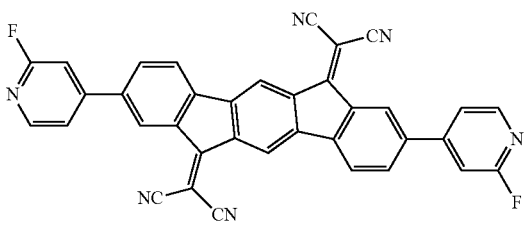
(A-43)
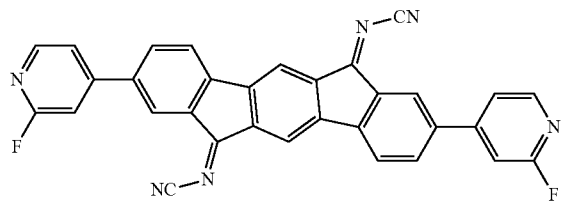
(A-44)
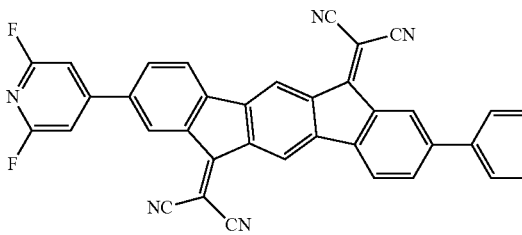
(A-45)
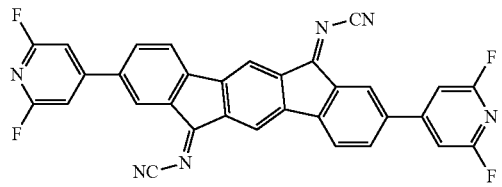
(A-46)
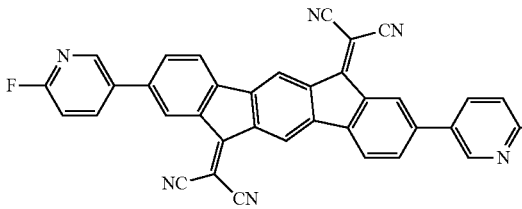
(A-47)
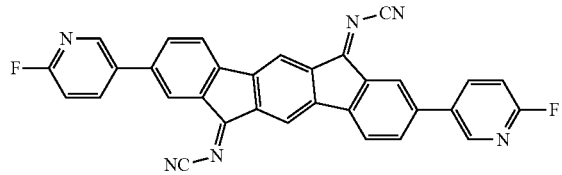
(A-48)
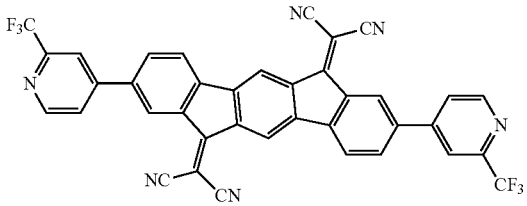
(A-49)
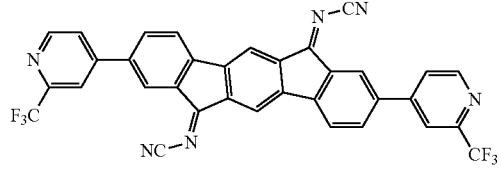
(A-50)
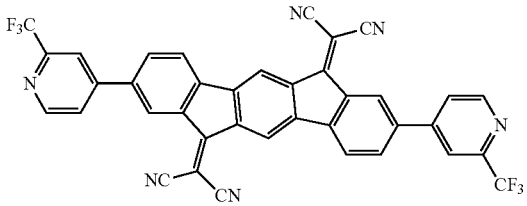
(A-51)
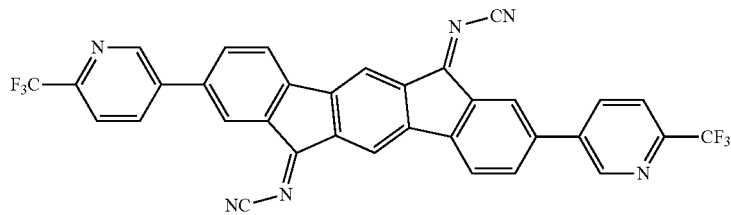

-continued
(A-52)
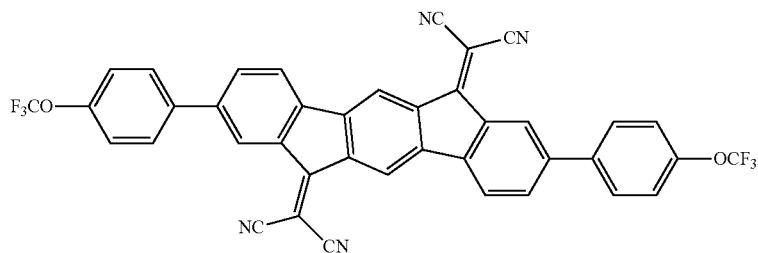
(A-53)
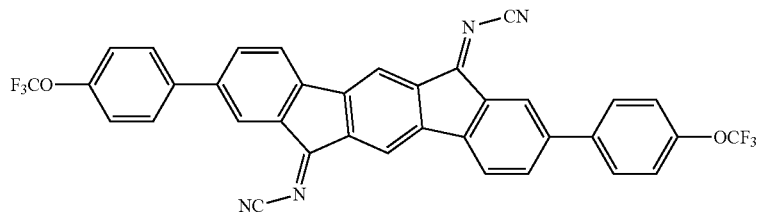
(A-54)
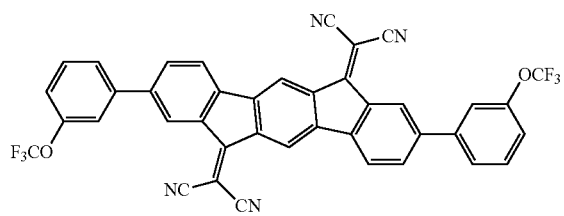
(A-55)
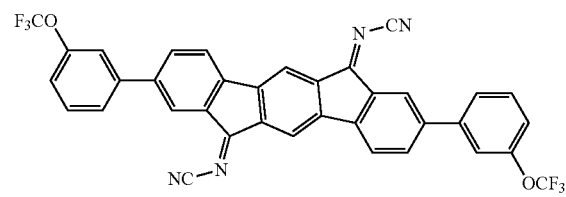
(A-56)
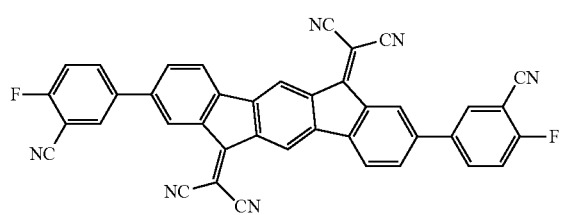
(A-57)
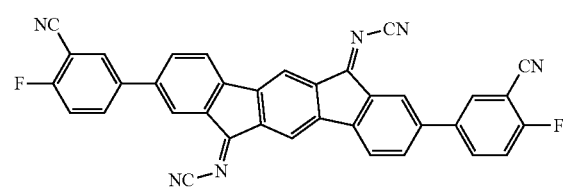
(A-58)
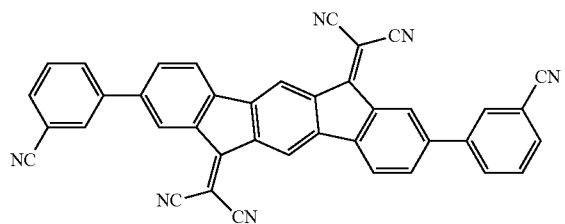
(A-59)
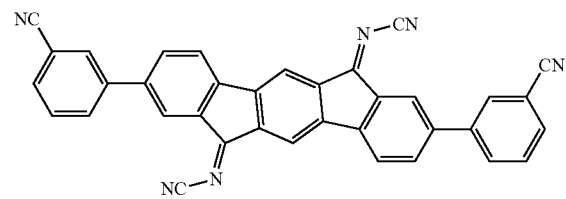
(A-60)
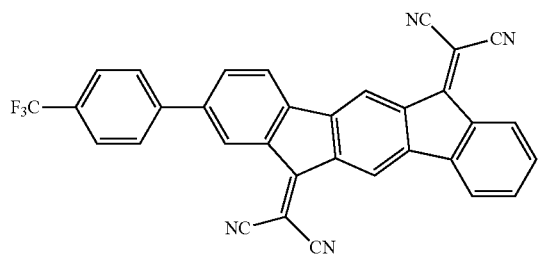
(A-61)
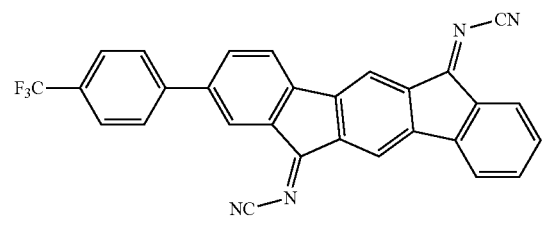

-continued
(A-62)
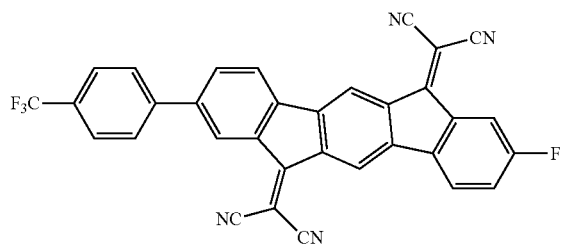
(A-63)
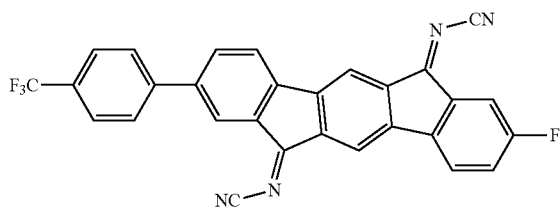
(A-64)
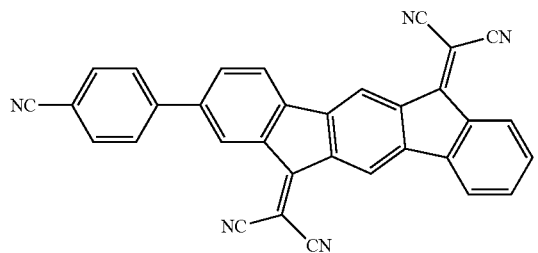
(A-65)
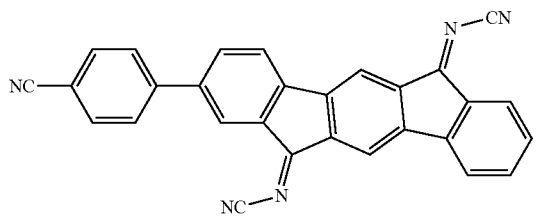
(A-66)
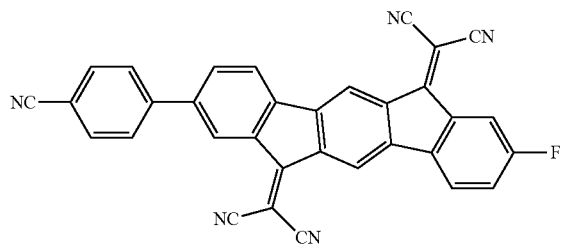
(A-67)
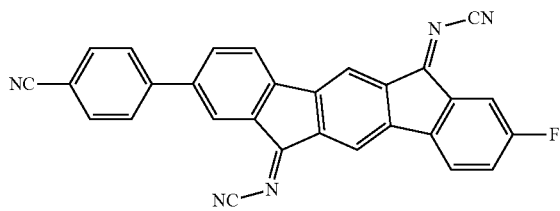
(A-68)
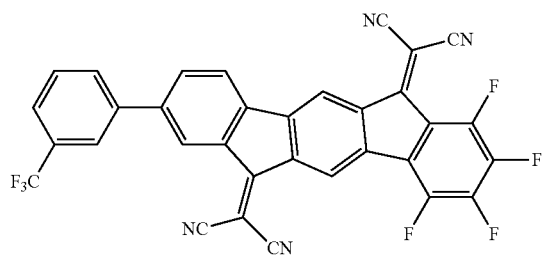
(A-69)
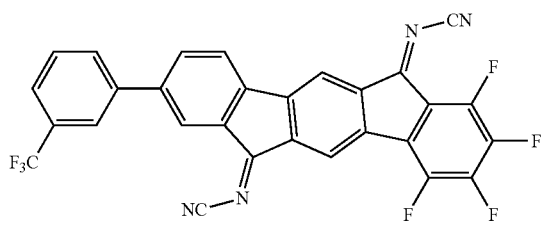
(A-70)
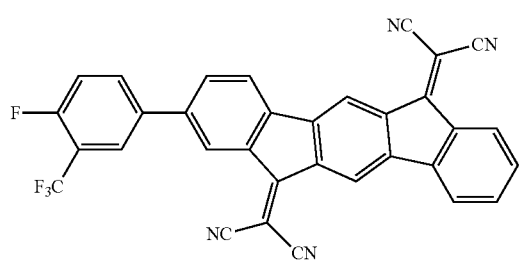
(A-71)
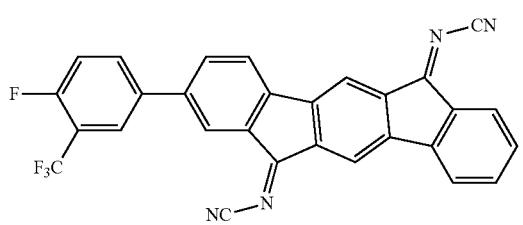
(A-72)
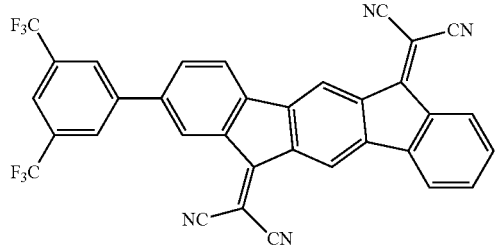

-continued
(A-74)
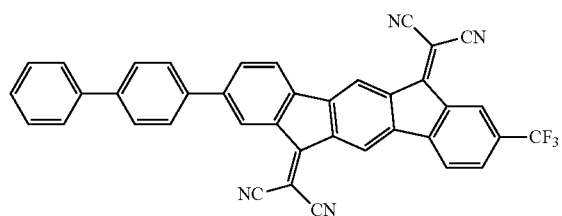
(A-75)
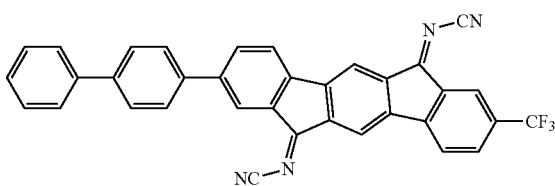
(A-76)
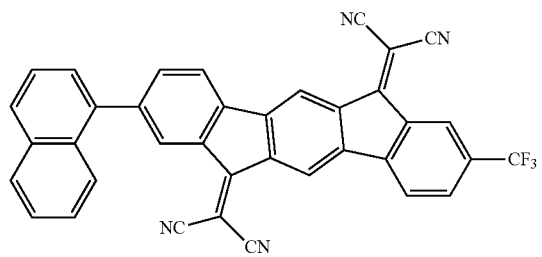
(A-77)
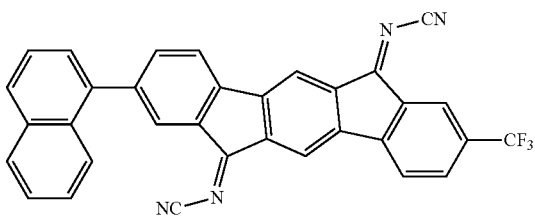
(A-78)
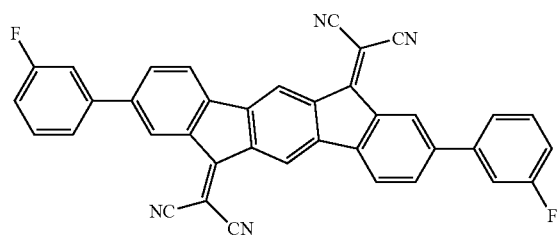
(A-79)
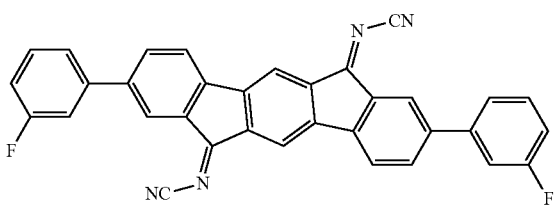
(A-80)
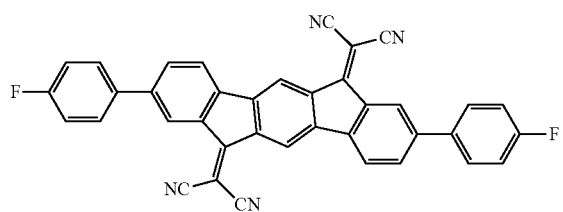
(A-81)
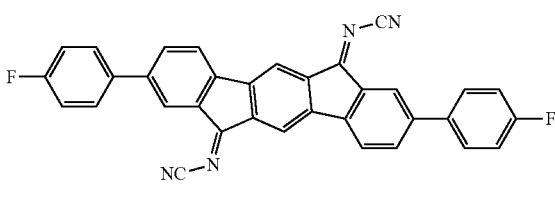
(A-82)
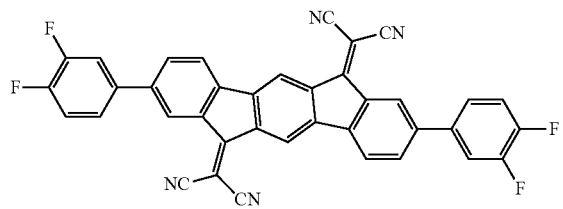
(A-83)
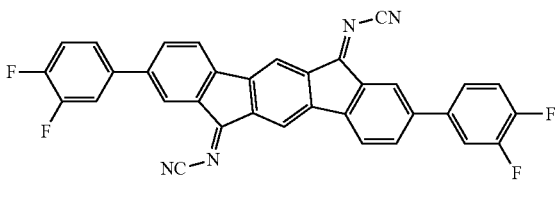
(A-84)
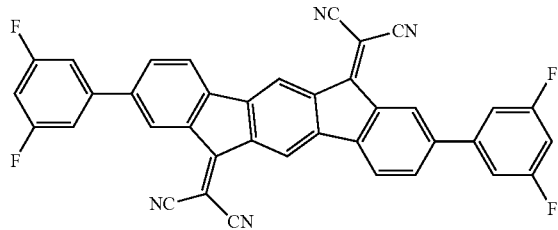
(A-85)
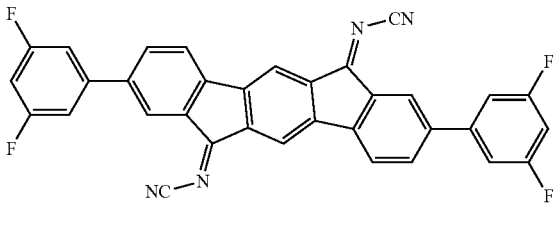

-continued

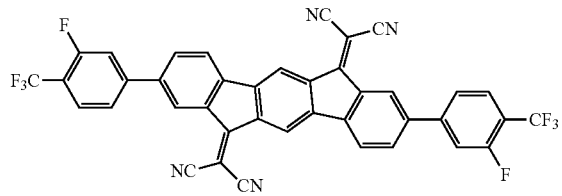

(A-86)

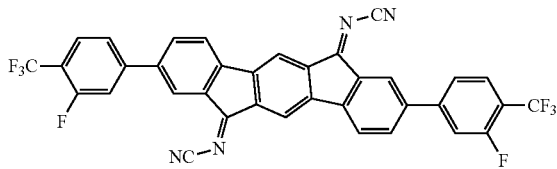

(A-87)

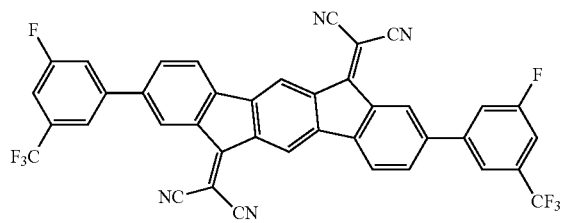

(A-88)

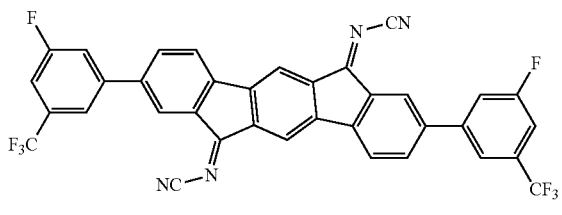

(A-89)

The indenofluorenedione derivative of the invention can be obtained by the synthesis of the following scheme 1 from an indenofluorenedione derivative which has been synthesized by the synthesis method described, for example, in Organic Letters Vol. 4, page 2157 (2002) or in Organic Letters Vol. 7, page 4229 (2005). For the details such as synthesis conditions, reference can be made to Liebigs Ann. Chem. (1986), page 142. By subjecting crystals obtained by these reactions to purification by sublimation to decrease the amount of impurities, the crystals can attain excellent performance in respect of device life or the like when used as the material for an organic EL device.

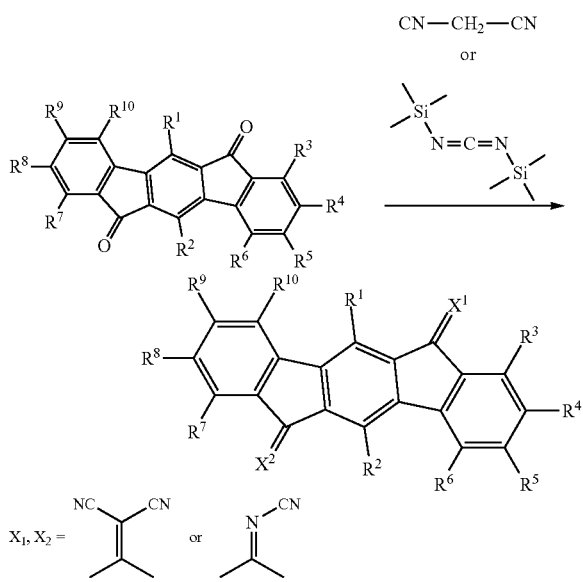

$R^1$ to $R^{10}$ are the same as in the above formula (I).

Next, the organic EL device of the invention is described.

The organic EL device of the invention has organic thin film layers between the anode and the cathode. Organic thin film layers include a hole-injection layer, a hole-transporting layer, an emitting layer and an electron-transporting layer in this order, and the hole-injecting layer contains the material for an organic EL device of the invention.

FIG. 1 is a schematic cross-sectional view showing one embodiment of the organic EL device of the invention.

In an organic EL device 1, an anode 10, a hole-injecting layer 20, a hole-transporting layer 30, an emitting layer 40, an electron-transporting layer 50 and a cathode 60 are sequentially stacked on a substrate (not shown). In this device, organic thin film layers are of a multilayer structure comprising the hole-injecting layer 20, the hole-transporting layer 30, the emitting layer 40 and the electron-transporting layer 50. In the invention, the hole-injecting layer 20 contains the material for an organic EL device of the invention. As a result, the organic EL device can be driven at a lower voltage and has a prolonged device life. In addition, a voltage increase can be suppressed.

Other organic layers than the hole-injecting layer may contain the material for an organic EL device of the invention. In this case, the material for an organic EL device of the invention may be used in mixture with materials constituting each layer, which will be mentioned layer.

The content of the material for an organic EL device of the invention in the hole-injecting layer is preferably 1 to 100 mole %.

In the organic EL device of the invention, it is preferred that the hole-injecting layer contain a phenylenediamine compound shown by the following formula (IV), in addition to the compounds shown by (I), (IIa), (IIb), (IIc) or (III) as mentioned above.

(IV)

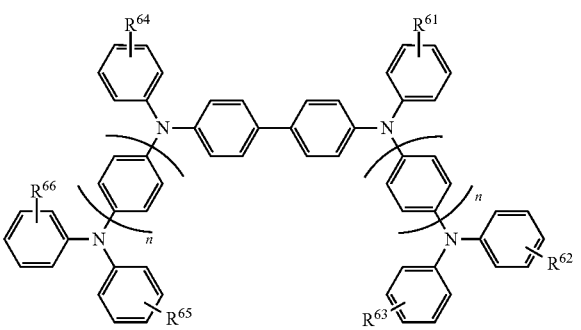

wherein $R^{61}$ to $R^{66}$, which may be the same or different, are independently a hydrogen atom, a halogen atom, a trifluoromethyl group, an alkyl group, an aryl group or a heterocycle, or may form a naphthalene skeleton, a carbazole skeleton or a fluorene skeleton with a phenyl group to which $R^{61}$ to $R^{66}$ bond; and n is 1 or 2.

When the phenylenediamine compound is contained, uniformity of a film, heat resistance or carrier-injecting properties may be improved as compared with the case where the compound of the invention is used singly.

In the formula (IV), as the halogen atom shown by $R^{61}$ to $R^{66}$, a fluorine atom is preferable.

As the alkyl group shown by $R^{61}$ to $R^{66}$, a methyl group, an isopropyl group, a tert-butyl group and a cyclohexyl group are preferable, for example.

As the aryl group shown by $R^{61}$ to $R^{66}$, a phenyl group, a naphthyl group and a fluorenyl group are preferable, for example. They may be substituted with a methyl group or the like.

As the heterocycle shown by $R^{61}$ to $R^{66}$, a pyridine ring and a pyrazine ring are preferable, for example.

$R^{61}$ to $R^{66}$ may form a naphthalene skeleton, a carbazole skeleton or a fluorene skeleton with a bonded phenyl group. They may be substituted with a methyl group or the like.

The content of the compound shown by the formula (IV) in the hole-injecting layer is preferably 0.1 to 98 mole %.

The mixing ratio of the compound shown by the above-mentioned formula (I), (IIa), (IIb), (IIc) or (III) and the phenylenediamine compound shown by the formula (IV) may be selected appropriately according to the material of the anode.

Preferred examples of the compound (IV) are given below.

(C-1)

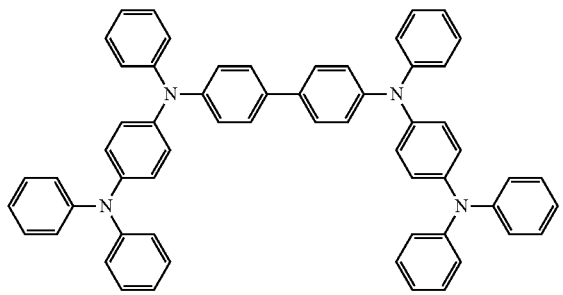

(C-2)

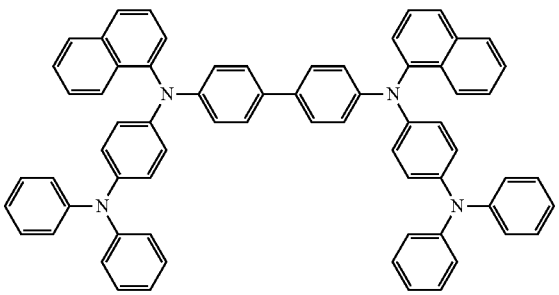

(C-3)

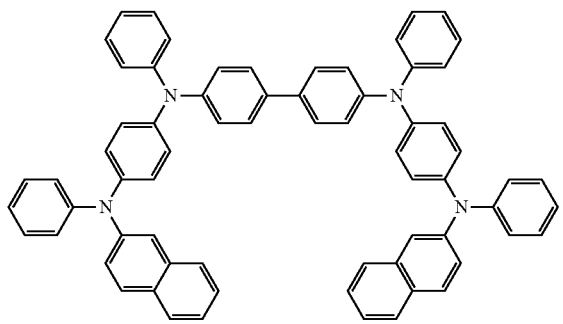

(C-4)

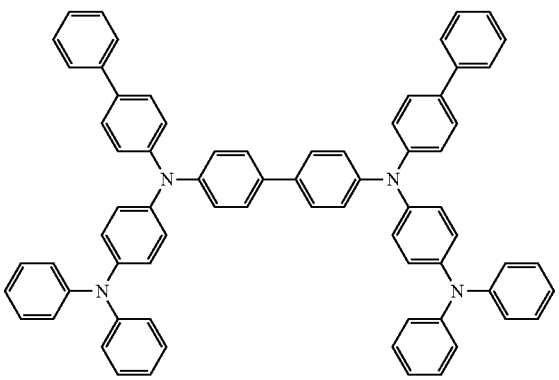

(C-5)

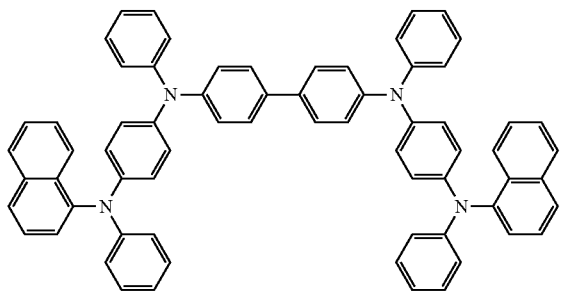

(C-6)

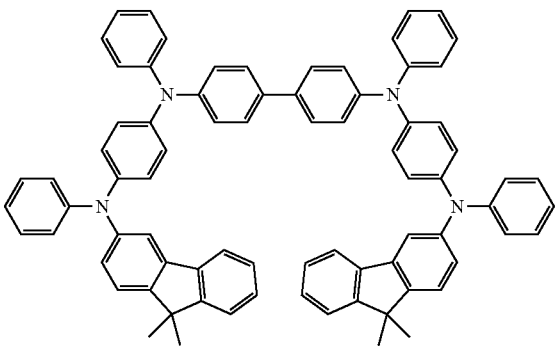

-continued
(C-7)
(C-8)
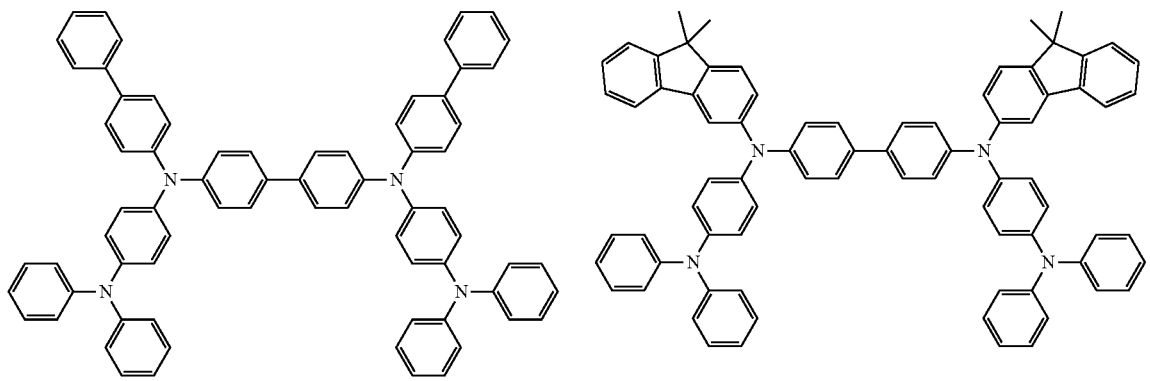
(C-9)
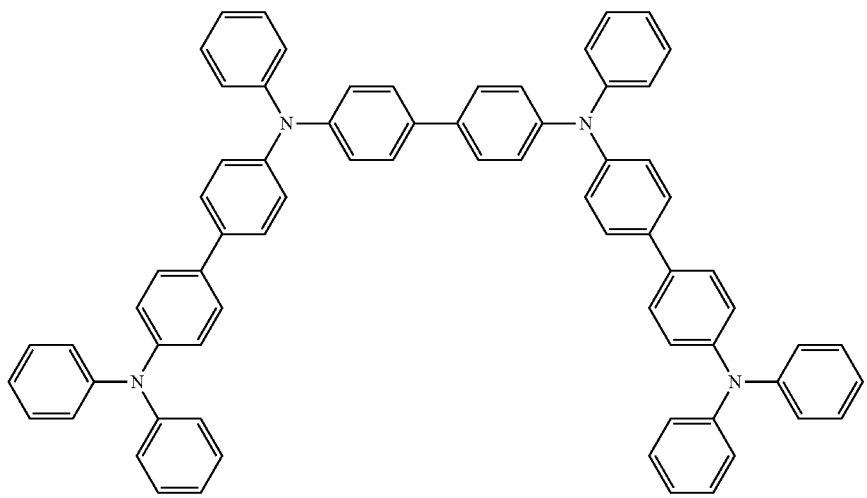
(C-10)
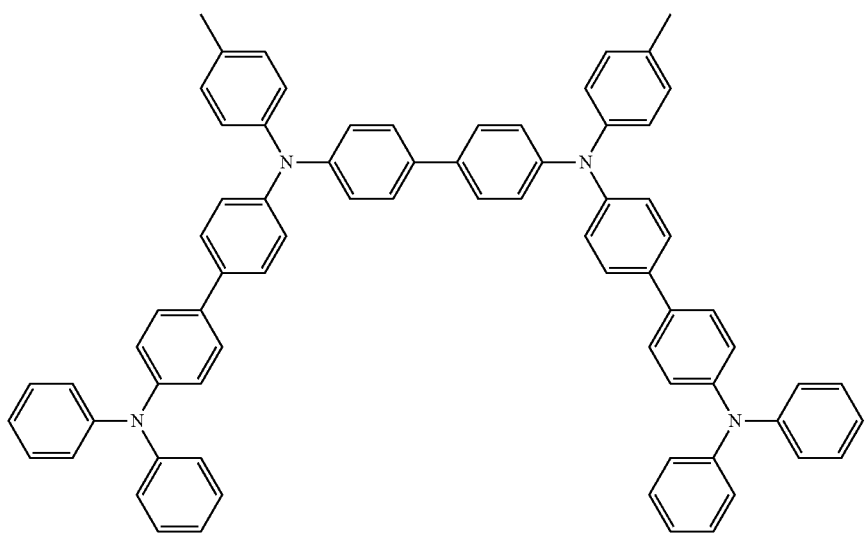

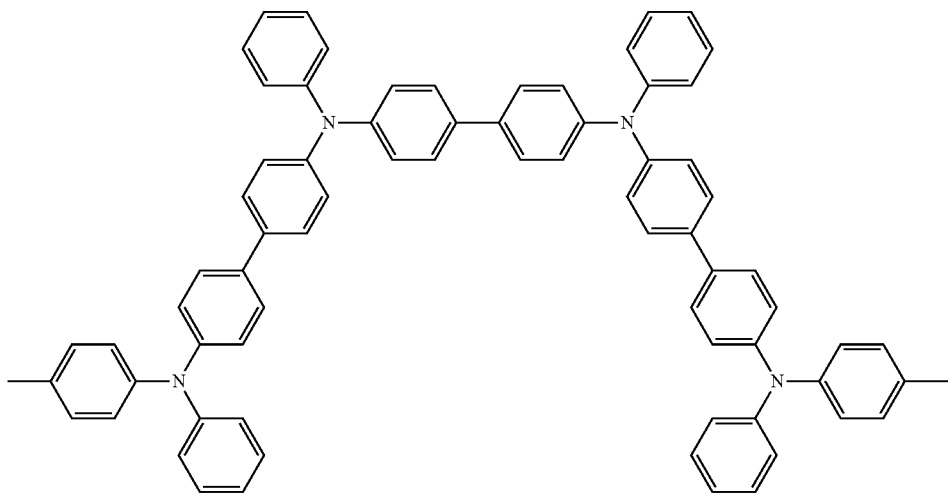
(C-11)

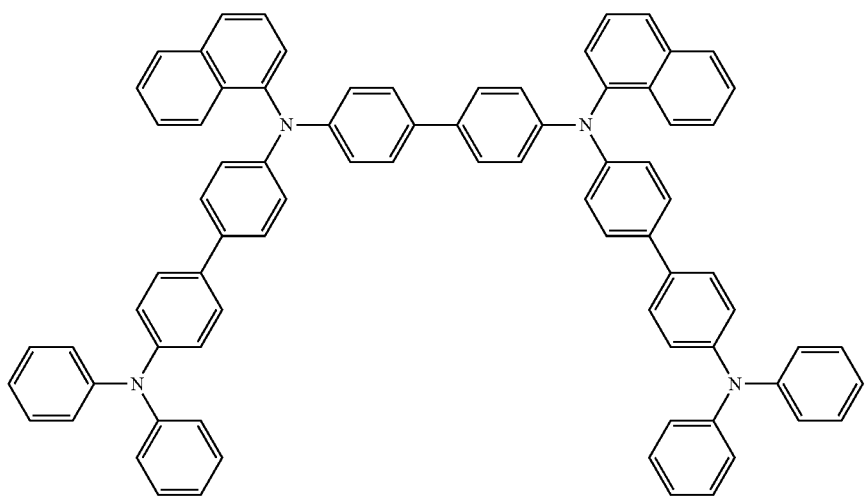
(C-12)

The material for the organic EL device of the invention can be used for a device with a configuration other than that in the above-mentioned embodiment. For example, the material for the organic EL device of the invention may be used as a material for each organic layer such as an emitting layer constituting a device with the following configurations (1) to (15).
(1) Anode/emitting layer/cathode
(2) Anode/hole-transporting layer/emitting layer/cathode
(3) Anode/emitting layer/electron-transporting layer/cathode
(4) Anode/hole-transporting layer/emitting layer/electron-transporting layer/cathode
(5) Anode/hole-transporting layer/emitting layer/adhesion-improving layer/cathode
(6) Anode/hole-injecting layer/hole-transporting layer/emitting layer/electron-transporting layer/cathode (FIG. 1)
(7) Anode/hole-transporting layer/emitting layer/electron-transporting layer/electron-injecting layer/cathode
(8) Anode/hole-injecting layer/hole-transporting layer/emitting layer/electron-transporting layer/electron-injecting layer/cathode
(9) Anode/insulating layer/hole-transporting layer/emitting layer/electron-transporting layer/cathode
(10) Anode/hole-transporting layer/emitting layer/electron-transporting layer/insulating layer/cathode
(11) Anode/inorganic semiconductor layer/insulating layer/hole-transporting layer/emitting layer/insulating layer/cathode
(12) Anode/insulating layer/hole-transporting layer/emitting layer/electron-transporting layer/insulating layer/cathode
(13) Anode/hole-injecting layer/hole-transporting layer/emitting layer/electron-transporting layer/insulating layer/cathode
(14) Anode/insulating layer/hole-injecting layer/hole-transporting layer/emitting layer/electron-transporting layer/electron-injecting layer/cathode
(15) Anode/insulating layer/hole-injecting layer/hole-transporting layer/emitting layer/electron-transporting layer/electron-injecting layer/insulating layer/cathode Among these, usually, the configurations (4), (6), (7), (8), (12), (13) and (15) are preferably used.

Each member constituting the organic EL device of the invention will be described below.

(Transparent Substrate)

The organic EL device is usually formed on a transparent substrate. The transparent substrate is a substrate for supporting the organic EL device, and is preferably a flat and smooth substrate having a 400-to-700-nm-visible-light transmittance of 50% or more.

Specific examples thereof include glass plates and polymer plates. Examples of the glass plate include soda-lime glass, barium/strontium-containing glass, lead glass, aluminosilicate glass, borosilicate glass, barium borosilicate glass, and quartz. Examples of the polymer plate include polycarbonate, acrylic polymer, polyethylene terephthalate, polyethersulfide, and polysulfone.

Transparency is not required when the supporting substrate is positioned in the direction opposite to the light-outcoupling direction.

(Anode)

The anode of the organic EL device plays a role for injecting holes into its hole-transporting layer or emitting layer. When transparency is required for the anode, indium tin oxide alloy (ITO), tin oxide (NESA), indium zinc oxide alloy (IZO), gold, silver, platinum, copper, and the like may be used as the material for the anode. When a reflective electrode which does not require transparency is used, in addition to those metals, a metal such as aluminum, molybdenum, chromium, and nickel or alloys thereof may also be used.

Even when the anode with a small work function (for example, 5.0 eV or less) and the hole-injecting layer using the material for the organic EL device of the invention are used in combination, electron transfer is possible and the hole-injecting layer shows good injection properties.

These materials may be used singly, or alloys of these materials or a material to which other elements are added may be selected appropriately and used.

The anode can be prepared by forming a thin film using these electrode materials by a method such as the vapor deposition method or the sputtering method.

In the case where emission from the emitting layer is taken out through the anode, the transmittance of the anode to the emission is preferably more than 10%. The sheet resistance of the anode is preferably several hundred Ω/□ or less. The film thickness of the anode, which varies depending upon the material thereof, is usually from 1 nm to 1 μm, preferably from 10 to 200 nm.

(Emitting Layer)

The emitting layer of the organic EL device has the following functions (1), (2) and (3) in combination.

(1) Injection function: function of allowing injection of holes from the anode or hole-injecting layer and injection of electrons from the cathode or electron-injecting layer upon application of an electric field
(2) Transporting function: function of moving injected carriers (electrons and holes) due to the force of an electric field
(3) Emitting function: function of allowing electrons and holes to recombine therein to emit light Note that electrons and holes may be injected into the emitting layer with different degrees, or the transportation capabilities indicated by the mobility of holes and electrons may differ. It is preferable that the emitting layer move either electrons or holes.

As the method for forming the emitting layer, a known method such as deposition, spin coating, or an LB method may be applied. It is preferable that the emitting layer be a molecular deposition film. Here, the molecular accumulation film means a thin film formed by deposition of a material compound in a vapor phase or a film formed by solidification of a material compound which is in a solution state or in a liquid state. The molecular deposition film is distinguished from a thin film (molecular accumulation film) formed using the LB method by the difference in aggregation structure or higher order structure or the difference in function due to the difference in structure.

The emitting layer may also be formed by dissolving a binder such as a resin and a material compound in a solvent to obtain a solution, and forming a thin film from the solution by spin coating or the like, as disclosed in JP-A-57-51781.

In the invention, if need arises, known emitting materials other than the emitting materials formed of the novel compound of the invention may be contained in the emitting layer insofar as the object of the invention is not impaired. An emitting layer containing other known emitting materials may be stacked on the emitting layer containing the emitting materials formed of the novel compound of the invention.

As the emitting material or the doping material used for the emitting layer, anthracene, naphthalene, phenanthrene, pyrene, tetracene, coronene, chrysene, fluorescein, perylene, phthaloperylene, naphthaloperylene, perynone, phthaloperynone, naphthaloperynone, diphenylbutadiene, tetraphenylbutadiene, coumarin, oxadiazole, aldazine, bisbenzoxazoline, bisstyryl, pyrazine, cyclopentadiene, a quinoline metal complex, an aminoguinoline metal complex, a benzoquinoline metal complex, imine, diphenylethylene, vinyl anthracene, diaminocarbazol, pyran, thiopyran, polymethine, merocyanine, an imidazole chelate oxanoid compound, quinacridone, rubrene, a fluorescent pigment and like can be given. Note that the emitting material and the doping material are not limited to these compounds.

As the host material for use in the emitting layer, the compounds shown by the following formulas (i) to (ix) are preferred.

Asymmetrical anthracene shown by the following formula (i):

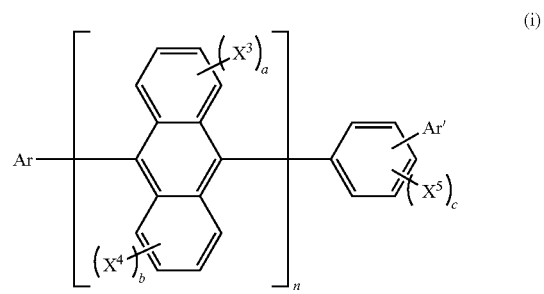

wherein Ar is a substituted or unsubstituted condensed aromatic group having 10 to 50 carbon atoms forming a ring (hereinafter referred to as a "ring carbon atom"), Ar' is a substituted or unsubstituted aromatic group having 6 to 50 ring carbon atoms, $X^3$ to $X^5$ are independently a substituted or unsubstituted aromatic group having 6 to 50 ring carbon atoms, a substituted or unsubstituted aromatic heterocyclic group having 5 to 50 atoms forming a ring (hereinafter referred to as a "ring atom"), a substituted or unsubstituted alkyl group having 1 to 50 carbon atoms, a substituted or unsubstituted alkoxy group having 1 to 50 carbon atoms, a substituted or unsubstituted aralkyl group having 6 to 50 carbon atoms, a substituted or unsubstituted aryloxy group having 5 to 50 ring atoms, a substituted or unsubstituted arylthio group having 5 to 50 ring atoms, a substituted or unsubstituted alkoxycarbonyl group having 1 to 50 carbon atoms, a carboxyl group, a halogen atom, a cyano group, a nitro group or a hydroxyl group.

a, b and c are each an integer of 0 to 4.

n is an integer of 1 to 3. When n is 2 or more, the anthracene in [ ] may be the same or different.

Asymmetrical monoanthracene derivatives shown by the following formula (ii):

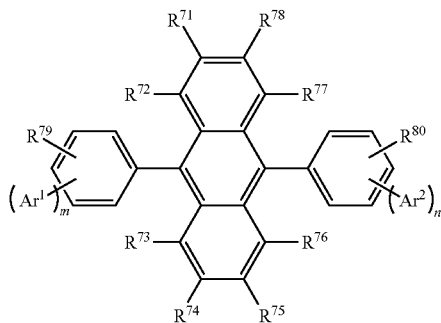

wherein $Ar^1$ and $Ar^2$ are independently a substituted or unsubstituted aromatic ring group having 6 to 50 ring carbon atoms, and m and n are each an integer of 1 to 4, provided that in the case where $m=n=1$ and $Ar^1$ and $Ar^2$ are symmetrically bonded to the benzene rings, $Ar^1$ and $Ar^2$ are not the same, and in the case where m or n is an integer of 2 to 4, m is different from n.

$R^{71}$ to $R^{80}$ are independently a hydrogen atom, a substituted or unsubstituted aromatic ring group having 6 to 50 ring carbon atoms, a substituted or unsubstituted aromatic hetrocyclic group having 5 to 50 ring atoms, a substituted or unsubstituted alkyl group having 1 to 50 carbon atoms, a substituted or unsubstituted cycloalkyl group, a substituted or unsubstituted alkoxy group having 1 to 50 carbon atoms, a substituted or unsubstituted aralkyl group having 6 to 50 carbon atoms, a substituted or unsubstituted aryloxy group having 5 to 50 ring atoms, a substituted or unsubstituted arylthio group having 5 to 50 ring atoms, a substituted or unsubstituted alkoxycarbonyl group having 1 to 50 carbon atoms, a substituted or unsubstituted silyl group, a carboxyl group, a halogen atom, a cyano group, a nitro group or a hydroxyl group.

Asymmetrical pyrene derivatives shown by the following formula (iii)

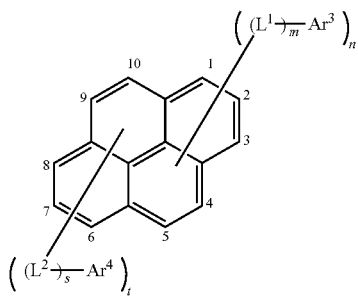

wherein $Ar^3$ and $Ar^4$ are independently a substituted or unsubstituted aromatic group having 6 to 50 ring carbon atoms;

$L^1$ and $L^2$ are each a substituted or unsubstituted phenylene group, a substituted or unsubstituted naphthalenylene group, a substituted or unsubstituted fluolenylene group, or a substituted or unsubstituted dibenzosilolylene group;

m is an integer of 0 to 2, n is an integer of 1 to 4, s is an integer of 0 to 2, and t is an integer of 0 to 4;

$L^1$ or $Ar^3$ bonds at any one position of 1 to 5 of the pyrene, and $L^2$ or $Ar^4$ bonds at any one position of 6 to 10 of the pyrene; provided that when n+t is an even number, $Ar^3$, $Ar^4$, $L^1$ and $L^2$ satisfy the following (1) and (2):

(1) $Ar^3 \neq Ar^4$ and/or $L^1 \neq L^2$ where ≠ means these substituents are groups having different structures from each other.

(2) When $Ar^3 = Ar^4$ and $L^1 = L^2$, (2-1) $m \neq s$ and/or $n \neq t$, or (2-2) when $m=s$ and $n=t$, (2-2-1) when $L^1$ and $L^2$ or pyrene are independently bonded to different bonding positions of $Ar^3$ and $Ar^4$, (2-2-2) when $L^1$ and $L^2$ or pyrene are bonded to the same position of $Ar^3$ and $Ar^4$, the position of the substitution of $L^1$ and $L^2$ or $Ar^3$ and $Ar^4$ at pyrene are not necessarily be the $1^{st}$ position and the $6^{th}$ position, or the $2^{nd}$ position and the $7^{th}$ position.

Asymmetrical anthracene shown by the following formula (iv):

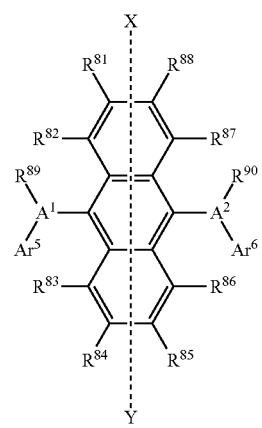

wherein $A^1$ and $A^2$ are independently a substituted or unsubstituted condensed aromatic ring group having 10 to 20 ring carbon atoms, $Ar^5$ and $Ar^6$ are independently a hydrogen atom or a substituted or unsubstituted aromatic ring group with 6 to 50 ring carbon atoms, $R^{81}$ to $R^{90}$ are independently a hydrogen atom, a substituted or unsubstituted aromatic ring group having 6 to 50 ring carbon atoms, a substituted or unsubstituted aromatic heterocyclic group having 5 to 50 ring atoms, a substituted or unsubstituted alkyl group having 1 to 50 carbon atoms, a substituted or unsubstituted cycloalkyl group, a substituted or unsubstituted alkoxy group having 1 to 50 carbon atoms, a substituted or unsubstituted aralkyl group having 6 to 50 carbon atoms, a substituted or unsubstituted aryloxy group having 5 to 50 ring atoms, a substituted or unsubstituted arylthio group having 5 to 50 ring atoms, a substituted or unsubstituted alkoxycarbonyl group having 1 to 50 carbon atoms, a substituted or unsubstituted silyl group, a carboxyl group, a halogen atom, a cyano group, a nitro group or a hydroxyl group, and each of $Ar^5$, $Ar^6$, $R^{89}$ and $R^{90}$ may be plural, and adjacent groups thereof may form a saturated or unsaturated ring structure, provided that groups do not symmetrically bond to 9 and 10 positions of the central anthracene with respect to X-Y axis.

Anthracene derivative shown by the following formula (v)

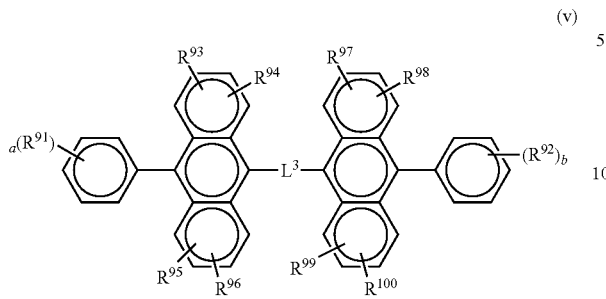

(v)

wherein $R^{91}$ to $R^{100}$ are independently a hydrogen atom, an alkyl group, a cycloalkyl group, an aryl group which may be substituted, an alkoxy group, an aryloxy group, an alkylamino group, an alkenyl group, an arylamino group or a heterocyclic group which may be substituted; a and b are each an integer of 1 to 5; when they are 2 or more, $R^{91}$s or $R^{92}$s may be the same or different, or $R^{91}$s or $R^{92}$s may be bonded together to form a ring; $R^{93}$ and $R^{94}$, $R^{95}$ and $R^{96}$, $R^{97}$ and $R^{98}$, or $R^{99}$ and $R^{100}$ may be bonded together to form a ring; and $L^3$ is a single bond, —O—, —S—, —N(R)— (R is an alkyl group or a substituted or unsubstituted aryl group), an alkylene group or an arylene group.

Anthracene derivative shown by the following formula (vi):

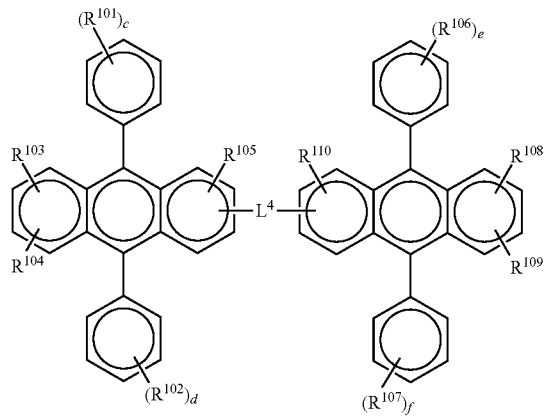

(vi)

wherein $R^{101}$ to $R^{110}$ are independently a hydrogen atom, an alkyl group, a cycloalkyl group, an aryl group, an alkoxy group, an aryloxy group, an alkylamino group, an arylamino group or a heterocyclic group which may be substituted; c, d, e and f are each an integer of 1 to 5; when they are 2 or more, $R^{101}$s, $R^{102}$s, $R^{106}$s or $R^{107}$s may be the same or different, $R^{101}$s, $R^{102}$s, $R^{106}$s or $R^{107}$s may be bonded to each other to form a ring, or $R^{103}$ and $R^{104}$, or $R^{108}$ and $R^{109}$ may be bonded to each other to form a ring; $L^4$ is a single bond, —O—, —S—, —N(R)— (R is an alkyl group or a substituted or unsubstituted aryl group), an alkylene group or an arylene group.

Spirofluorene derivatives shown by the following formula (vii):

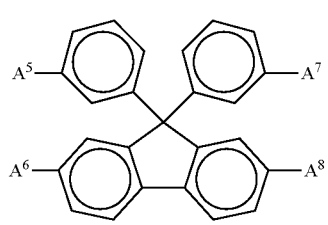

(vii)

wherein $A^5$ to $A^8$ are independently a substituted or unsubstituted biphenyl group or a substituted or unsubstituted naphthyl group.

Condensed ring-containing compounds shown by the following formula (viii):

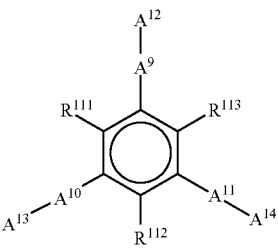

(viii)

wherein $A^9$ to $A^{14}$ are the same as the above-described ones and $R^{111}$ to $R^{113}$ are independently a hydrogen atom, alkyl group having 1 to 6 carbon atoms, cycloalkyl group having 3 to 6 carbon atoms, alkoxy group having 1 to 6 carbon atoms, aryloxy group having 5 to 18 carbon atoms, aralkyloxy group having 7 to 18 carbon atoms, arylamino group having 5 to 16 carbon atoms, nitro group, cyano group, ester group having 1 to 6 carbon atoms, or a halogen atom, provided that at least one of $A^9$ to $A^{14}$ is a group having a condensed aromatic ring with three or more rings.

Fluorene compound shown by the following formula (ix):

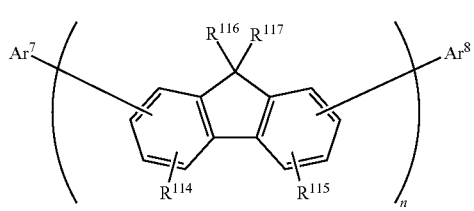

(ix)

wherein $R^{114}$ and $R^{115}$ are a hydrogen atom, a substituted or unsubstituted alkyl group, substituted or unsubstituted aralkyl group, substituted or unsubstituted aryl group, substituted or unsubstituted heterocyclic group, substituted amino group, cyano group, or a halogen atom; $R^{114}$s bonded to different fluorene groups may be the same or different, and $R^{114}$ and $R^{115}$ bonded to a single fluorene group may be the same or different, $R^{116}$ and $R^{117}$ are a hydrogen atom, a substituted or unsubstituted alkyl group, substituted or unsubstituted aralkyl group, substituted or unsubstituted aryl group, or substituted or unsubstituted heterocyclic group, provided that $R^{116}$s or $R^{117}$s bonded to different fluorene groups may be the same or different, and $R^{116}$ and $R^{117}$ bonded to a single fluorene group may be the same or different; $Ar^7$ and $Ar^8$ are a substituted or unsubstituted condensed polycyclic aromatic group with a total number of benzene rings of three or more or a condensed polycyclic heterocyclic group which is bonded to the fluorene group through substituted or unsubstituted carbon and has a total number of benzene rings and heterocyclic rings of three or more, provided that $Ar^7$ and $Ar^8$ may be the same or different; and n is an integer of 1 to 10.

Among the above-mentioned host materials, the anthracene derivative is preferable, and the monoanthracene derivative is more preferable with the asymmetrical anthracene being particularly preferable.

Phosphorescent compounds can be used as an emitting material. When using a phosphorescent compound, compounds containing a carbazole ring are preferred for a host material. A dopant is a compound that can emit light from triplet excitons. The dopant is not limited so long as it can emit light from triplet excitons, but it is preferably a metal complex containing at least one metal selected from the group of Ir, Ru, Pd, Pt, Os and Re. A porphyrin metal complex or an ortho-metalated metal complex is preferable.

The compounds containing a carbazole ring, which are a host suitable for phosphorescence emission, is a compound which allows a phosphorescent compound to emit as a result of energy transfer from its excited state to the phosphorescent compound. The host compound is not limited so long as the compound can transfer its excited energy to a phosphorescent compound and it can be selected depending on purposes. The host compound may contain any heterocyclic ring other than a carbazole ring.

Specific examples of the host compounds include carbazole, triazole, oxazole, oxadiazole, imidazole, polyarylalkane, pyrazoline, pyrazolone, phenylenediamine, arylamine, amino-substituted calcone, styryl anthracene, fluorenone, hydrazone, stilbene and silazane derivatives; aromatic tertiary amine, styrylamine, aromatic dimethylidene and porphyrin compounds; anthraquinodimethane, anthrone, diphenylquinone, thiopyrandioxide, carbodiimide, fluoreniridenemethane and distyrylpyrazine derivatives; heterocyclic tetracarboxylic anhydrides such as naphthaleneperylene; phthalocyanine derivatives; metal complexes of 8-quinolinol derivatives; various metal complex polysilane compounds shown by metal complexes having metalphthalocyanine, benzoxazole or benzothiaole as a ligand; electroconductive macromolecular oligomers such as poly(N-vinylcarbazole) derivatives, aniline copolymers, thiophene oligomers and polythiophene; and macromolecular compounds such as polythiophene, polyphenylene, polyphenylenevinylene and polyfluorene derivatives. Host compounds can be used individually or as a combination of two or more kinds.

Specific compounds shown below can be exemplified.

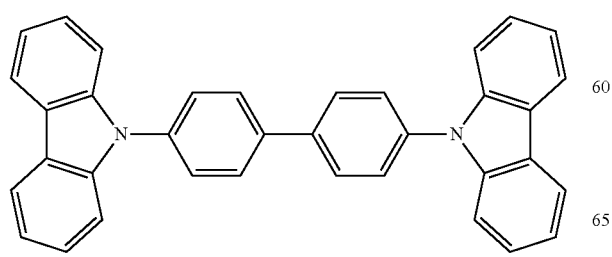

-continued

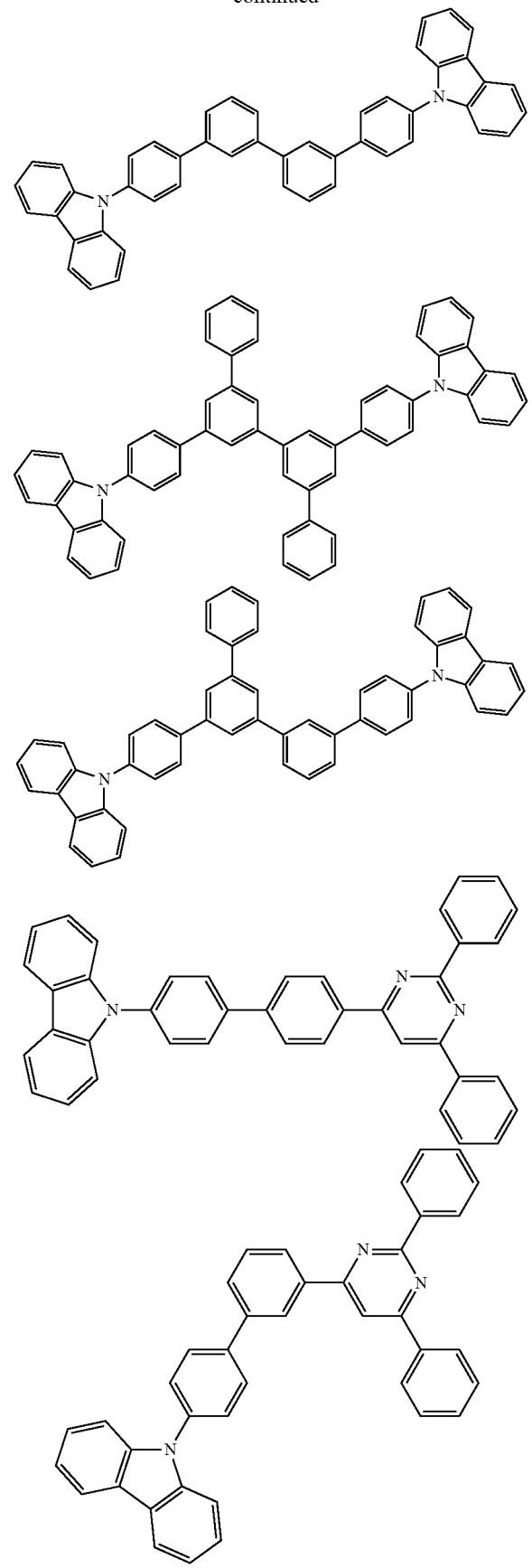

A phosphorescent dopant is a compound that can emit light from triplet excitons. The dopant is not limited so long as it can emit light from triplet excitons, but it is preferably a metal complex containing at least one metal selected from the group of Ir, Ru, Pd, Pt, Os and Re. A porphyrin metal complex or an ortho-metalated metal complex is preferable. As a porphyrin metal complex, a porphyrin platinum complex is preferable. The phosphorescent compounds can be used individually or as a combination of two or more kinds.

There are various ligands forming an ortho-metalated metal complex. Preferable ligands include 2-phenylpyridine, 7,8-benzoquinoline, 2-(2-thienyl)pyridine, 2-(1-naphtyl)pyridine and 2-phenylquinoline derivatives. These derivatives may have substituents, if necessary. Fluorides and derivatives with a trifluoromethyl group introduced are particularly preferable as a blue dopant. As an auxiliary ligand, ligands other than the above-mentioned ligands, such as acetylacetonate and picric acid may be contained.

The content of a phosphorescent dopant in an emitting layer is not limited and can be properly selected according to purposes; for example, it is 0.1 to 70 mass %, preferably 1 to 30 mass %. When the content of a phosphorescent compound is less than 0.1 mass %, emission may be weak and the advantages thereof may not be sufficiently obtained. When the content exceeds 70 mass %, the phenomenon called concentration quenching may significantly proceed, thereby degrading the device performance.

The emitting layer may contain hole-transporting materials, electron-transporting materials and polymer binders, if necessary.

The thickness of an emitting layer is preferably from 5 to 50 nm, more preferably from 7 to 50 nm and most preferably from 10 to 50 nm. When it is less than 5 nm, the formation of an emitting layer and the adjustment of chromaticity may become difficult. When it exceeds 50 nm, the driving voltage may increase.

(Hole-transporting Layer:Hole-injecting Layer)

The hole-transporting layer is a layer for helping the injection of holes into the emitting layer so as to transport holes to an emitting region. The hole mobility thereof is large and the ionization energy thereof is usually as small as 5.5 eV or less. Such a hole-transporting layer is preferably made of a material which can transport holes to the emitting layer at a low electric field intensity. In addition, for example, it is preferred that the hole mobility be at least $10^{-4}$ cm$^2$/V·sec when an electric field of $10^4$ to $10^6$ V/cm is impressed.

Specific examples of materials for a hole-transporting layer include triazole derivatives (see U.S. Pat. No. 3,112,197 and others), oxadiazole derivatives (see U.S. Pat. No. 3,189,447 and others), imidazole derivatives (see JP-B-37-16096 and others), polyarylalkane derivatives (see U.S. Pat. Nos. 3,615,402, 3,820,989 and 3,542,544, JP-B-45-555 and 51-10983, JP-A-51-93224, 55-17105, 56-4148, 55-108667, 55-156953 and 56-36656, and others), pyrazoline derivatives and pyrazolone derivatives (see U.S. Pat. Nos. 3,180,729 and 4,278,746, JP-A-55-88064, 55-88065, 49-105537, 55-51086, 56-80051, 56-88141, 57-45545, 54-112637 and 55-74546, and others), phenylene diamine derivatives (see U.S. Pat. No. 3,615,404, JP-B-51-10105, 46-3712 and 47-25336, and 54-119925, and others), arylamine derivatives (see U.S. Pat. Nos. 3,567,450, 3,240,597, 3,658,520, 4,232,103, 4,175,961 and 4,012,376, JP-B-49-35702 and 39-27577, JP-A-55-144250, 56-119132 and 56-22437, DE1,110,518, and others), amino-substituted chalcone derivatives (see U.S. Pat. No. 3,526,501, and others), oxazole derivatives (ones disclosed in U.S. Pat. No. 3,257,203, and others), styrylanthracene derivatives (see JP-A-56-46234, and others), fluorenone derivatives (JP-A-54-110837, and others), hydrazone derivatives (see U.S. Pat. No. 3,717,462, JP-A-54-59143, 55-52063, 55-52064, 55-46760, 57-11350, 57-148749 and 2-311591, and others), stilbene derivatives (see JP-A-61-210363, 61-228451, 61-14642, 61-72255, 62-47646, 62-36674, 62-10652, 62-30255, 60-93455, 60-94462, 60-174749 and 60-175052, and others), silazane derivatives (U.S. Pat. No. 4,950,950), polysilanes (JP-A-2-204996), aniline copolymers (JP-A-2-282263), and electroconductive high molecular oligomers (in particular thiophene oligomers).

In addition to the hole-transporting layer, in order to help the injection of holes, it is preferred that the hole-injecting layer be provided separately. As the material for the hole-injecting layer, the organic EL material of the invention may be used singly or in combination with other materials. As the other materials, the same materials as used for the hole-transporting layer or the compounds exemplified by the above-mentioned formula (IV) can be used. The following can also be used: porphyrin compounds (disclosed in JP-A-63-295695 and others), aromatic tertiary amine compounds and styrylamine compounds (see U.S. Pat. No. 4,127,412, JP-A-53-27033, 54-58445, 55-79450, 55-144250, 56-119132, 61-295558, 61-98353 and 63-295695, and others).

The following can also be given as examples: 4,4'-bis(N-(1-naphthyl)-N-phenylamino)biphenyl (NPD), which has in the molecule thereof two condensed aromatic rings, disclosed in U.S. Pat. No. 5,061,569, and 4,4',4''-tris(N-(3-methylphenyl)-N-phenylamino)triphenylamine (MTDATA), wherein three triphenylamine units are linked in a star-burst form, disclosed in JP-A-4-308688.

Inorganic compounds such as p-type Si and p-type SiC as well as aromatic dimethylidene type compounds can also be used as the material of the hole-injecting layer.

The hole-injecting layer or the hole-transporting layer can be formed, for example, from the above-mentioned compounds by a known method such as vacuum deposition, spin coating, casting or LB technique. The film thickness of the hole-injecting layer and hole-transporting layer is not particularly limited, and is usually from 1 nm to 5 μm. The hole-injecting layer or hole-transporting layer may be a single layer made of one or two or more of the above-mentioned materials, or may be stacked hole-injecting layers or hole-transporting layers made of different compounds, insofar as the compound of the invention is contained in the hole-transporting region.

An organic semiconductor layer is one type of a hole-transporting layer for helping the injection of holes or electrons into an emitting layer, and is preferably a layer having an electric conductivity of $10^{-10}$ S/cm or more. As the material of such an organic semiconductor layer, electroconductive oligomers such as thiophene-containing oligomers or arylamine-containing oligomers disclosed in JP-A-8-193191, and electroconductive dendrimers such as arylamine-containing dendrimers may be used.

(Electron-injecting/Transporting Layer)

The electron-injecting/transporting layer is a layer which assists injection of electrons into the emitting layer and transports electrons to the emitting region, and exhibits a high degree of electron mobility. An adhesion-improving layer is formed of a material which exhibits excellent adhesion to the cathode.

The thickness of the electron-transporting layer is arbitrarily selected in the range of several nanometers to several micrometers. When the electron-transporting layer has a large thickness, it is preferable that the electron mobility be at least $10^{-5}$ cm²/Vs or more at an applied electric field of $10^4$ to $10^6$ V/cm in order to prevent an increase in voltage.

The material used in the electron-transporting layer is preferably a metal complex of 8-hydroxyquinoline or a derivative thereof or an oxadiazole derivative. As specific examples of 8-hydroxyquinoline and a metal complex of an 8-hydroxyquinoline derivative, metal chelate oxinoid compounds including a chelate of oxine (8-quinolinol or 8-hydroxyquinoline) can be given.

An electron-transporting compound of the following general formula can be given as the oxadiazole derivative.

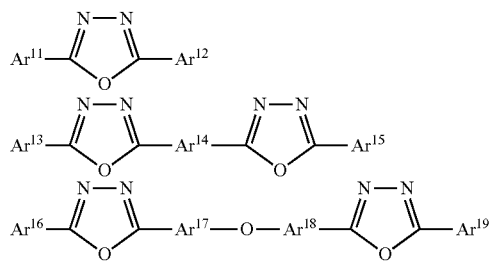

wherein $Ar^{11}$, $Ar^{12}$, $Ar^{13}$, $Ar^{15}$, $Ar^{16}$ and $Ar^{19}$ are independently substituted or unsubstituted aryl groups and may be the same or different. $Ar^{14}$, $Ar^{17}$ and $Ar^{18}$ are independently substituted or unsubstituted arylene groups and may be the same or different.

As examples of the aryl group, a phenyl group, a biphenyl group, an anthryl group, a perylenyl group, and a pyrenyl group can be given. As examples of the arylene group, a phenylene group, a naphthylene group, a biphenylene group, an anthrylene group, a perylenylene group, a pyrenylene group, and the like can be given. As the substituent, an alkyl group having 1 to 10 carbon atoms, an alkoxy group having 1 to 10 carbon atoms, a cyano group, and the like can be given. The electron-transporting compound is preferably one from which a thin film can be formed.

The following compounds can be given as specific examples of the electron-transporting compound.

Furthermore, as materials used for the electron-injecting layer and electron-transporting layer, the compounds shown by the following formulas (A) to (F) may be used.

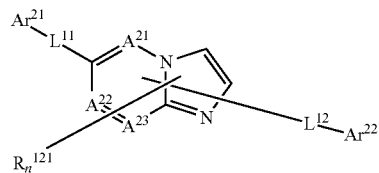

(A)

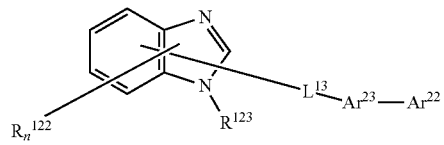

(B)

Nitrogen-containing heterocyclic ring derivatives shown by the formulas (A) and (B) wherein $A^{21}$ to $A^{23}$ are independently a nitrogen atom or a carbon atom;

$Ar^{21}$ is a substituted or unsubstituted aryl group having 6 to 60 ring carbon atoms or a substituted or unsubstituted heteroaryl group having 3 to 60 ring carbon atoms; $Ar^{22}$ is a hydrogen atom, a substituted or unsubstituted aryl group having 6 to 60 ring carbon atoms, a substituted or unsubstituted heteroaryl group having 3 to 60 ring carbon atoms, a substituted or unsubstituted alkyl group having 1 to 20 carbon atoms, a substituted or unsubstituted alkoxy group having 1 to 20 carbon atoms, or a divalent group of these; provided that one of $Ar^{21}$ and $Ar^{22}$ is a substituted or unsubstituted condensed ring group having 10 to 60 ring carbon atoms, a substituted or unsubstituted monohetero condensed ring group having 3 to 60 ring carbon atoms, or a divalent group of these;

$Ar^{23}$ is a substituted or unsubstituted arylene group having 6 to 60 carbon atoms or a substituted or unsubstituted heteroarylene group having 3 to 60 carbon atoms;

$L^{11}$, $L^{12}$ and $L^{13}$ are independently a single bond, a substituted or unsubstituted arylene group having 6 to 60 ring

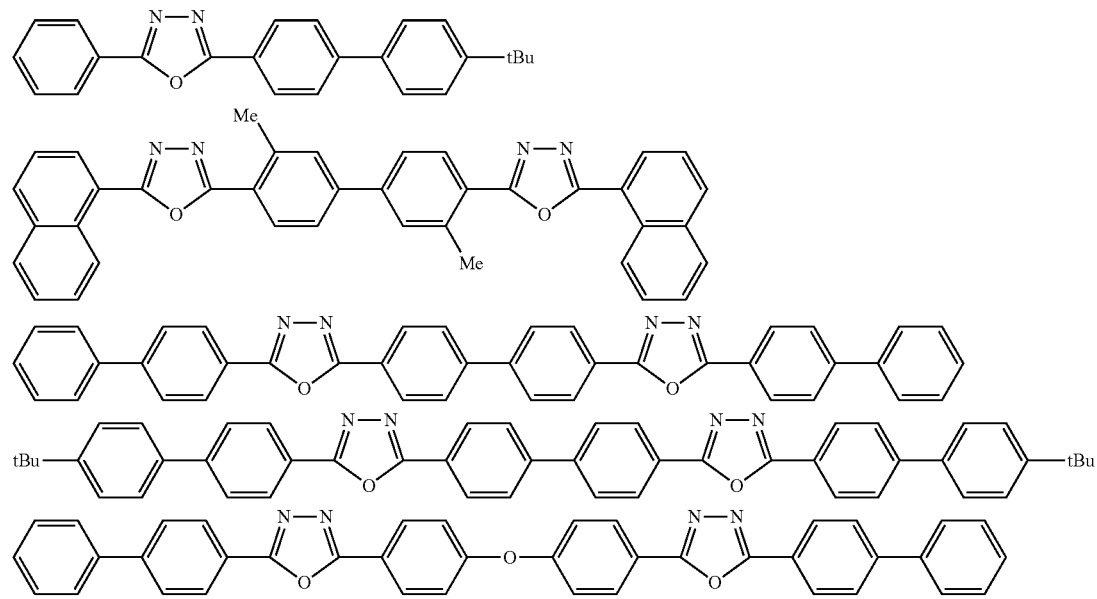

carbon atoms, a substituted or unsubstituted heteroarylene group having 3 to 60 ring carbon atoms or a substituted or unsubstituted fluorenylene group;

$R^{121}$ and $R^{122}$ are independently a hydrogen atom, a substituted or unsubstituted aryl group having 6 to 60 ring carbon atoms, a substituted or unsubstituted heteroaryl group having 3 to 60 ring carbon atoms, a substituted or unsubstituted alkyl group having 1 to 20 carbon atoms, or a substituted or unsubstituted alkoxy group having 1 to 20 carbon atoms, and n is an integer of 0 to 5, provided that, when n is an integer of 2 or more, a plurality of $R^{121}$s and $R^{122}$s may be the same or different; adjacent $R^{121}$s and $R^{122}$s may be bonded to form a carbocyclic aliphatic ring or a carbocyclic aromatic ring;

$R^{123}$ is a hydrogen atom, a substituted or unsubstituted aryl group having 6 to 60 ring carbon atoms, a substituted or unsubstituted heteroaryl group having 3 to 60 ring carbon atoms, a substituted or unsubstituted alkyl group having 1 to 20 carbon atoms, a substituted or unsubstituted alkoxy group having 1 to 20 carbon atoms or $-L^{11}-Ar^{21}-Ar^{22}$.

A nitrogen-containing heterocyclic derivative shown by the formula (C):

$$HAr-L^{14}-Ar^{24}-Ar^{25} \quad (C)$$

wherein HAr is a nitrogen-containing heterocyclic ring with 3 to 40 carbon atoms which may have a substituent; $L^{14}$ is a single bond, an arylene group with 6 to 60 carbon atoms which may have a substituent, a heteroarylene group with 3 to 60 carbon atoms which may have a substituent or a fluorenylene group which may have a substituent; $Ar^{24}$ is a divalent aromatic hydrocarbon group with 6 to 60 carbon atoms which may have a substituent; and $Ar^{25}$ is an aryl group with 6 to 60 carbon atoms which may have a substituent or a heteroaryl group with 3 to 60 carbon atoms which may have a substituent.

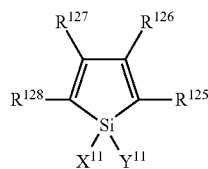

(D)

Silacyclopentadiene derivatives shown by the above formula (D) wherein $X^{11}$ and $Y^{11}$ are independently a saturated or unsaturated hydrocarbon group having 1 to 6 carbon atoms, an alkoxy group, an alkenyloxy group, an alkynyloxy group, a hydroxyl group, a substituted or unsubstituted aryl group, or a substituted or unsubstituted hetero ring, or $X^{11}$ and $Y^{11}$ are bonded to form a saturated or unsaturated ring, and $R^{125}$ to $R^{128}$ are independently a hydrogen atom, a halogen atom, a substituted or unsubstituted aryl group having 1 to 6 carbon atoms, an alkoxy group, an aryloxy group, a perfluoroalkyl group, a perfluoroalkoxy group, an amino group, an alkylcarbonyl group, an arylcarbonyl group, an alkoxycarbonyl group, an aryloxycarbonyl group, an azo group, an alkylcarbonyloxy group, an arylcarbonyloxy group, an alkoxycarbonyloxy group, an aryloxycarbonyloxy group, a sulfinyl group, a sulfonyl group, a sulfanyl group, a silyl group, a carbamoyl group, an aryl group, a heterocyclic group, an alkenyl group, an alkynyl group, a nitro group, a formyl group, a nitroso group, a formyloxy group, an isocyano group, a cyanate group, an isocyanate group, a thiocyanate group, an isothiocyanate group, or a cyano group, or adjacent groups of $R^{125}$ to $R^{128}$ form a substituted or unsubstituted condensed ring.

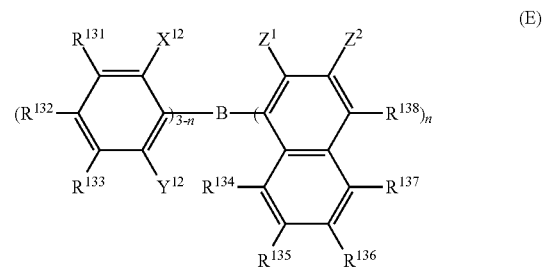

Borane derivatives shown by the above formula wherein $R^{131}$ to $R^{138}$ and $Z^2$ are independently a hydrogen atom, a saturated or unsaturated hydrocarbon group, an aromatic group, a heterocyclic group, a substituted amino group, a substituted boryl group, an alkoxy group, or an aryloxy group, $X^{12}$, $Y^{12}$, and $Z^1$ are independently a saturated or unsaturated hydrocarbon group, an aromatic group, a heterocyclic group, a substituted amino group, an alkoxy group, or an aryloxy group, the substituents for $Z^1$ and $Z^2$ may be bonded to form a condensed ring, n is an integer of 1 to 3, provided that the $Z^1$s may differ when n is 2 or more, and a case in which n is 1, $X^{12}$, $Y^{12}$, and $R^{132}$ are methyl groups, and $R^{138}$ is a hydrogen atom or a substituted boryl group, and a case in which n is 3 and $Z^1$ is a methyl group are excluded.

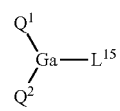

(F)

wherein $Q^1$ and $Q^2$ are independently ligands shown by the following formula (G) and $L^{15}$ is a halogen atom, a substituted or unsubstituted alkyl group, a substituted or unsubstituted cycloalkyl group, a substituted or unsubstituted aryl group, a substituted or unsubstituted heterocyclic group, —OR' (R' is a hydrogen atom, a substituted or unsubstituted alkyl group, a substituted or unsubstituted cycloalkyl group, a substituted or unsubstituted aryl group, or a substituted or unsubstituted heterocyclic group) or a ligand shown by —O—Ga-$Q^3(Q^4)$ ($Q^3$ and $Q^4$ have the same meanings as $Q^1$ and $Q^2$).

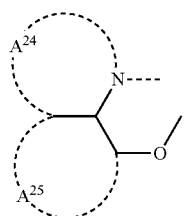

(G)

wherein rings $A^{24}$ and $A^{25}$ are a 6-membered aryl ring structure which may have a substituent, and are condensed to each other.

The metal complexes have the strong nature of an n-type semiconductor and large ability of injecting electrons. Furthermore, the energy generated at the time of forming a complex is small so that a metal is then strongly bonded to ligands in the complex formed and the fluorescent quantum efficiency becomes large as the emitting material.

Specific examples of the substituents for the rings $A^{24}$ and $A^{25}$ forming the ligand of the above formula (G) include halogen atoms such as chlorine, bromine, iodine, and fluorine, substituted or unsubstituted alkyl groups such as a methyl group, ethyl group, propyl group, butyl group, sec-butyl group, tert-butyl group, pentyl group, hexyl group, heptyl group, octyl group, stearyl group, and trichloromethyl group, substituted or unsubstituted aryl groups such as a phenyl group, naphthyl group, 3-methylphenyl group, 3-methoxyphenyl group, 3-fluorophenyl group, 3-trichloromethylphenyl group, 3-trifluoromethylphenyl group, and 3-nitrophenyl group, substituted or unsubstituted alkoxy groups such as a methoxy group, n-butoxy group, tert-butoxy group, trichloromethoxy group, trifluoroethoxy group, pentafluoropropoxy group, 2,2,3,3-tetrafluoropropoxy group, 1,1,1,3,3,3-hexafluoro-2-propoxy group, and 6-(perfluoroethyl)hexyloxy group, substituted or unsubstituted aryloxy groups such as a phenoxy group, p-nitrophenoxy group, p-tert-butylphenoxy group, 3-fluorophenoxy group, pentafluorophenyl group, and 3-trifluoromethylphenoxy group, substituted or unsubstituted alkylthio groups such as a methylthio group, ethylthio group, tert-butylthio group, hexylthio group, octylthio group, and trifluoromethylthio group, substituted or unsubstituted arylthio groups such as a phenylthio group, p-nitrophenylthio group, p-tert-butylphenylthio group, 3-fluorophenylthio group, pentafluorophenylthio group, and 3-trifluoromethylphenylthio group, a cyano group, a nitro group, an amino group, mono- or di-substituted amino groups such as a methylamino group, diethylamino group, ethylamino group, diethylamino group, dipropylamino group, dibutylamino group, and diphenylamino group, acylamino groups such as a bis(acetoxymethyl)amino group, bis(acetoxyethyl)amino group, bis(acetoxypropyl) amino group, and bis(acetoxybutyl)amino group, a hydroxyl group, a siloxy group, an acyl group, substituted or unsubstituted carbamoyl groups such as a carbamoyl group, methylcarbamoyl group, dimethylcarbamoyl group, ethylcarbamoyl group, diethylcarbamoyl group, propylcarbamoyl group, butylcarbamoyl group, and phenylcarbamoyl group, a carboxylic acid group, a sulfonic acid group, an imide group, cycloalkyl groups such as a cyclopentane group and a cyclohexyl group, aryl groups such as a phenyl group, naphthyl group, biphenyl group, anthryl group, phenanthryl group, fluorenyl group, and pyrenyl group, heterocyclic groups such as a pyridinyl group, pyrazinyl group, pyrimidinyl group, pyridazinyl group, triathyl group, indolinyl group, quinolinyl group, acridinyl group, pyrrolidinyl group, dioxanyl group, piperidinyl group, morpholidinyl group, piperazinyl group, triathinyl group, carbazolyl group, furanyl group, thiophenyl group, oxazolyl group, oxadiazolyl group, benzooxazolyl group, thiazolyl group, thiadiazolyl group, benzothiazolyl group, triazolyl group, imidazolyl group, benzoimidazolyl group, and the like. The above substituents may be bonded to form a six-membered aryl ring or heterocyclic ring.

A preferred embodiment of the invention is a device containing a reducing dopant in an electron-transporting region or in an interfacial region between the cathode and the organic layer. The reducing dopant is defined as a substance which can reduce an electron-transporting compound. Accordingly, various substances which have given reducing properties can be used. For example, at least one substance can be preferably used which is selected from the group consisting of alkali metals, alkaline earth metals, rare earth metals, alkali metal oxides, alkali metal halides, alkaline earth metal oxides, alkaline earth metal halides, rare earth metal oxides, rare earth metal halides, alkali metal organic complexes, alkaline earth metal organic complexes, and rare earth metal organic complexes.

More specific examples of the preferred reducing dopants include at least one alkali metal selected from the group consisting of Li (work function: 2.9 eV), Na (work function: 2.36 eV), K (work function: 2.28 eV), Rb (work function: 2.16 eV) and Cs (work function: 1.95 eV), and at least one alkaline earth metal selected from the group consisting of Ca (work function: 2.9 eV), Sr (work function: 2.0 to 2.5 eV), and Ba (work function: 2.52 eV). A reducing dopant having a work function of 2.9 eV or less is particularly preferable.

Among these, a more preferable reducing dopant is at least one alkali metal selected from the group consisting of K, Rb and Cs. Even more preferable is Rb or Cs. Most preferable is Cs.

These alkali metals are particularly high in reducing ability. Thus, the addition of a relatively small amount thereof to an electron-injecting zone improves the luminance of the organic EL device and make the lifetime thereof long. As a reducing agent having a work function of 2.9 eV or less, combinations of two or more alkali metals are preferable, particularly combinations including Cs, such as Cs and Na, Cs and K, Cs and Rb, or Cs, Na and K are preferable.

The combination containing Cs makes it possible to exhibit the reducing ability efficiently. The luminance of the organic EL device can be improved and the lifetime thereof can be made long by the addition thereof to its electron-injecting zone.

In the invention, an electron-injecting layer made of an insulator or a semiconductor may further be provided between a cathode and an organic layer. By forming the electron-injecting layer, a current leakage can be effectively prevented and electron-injecting properties can be improved.

As the insulator, at least one metal compound selected from the group consisting of alkali metal calcogenides, alkaline earth metal calcogenides, halides of alkali metals and halides of alkaline earth metals can be preferably used. When the electron-injecting layer is formed of the alkali metal calcogenide or the like, the injection of electrons can be preferably further improved.

Specifically preferable alkali metal calcogenides include $Li_2O$, LiO, $Na_2S$, $Na_2Se$ and NaO and preferable alkaline earth metal calcogenides include CaO, BaO, SrO, BeO, BaS and CaSe. Preferable halides of alkali metals include LiF, NaF, KF, CsF, LiCl, KCl and NaCl. Preferable halides of alkaline earth metals include fluorides such as $CaF_2$, $BaF_2$, $SrF_2$, $MgF_2$ and $BeF_2$ and halides other than fluorides.

Semiconductors forming an electron-transporting layer include one or combinations of two or more of oxides, nitrides, and oxidized nitrides containing at least one element of Ba, Ca, Sr, Yb, Al, Ga, In, Li, Na, Cd, Mg, Si, Ta, Sb and Zn.

An inorganic compound forming an electron-transporting layer is preferably a microcrystalline or amorphous insulating thin film. When the electron-transporting layer is formed of the insulating thin films, more uniformed thin film is formed whereby pixel defects such as a dark spot are decreased.

Examples of such an inorganic compound include the above-mentioned alkali metal calcogenides, alkaline earth metal calcogenides, halides of alkali metals, and halides of alkaline earth metals.

(Cathode)

For the cathode, the following may be used: an electrode substance made of a metal, an alloy or an electroconductive compound, or a mixture thereof which has a small work function (for example, 4 eV or less). Specific examples of the electrode substance include sodium, sodium-potassium alloy, magnesium, lithium, magnesium/silver alloy, aluminum/aluminum oxide, aluminum/lithium alloy, indium, and rare earth metals.

This cathode can be formed by making the electrode substances into a thin film by vapor deposition, sputtering or some other method.

In the case where light is emitted from the emitting layer through the cathode, the cathode preferably has a light transmittance of larger than 10%.

The sheet resistance of the cathode is preferably several hundred Ω/□ or less, and the film thickness thereof is usually from 10 nm to 1 μm, preferably from 50 to 200 nm.

(Insulating layer)

In the organic EL device, pixel defects based on leakage or a short circuit are easily generated since an electric field is applied to the ultrathin film. In order to prevent this, it is preferred to insert an insulative thin layer between the pair of electrodes.

Examples of the material used in the insulating layer include aluminum oxide, lithium fluoride, lithium oxide, cesium fluoride, cesium oxide, magnesium oxide, magnesium fluoride, calcium oxide, calcium fluoride, cesium carbonate, aluminum nitride, titanium oxide, silicon oxide, germanium oxide, silicon nitride, boron nitride, molybdenum oxide, ruthenium oxide, and vanadium oxide.

A mixture or laminate thereof may be used.

(Example of Fabricating Organic EL Device)

Using the above-mentioned materials, an organic EL device can be fabricated by forming an anode, a hole-injecting layer, a hole-transporting layer, an emitting layer, an electron-injecting layer or the like, followed by formation of a cathode. The organic EL device can be fabricated in the order reverse to the above, i.e., the order from a cathode to an anode.

An example of the fabrication of the organic EL device will be described below which has a structure wherein the following are successively formed on a transparent substrate:anode/hole-injecting layer/hole-transporting layer/emitting layer/electron-transporting layer/cathode.

First, a thin film made of an anode material is formed into a thickness of 1 μm or less, preferably 10 to 200 nm on an appropriate transparent substrate by vapor deposition, sputtering or some other method, thereby forming an anode.

Next, a hole-injecting layer and a hole-transporting layer are formed on this anode. As described above, these layers can be formed by vacuum deposition, spin coating, casting, LB technique, or some other method. Vapor vacuum deposition is preferred since a homogenous film is easily obtained and pinholes are not easily generated.

In the case where the hole-injecting layer and the hole-transporting layer are formed by vapor vacuum deposition, conditions for the deposition vary depending upon the compound used, the desired crystal structure or recombining structure of the hole-injecting layer and the hole-transporting layer, and others. In general, the conditions are preferably selected from the following: deposition source temperature of 50 to 450° C., vacuum degree of $10^{-7}$ to $10^{-3}$ torr, vapor deposition rate of 0.01 to 50 nm/second, substrate temperature of −50 to 300° C., and film thickness of 1 nm to 5 μm.

Next, an emitting layer is formed on the hole-transporting layer. The emitting layer can also be formed by making a desired organic luminescent material into a thin film by vacuum vapor deposition, sputtering, spin coating, casting or some other method. Vacuum vapor deposition is preferred since a homogenous film is easily obtained and pinholes are not easily generated. In the case where the emitting layer is formed by vapor vacuum deposition, conditions for the deposition, which vary depending on a compound used, can be generally selected from conditions similar to those for the hole-transporting layer.

Next, an electron-transporting layer is formed on this emitting layer. Like the hole-transporting layer and the emitting layer, the layer is preferably formed by vacuum vapor deposition because a homogenous film is required. Conditions for the deposition can be selected from conditions similar to those for the hole-transporting layer and the emitting layer.

Lastly, a cathode is stacked thereon to obtain an organic EL device.

The cathode is made of a metal, and vapor deposition or sputtering may be used. However, vapor vacuum deposition is preferred in order to protect underlying organic layers from being damaged when the cathode film is formed.

For the organic EL device fabrication that has been described above, it is preferred that the formation from the anode to the cathode is continuously carried out, using only one vacuuming operation.

The method for forming each of the layers in the organic EL device of the invention is not particularly limited. Specifically, the layers can be formed by a known method, such as vacuum deposition, molecular beam deposition (MBE method), or coating method such as dipping, spin coating, casting, bar coating and roll coating using a solution obtained by dissolving materials in a solvent.

The film thickness of each of the organic layers in the organic EL device of the invention is not particularly limited. In general, defects such as pinholes are easily generated when the film thickness is too small. Conversely, when the film thickness is too large, a high applied voltage becomes necessary, leading to low efficiency. Usually, the film thickness is preferably in the range of several nanometers to one micrometer.

The organic EL device emits light when applying a voltage between electrodes. If a DC voltage is applied to the organic EL device, emission can be observed when the polarities of the anode and the cathode are positive and negative, respectively, and a DC voltage of 5 to 40 V is applied. When a voltage with an opposite polarity is applied, no electric current flows and hence, emission does not occur. If an AC voltage is applied, uniform emission can be observed only when the cathode and the anode have a positive polarity and a negative polarity, respectively. The waveform of the AC applied may be arbitrary.

EXAMPLES

The material for an organic EL device and the organic EL device of the invention will be described in more detail with reference to Examples, which should not be construed as limiting the scope of the invention.

The structures of the compounds used in the examples and comparative examples are shown below.

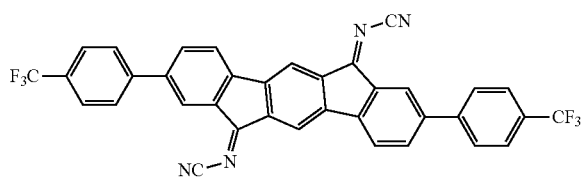

(A-1)

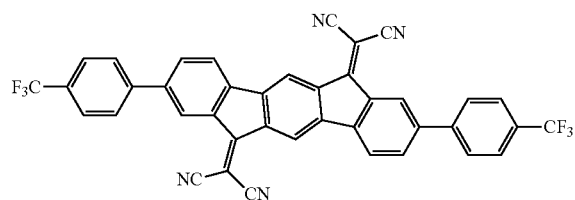
(A-2)
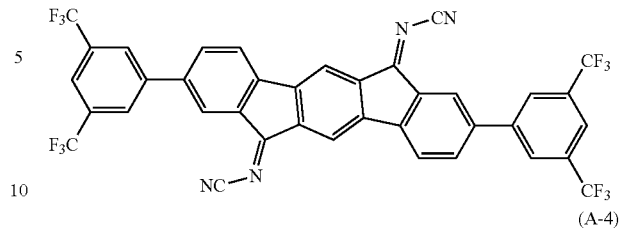
(A-3)
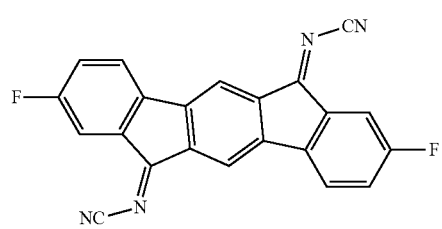
(A-15)
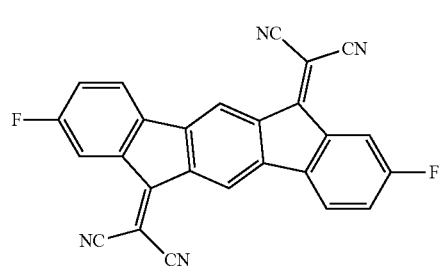
(A-16)
(A-4)
(A-38)
Example 1
[Synthesis of a Compound Shown by the Formula (A-1)]
The compound (A-1) was synthesized by the following synthesis scheme.
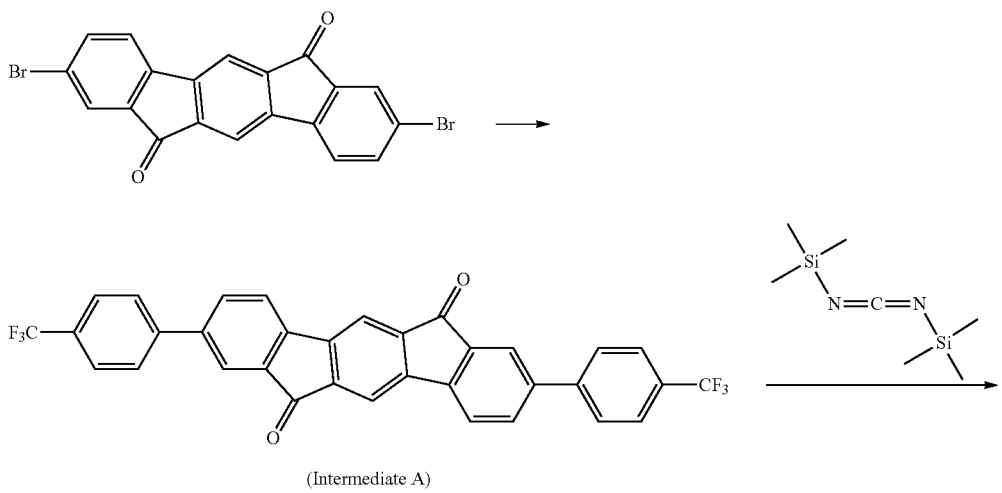
(Intermediate A)
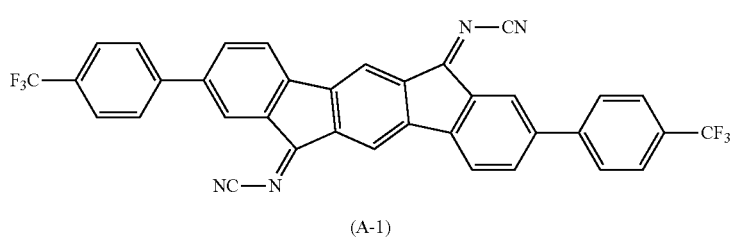
(A-1)

(1) Synthesis of Intermediate A 2.2 g of 3,9-dibromo-indenofluorenedione prepared according to a synthesis method described in a document (Organic Letters, vol. 7, issue 19, page 4229) was mixed with 2.1 g of 4-(trifluoromethyl)phenylboronic acid, 0.14 g of tris(dibenzylideneacetone)dipalladium (0), 0.091 g of tris-t-butylphosphine, 1.9 g of potassium fluoride and 40 ml of toluene under argon stream. The mixture was stirred with reflux for 8 hours. After cooling, the reaction liquid was filtered and a reddish purple solid was washed with water and methanol. As a result of mass spectroscopy of the resulting solid, a peak was observed at M/Z=570.

(2) Synthesis of Compound (A-1)

2.0 g of the intermediate A which had been synthesized before was dissolved in 100 ml of methylene chloride with stirring. After making the atmosphere of the inside of the flask argon, the temperature of the solution was cooled to −10° C. or less with a salt-ice bath. 2.7 g of titanium tetrachloride was added to the solution. Thereafter, a mixture of 8.2 g of bis(trimethylsilyl)carbodiimide and 40 ml of methylene chloride was added dropwise. After the dropwise addition, cooling was continued for 1 hour. Then, the mixture was stirred at room temperature for 4 hours, and stirred with reflux for a further 2 hours. A precipitated reddish purple solid was filtered and washed with methanol.

After purification through sublimation, 1.4 g of the compound was obtained.

The IR of this compound was measured. The results showed that the absorption of a carbonyl group disappeared and the absorption of a cyano group was newly observed at 2183 $cm^{-1}$. As a result of mass spectroscopy, a peak was observed at M/Z=618.

The compound was dissolved in acetonitrile with a concentration of 0.01 mol/l, and the reduction potential thereof was measured by cyclic voltammetry by using tetrabutylammonium perchlorate (TBAP) as a supporting electrolyte, a glassy carbon electrode as an active electrode, a platinum electrode as a counter electrode and a silver-silver chloride electrode as a reference electrode. The reduction potential of the compound (A-1) at a sweep rate of 0.1 V/s was −0.3 V.

As a reference material, ferrocene (hereinafter referred to as "Fc") was measured similarly. The first oxidation potential thereof was 0.5V. Taking this oxidation potential of ferrocene as a reference, the reduction potential of the compound (A-1) was −0.8 V(vs $Fc^+/Fc$).

Example 2

[Synthesis of a Compound Shown by the Formula (A-2)]

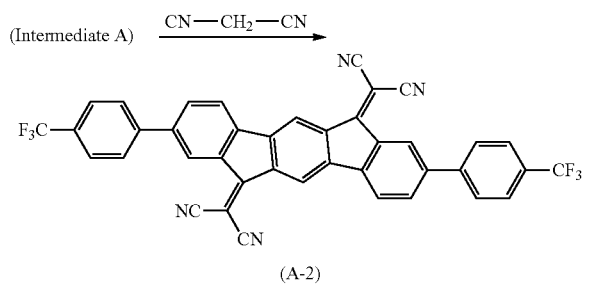

(A-2)

1.5 g of the intermediate A which had been synthesized before, 0.35 g of malononitrile and 80 ml of pyridine were added, and the resultant was heated with stirring at 90° C. for 8 hours. After cooling, the solid matter was filtered, washed with water and methanol, and dried under reduced pressure. Thereafter, purification through sublimation was performed to obtain 1.2 g of a purple crystal.

The IR of this compound was measured. The results showed that the absorption of a carbonyl group disappeared and the absorption of a cyano group was newly observed at 2222 $cm^{-1}$. As a result of mass spectroscopy, a peak was observed at M/Z=666.

In the same manner as in Example 1, the reduction potential of this compound was measured by cyclic voltammetry. When the first oxidation potential of ferrocene (hereinafter referred to as the "Fc") was taken as a reference potential, the reduction potential of the compound (A-2) was −0.75 V(vs $Fc^+/Fc$).

Example 3

[Synthesis of a Compound Shown by the Formula (A-15)]

The compound (A-15) was synthesized from the compound shown by the following formula B.

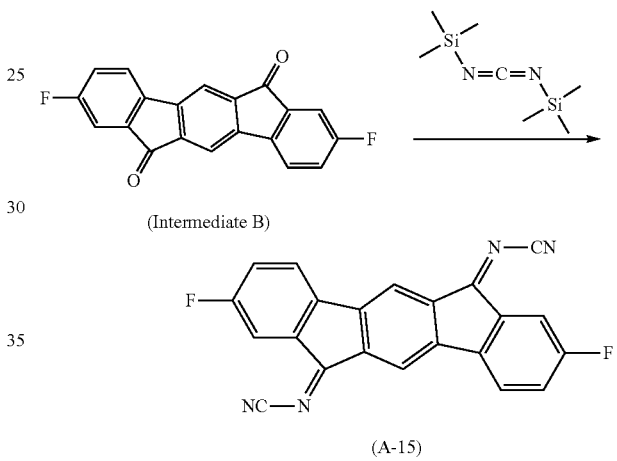

(Intermediate B)

(A-15)

In the synthesis of the compound (A-1) in Example 1, the same procedure was performed except that the intermediate A was changed to 1.1 g of the compound B, whereby 0.8 g of an orange solid as compound (A-15) was obtained.

The IR of this compound was measured. The results showed that the absorption of a carbonyl group disappeared and the absorption of a cyano group was newly observed at 2181 $cm^{-1}$. As a result of mass spectroscopy, a peak was observed at M/Z=366.

The reduction potential of this compound was measured in the same manner as in Example 1 and found to be −0.7V (vs $Fc^+/Fc$).

Example 4

[Synthesis of a Compound Shown by the Formula (A-16)]

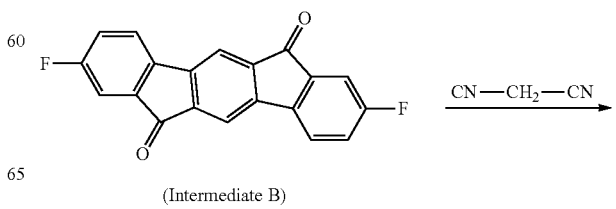

(Intermediate B)

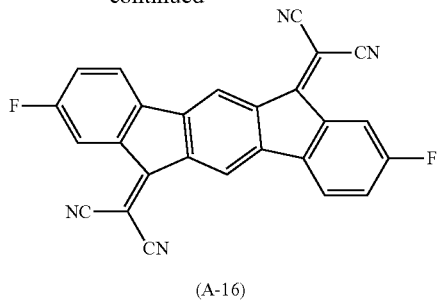

(A-16)

In the synthesis of the compound (A-2) in Example 2, the same procedure was performed except that the intermediate A was changed to 0.8 g of the compound B, whereby 0.6 g of an orange solid as the compound (A-16) was obtained.

The IR of this compound was measured. The results showed that the absorption of a carbonyl group disappeared and the absorption of a cyano group was newly observed at 2223 cm$^{-1}$. As a result of mass spectroscopy, a peak was observed at M/Z=414.

The reduction potential of this compound was measured in the same manner as in Example 1 and found to be −0.7V (vs Fc$^+$/Fc).

Example 5

[Synthesis of a Compound Shown by the Formula (A-3)]

(1) Synthesis of Intermediate C 2.4 g of 3,9-dibromo-indenofluorenedione was mixed with 3.4 g of 3,5-bis(trifluoromethyl)phenylboronic acid, 0.23 g of tetraxis(triphenylenephosphine)palladium (0), 20 ml of 2M sodium carbonate and 130 ml of toluene under argon stream. The mixture was stirred with reflux for 12 hours. After cooling, the reaction liquid was filtered, washed with water and methanol, whereby 3.5 g of a reddish purple solid as an intermediate A was obtained.

As a result of mass spectroscopy of the resulting solid, a peak was observed at M/Z=706.

(2) Synthesis of Compound (A-3)

In the synthesis of the compound (A-1) in Example 1, the same procedure was performed except that the intermediate A was changed to 2.4 g of the intermediate C, whereby 1.5 g of compound (A-3) was obtained.

The IR of this compound was measured. The results showed that the absorption of a carbonyl group disappeared and the absorption of a cyano group was newly observed at 2182 cm$^{-1}$. As a result of mass spectroscopy, a peak was observed at M/Z=754.

The reduction potential of this compound was measured in the same manner as in Example 1 and found to be −0.65V (vs Fc$^+$/Fc).

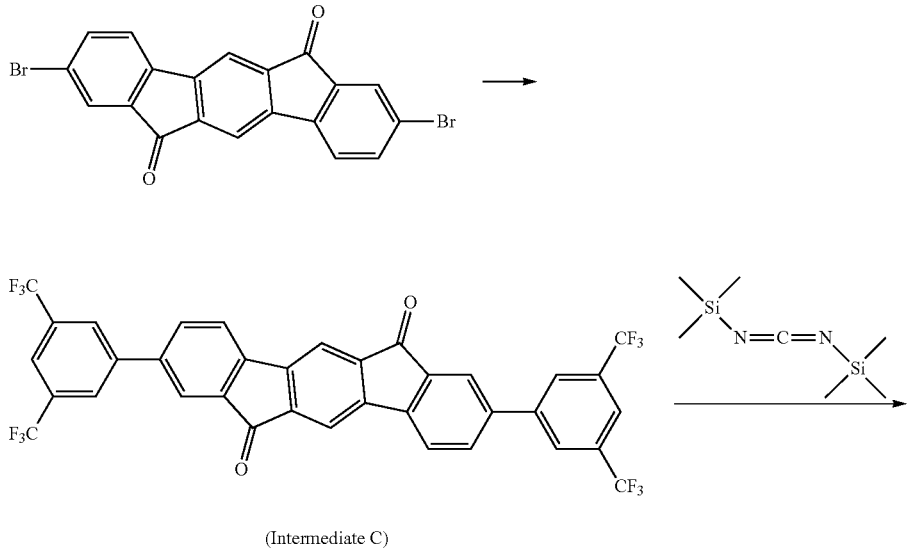

(Intermediate C)

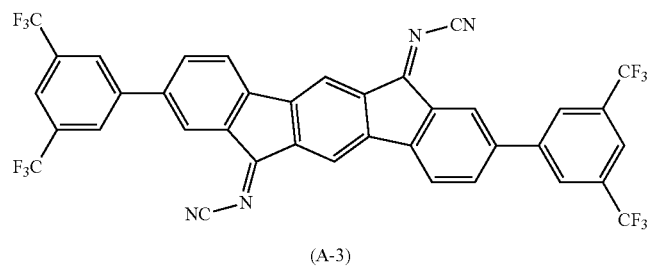

(A-3)

Example 6

[Synthesis of a Compound Shown by the Formula (A-4)]

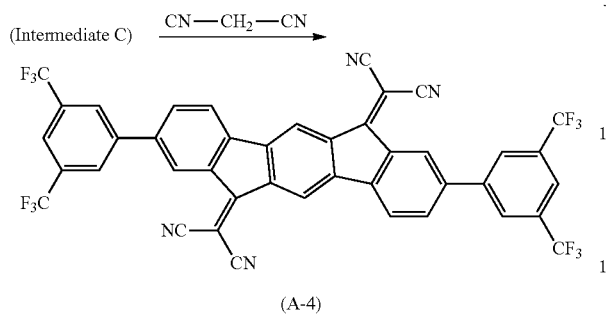

(A-4)

In the synthesis of the compound (A-2) in Example 2, the same procedure was performed except that the intermediate A was changed to 1.8 g of the intermediate C, whereby 1.2 g of an orange solid as compound (A-4) was obtained.

The IR of this compound was measured. The results showed that the absorption of a carbonyl group disappeared and the absorption of a cyano group was newly observed at 2223 cm$^{-1}$. As a result of mass spectroscopy, a peak was observed at M/Z=802.

The reduction potential of this compound was measured in the same manner as in Example 1 and found to be −0.6V (vs Fc$^+$/Fc).

Example 7

[Synthesis of a Compound Shown by the Formula (A-38)]

(1) Synthesis of Intermediate D 3.0 g of 3,9-dibromo-indenofluorenedione was mixed with 3.3 g of 4-fluoro-3-(trifluoromethyl)phenylboronic acid, 0.29 g of tetraxis(triphenylenephosphine)palladium (0), 25 ml of 2M sodium carbonate and 160 ml of toluene under argon stream. The mixture was stirred with reflux for 12 hours. After cooling, the reaction liquid was filtered, washed with water and methanol, whereby 3.7 g of a reddish purple solid as an intermediate D was obtained. As a result of mass spectroscopy of the resulting solid, a peak was observed at M/Z=606.

(2) Synthesis of Compound (A-38)

2.7 g of the intermediate D which had been synthesized before, 0.73 g of malononitrile and 67 ml of pyridine were added, and the resultant was heated with stirring at 80° C. for 7 hours. The solid matter was filtered, washed with water and methanol, and dried under reduced pressure. Thereafter, purification through sublimation was performed to obtain 1.7 g of a purple crystal as compound (A-38).

The IR of this compound was measured. The results showed that the absorption of a carbonyl group disappeared and the absorption of a cyano group was newly observed at 2185 cm$^{-1}$. As a result of mass spectroscopy, a peak was observed at M/Z=702.

The reduction potential of this compound was measured in the same manner as in Example 1 and found to be −0.75V (vs Fc$^+$/Fc).

[Organic EL Device]

Example 8

A glass substrate of 25 mm by 75 mm by 1.1 mm thick with an ITO transparent electrode (GEOMATEC CO., LTD.) was subjected to ultrasonic cleaning with isopropyl alcohol for 5 minutes, and cleaned with ultraviolet rays and ozone for 30 minutes.

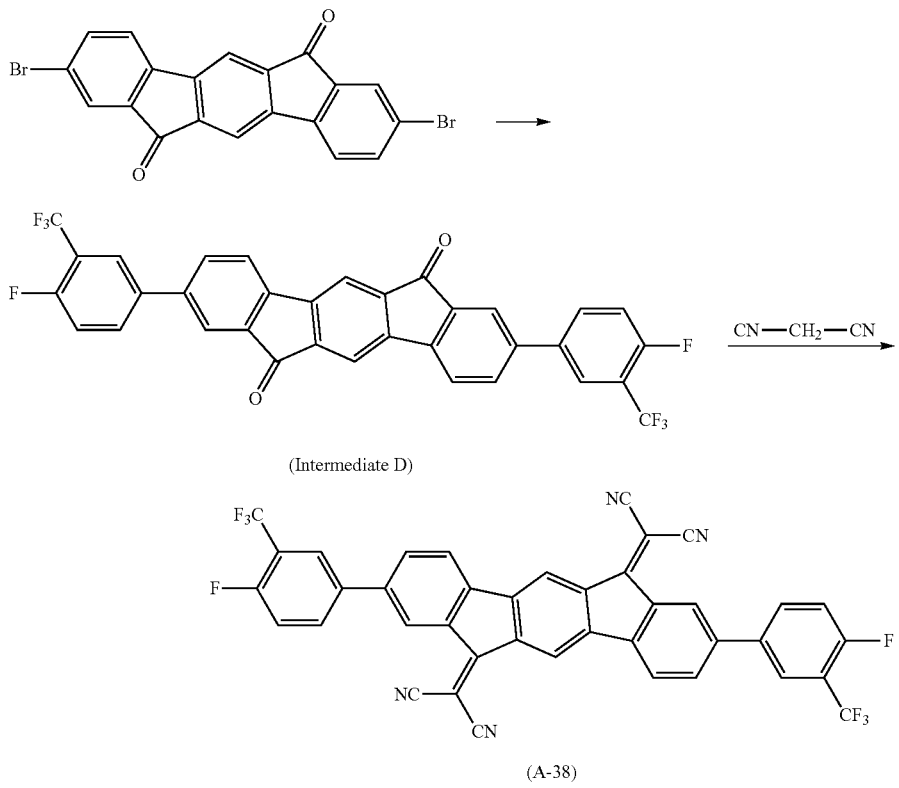

(A-38)

The cleaned glass substrate having the transparent electrode lines was then secured to a substrate holder of an apparatus for vacuum deposition. First, the compound shown by the formula (A-2) synthesized in Example 2 and a compound shown by the following formula (C-1) were formed into a 60 nm-thick film, at a molar ratio of 2:98, on the glass substrate on which the transparent electrode lines were formed so as to cover the transparent electrodes. The film of the compound mixture functioned as a hole-injecting layer.

Subsequently, a 20 nm-thick film of a compound shown by the following formula (HTM-1) was formed on the above-obtained film of the compound mixture. This film functioned as a hole-transporting layer.

Further, EM1 with a thickness of 40 nm was deposited thereon to form a film. Simultaneously, as the emitting molecule, the following compound D1 having a styryl group was deposited such that the weight ratio of EM1 and D1 became 40:2. This film functioned as an emitting layer.

A 10 nm-thick Alq film was formed on the above-obtained film. The film served as an electron-injecting layer. Then, Li as a reductive dopant (Li source: manufactured by SAES Getters Co., Ltd.) and Alq were co-deposited, whereby an Alq:Li film (film thickness: 10 nm) was formed as an electron-injecting layer (cathode). Metal aluminum was deposited on the Alq:Li film to form a metallic cathode, whereby an organic EL emitting device was fabricated.

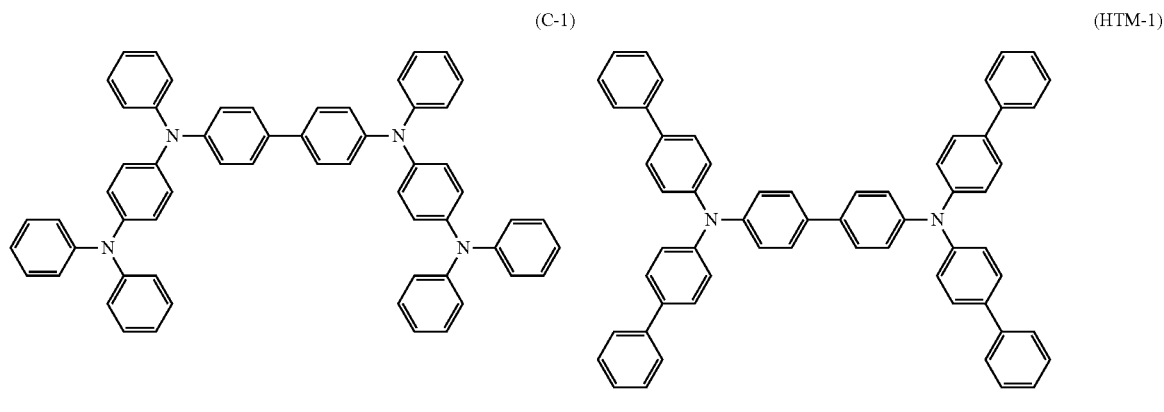
(C-1) (HTM-1)

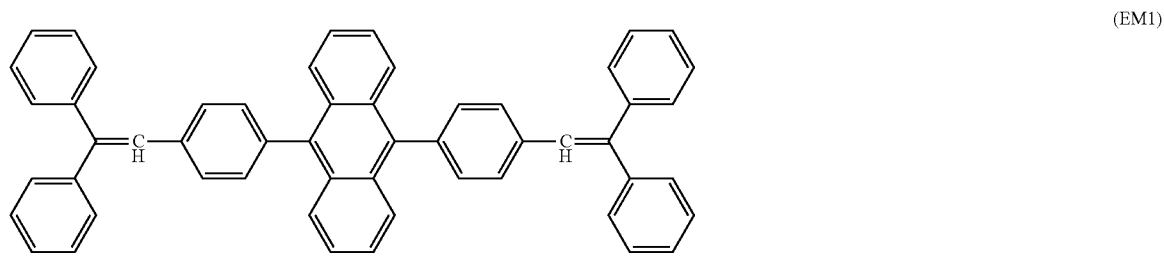
(EM1)

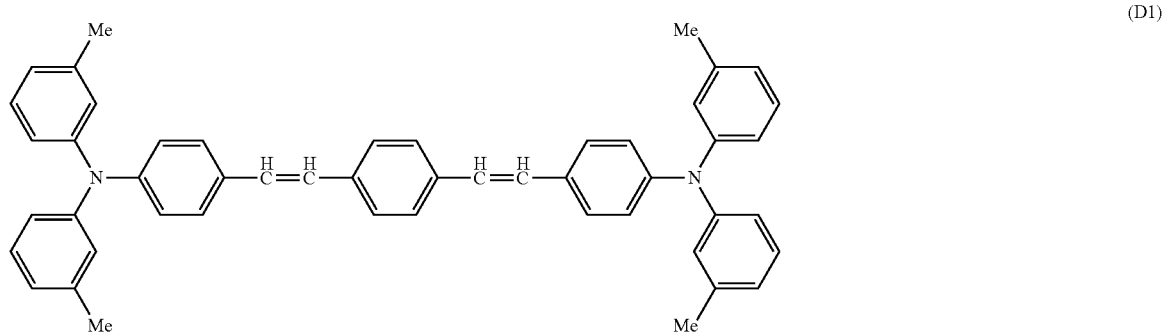
(D1)

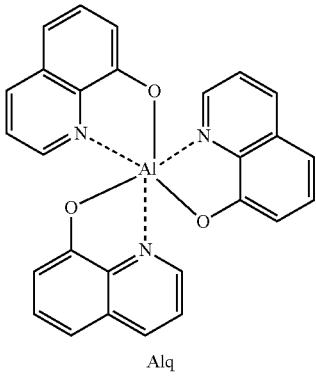

Alq

The organic EL device was evaluated by measuring a driving voltage at a current density of 10 mA/cm$^2$ and a half life of luminance at an initial luminance of 1,000 nits, at room temperature, and with a DC constant power supply. The results obtained are shown in Table 1.

Example 9

An organic EL device was fabricated and evaluated in the same manner as in Example 8, except that the compound (A-4) alone which had been synthesized in Example 6 was used in the hole-injecting layer, the thickness thereof was rendered 10 nm, and the thickness of the hole-translating layer (HTM-1) was changed to 70 nm. The results are shown in Table 1.

Example 10

An organic EL device was fabricated and evaluated in the same manner as in Example 9, except that the compound (A-38) alone which had been synthesized in Example 7 was used in the hole-injecting layer. The results are shown in Table 1.

Example 11

An organic EL device was fabricated and evaluated in the same manner as in Example 9, except that the compound (A-3) alone which had been synthesized in Example 5 was used in the hole-injecting layer. The results are shown in Table 1.

Example 12

An organic EL device was fabricated and evaluated in the same manner as in Example 9, except that that the compound (A-1) alone which had been synthesized in Example 1 was used in the hole-injecting layer. The results are shown in Table 1.

Example 13

An organic EL device was fabricated and evaluated in the same manner as in Example 9, except that the compound (A-2) alone which had been synthesized in Example 2 was used in the hole-injecting layer. The results are shown in Table 1.

Comparative Example 1

An organic EL device was fabricated and evaluated in the same manner as in Example 8, except that the compound shown by the formula (C-1) alone was used in the hole-injecting layer.

The results are shown in Table 1.

In the case of the organic EL device of Comparative Example 1, voltage was increased by 1V or more after 5,000 hour-driving. In contrast, in organic EL devices of Examples 8 to 13, voltage was increased by 0.5V or less, which showed that a voltage increase was suppressed in Examples 8 to 13.

Comparative Example 2

An organic EL device was fabricated and evaluated in the same manner as in Example 9, except that the compound B (2,7-difluoroindenofluorenedione) alone was used for forming a hole-injecting layer. The results showed that the resulting organic EL device suffered a large amount of leak current, and uniform emission could not be obtained. The reason therefor is thought to be the crystallization of the compound B, the shortage of an acceptor due to the quinone structure, or the like.

TABLE 1

| | Materials constituting the hole-injecting layer | Driving voltage (V) | Half life (hr) |
|---|---|---|---|
| Example 8 | Compound (A-2) Compound (C-1) | 6.2 | 6,600 |
| Example 9 | Compound (A-4) | 5.8 | 7,600 |
| Example 10 | Compound (A-38) | 5.8 | 7,400 |
| Example 11 | Compound (A-3) | 6.2 | 7,500 |
| Example 12 | Compound (A-1) | 5.9 | 7,400 |
| Example 13 | Compound (A-2) | 6.1 | 6,800 |
| Com. Ex. 1 | Compound (C-1) | 6.6 | 5,000 |

Industrial Applicability

The material for an organic EL device of the invention is suitable as a constitution material of an organic EL device, in particular, a hole-transporting layer or a hole-injecting layer. The material for an organic EL device of the invention can also be used as a charge-transporting material of an electrophotographic photoreceptor.

The organic EL device of the invention can be suitably used as a light source such as a planar emitting body and backlight of a display, a display part of a portable phone, PDA, a car navigator, or an instruction panel of an automobile, an illuminator, and the like.

The contents of all the documents in this specification are incorporated herein by reference.

The invention claimed is:

1. A material for an organic electroluminescence device comprising at least one indenofluorenedione derivative represented by any of the following formulae (IIa), (IIb), (IIc) and (III):

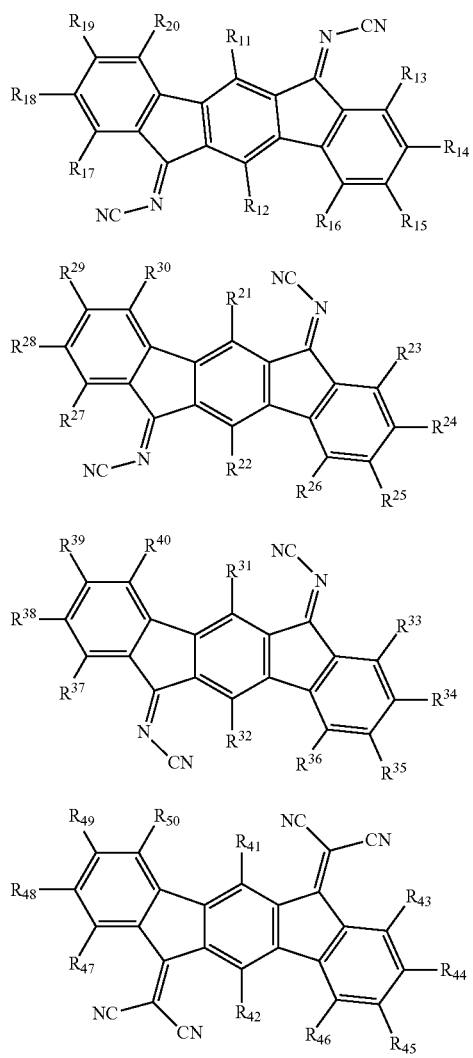

wherein $R^{11}$ to $R^{50}$, which may be the same or different, are a hydrogen atom, an alkyl group that may be substituted by a substituent, an aryl group that may be substituted by a substituent, a fluoroalkyl group that may be substituted by a substituent, or a heterocycle that may be substituted by a substituent, provided that a case where all of $R^{11}$ to $R^{50}$ are a hydrogen atom is excluded; and $R^{11}$ to $R^{50}$ may be bonded to each other to form a ring.

2. The material for an organic electroluminescence device according to claim 1, wherein the substituent is present and is at least one substituent selected from the group consisting of a halogen atom, a cyano group, an alkyl group, an aryl group, a fluoroalkyl group, and a heterocycle.

3. A material for an organic electroluminescence device comprising at least one indenofluorenedione derivative represented by any of the following formulae (IIa), (IIb), (IIc) and (III):

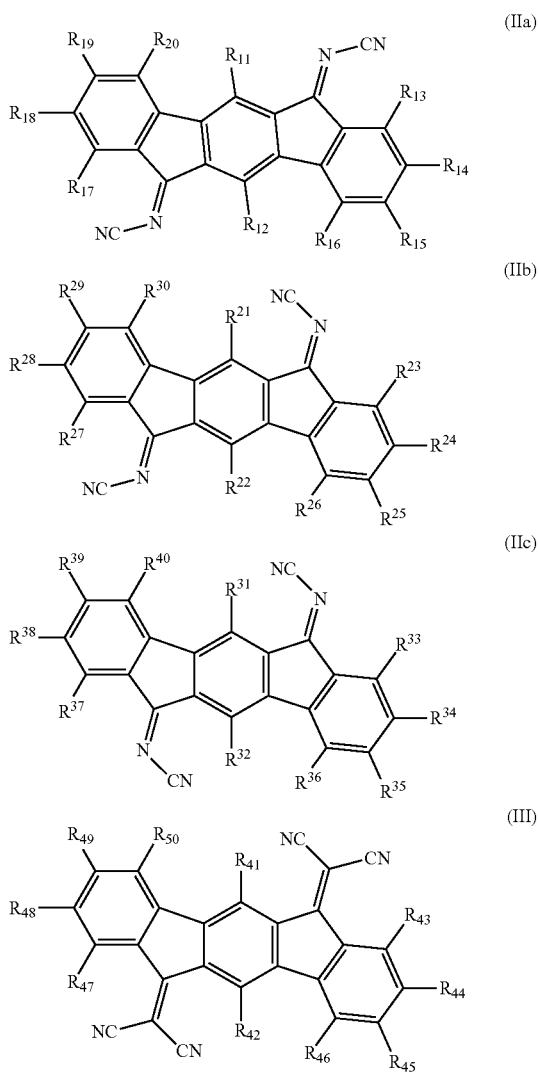

wherein $R^{11}$ to $R^{50}$, which may be the same or different, are a hydrogen atom, an aryl group that may be substituted by a substituent, an alkoxy group that may be substituted by a substituent, an aryloxy group that may be substituted by a substituent, or a heterocycle that may be substituted by a substituent, provided that a case where all of $R^{11}$ to $R^{50}$ are a hydrogen atom is excluded; and $R^{11}$ to $R^{50}$ may be bonded to each other to form a ring.

4. The material for an organic electroluminescence device according to claim 3, wherein the substituent is present and is at least one substituent selected from the group consisting of a fluorine atom, a cyano group, an aryl group, and a fluoroalkyl group.

5. An indenofluorenedione derivative represented by any of the following formulae (IIa), (IIb), (IIc) and (III):

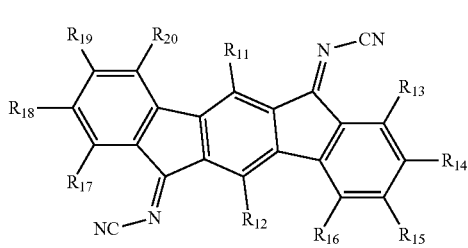
(IIa)

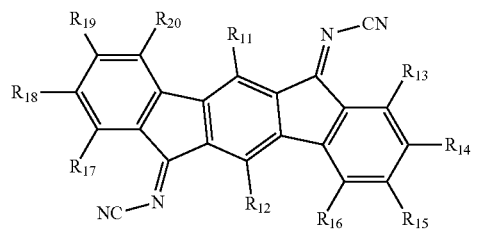
(IIa)

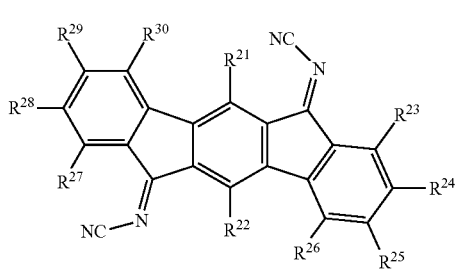
(IIb)

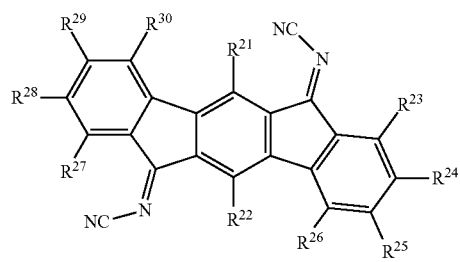
(IIb)

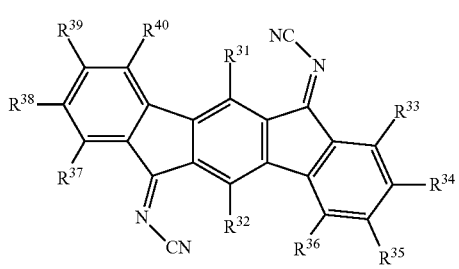
(IIc)

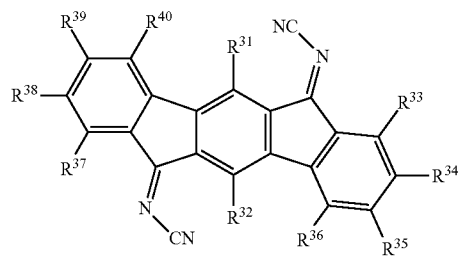
(IIc)

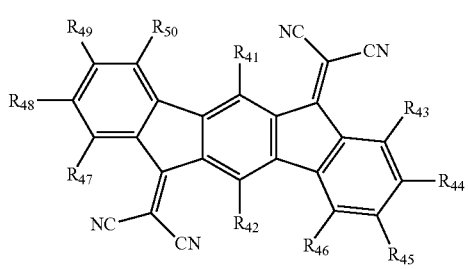
(III)

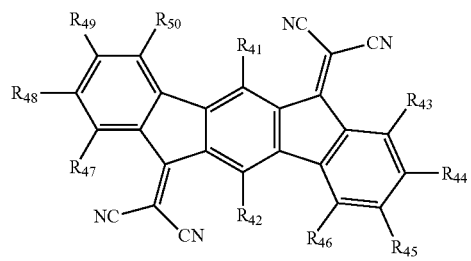
(III)

wherein $R^{11}$ to $R^{50}$, which may be the same or different, are a hydrogen atom, an alkyl group that may be substituted by a substituent, an aryl group that may be substituted by a substituent, a fluoroalkyl group that may be substituted by a substituent, or a heterocycle that may be substituted by a substituent, provided that a case where all of $R^{11}$ to $R^{50}$ are a hydrogen atom is excluded; and $R^{11}$ to $R^{50}$ may be bonded to each other to form a ring.

6. The indenofluorenedione derivative according to claim 5, wherein the substituent is present and is at least one substituent selected from the group consisting of a halogen atom, a cyano group, an alkyl group, an aryl group, a fluoroalkyl group, and a heterocycle.

7. An indenofluorenedione derivative represented by any of the following formulae (IIa), (IIb), (IIc) and (III):

wherein $R^{11}$ to $R^{50}$, which may he the same or different, are a hydrogen atom, an aryl group that may be substituted by a substituent, an alkoxy group that may be substituted by a substituent, aryloxy group that may be substituted by a substituent, or a heterocycle that may be substituted by a substituent, provided that a case where all of $R^{11}$ to $R^{50}$ are a hydrogen atom is excluded; and $R^{11}$ to $R^{50}$ may be bonded to each other to form a ring.

8. The indenofluorenedione derivative according to claim 7, wherein the substituent is present and is at least one substituent selected from the group consisting of a fluorine atom, a cyano group, an aryl group, and a fluoroalkyl group.

9. A compound represented by any of the following formulae (A-1) to (A-89):

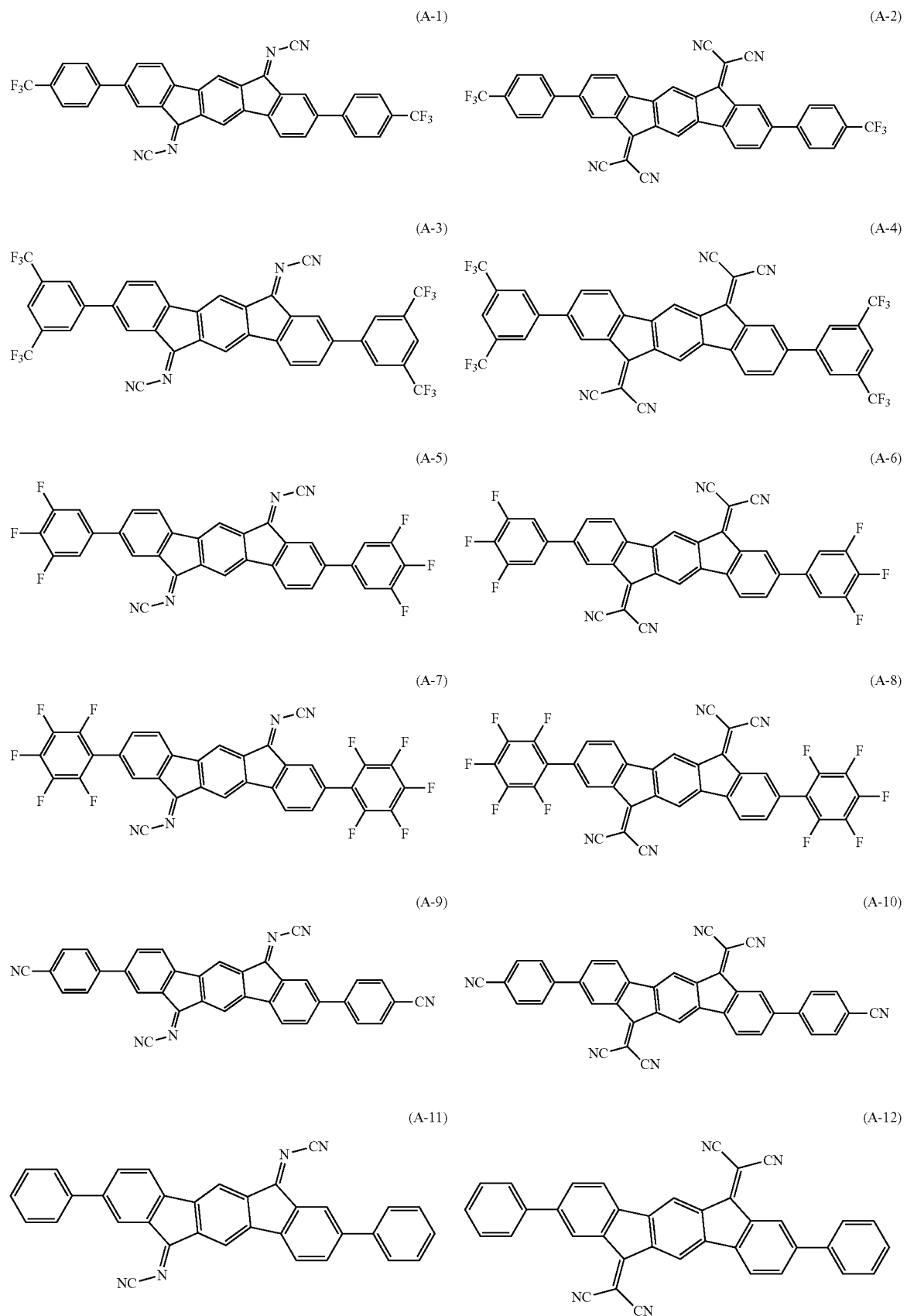

-continued
(A-13)
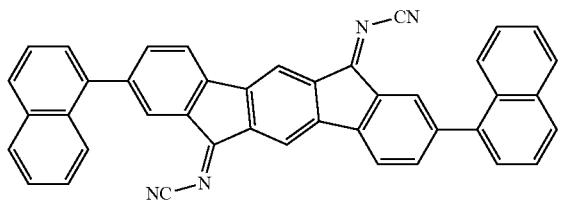
(A-14)
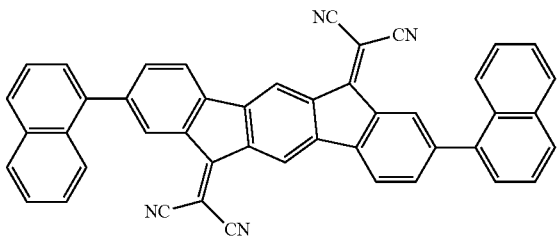
(A-15)
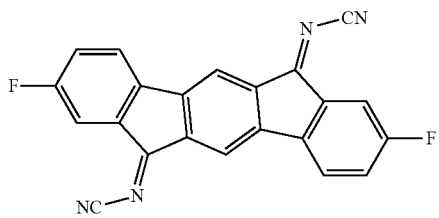
(A-16)
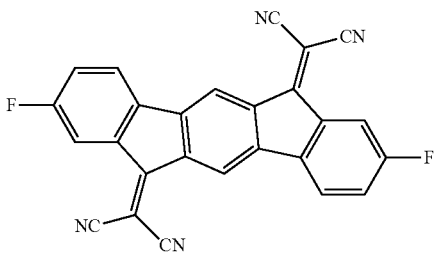
(A-17)
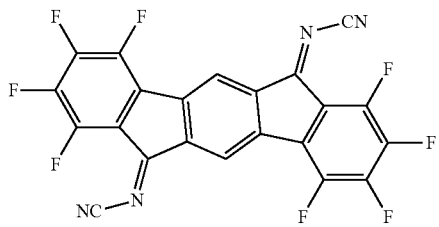
(A-18)
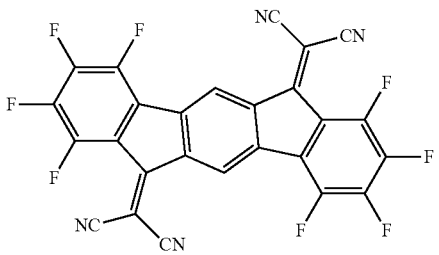
(A-19)
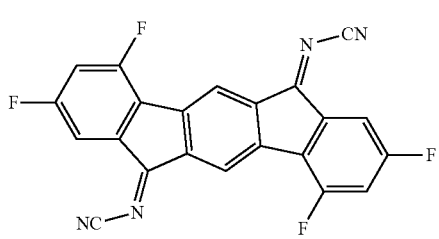
(A-20)
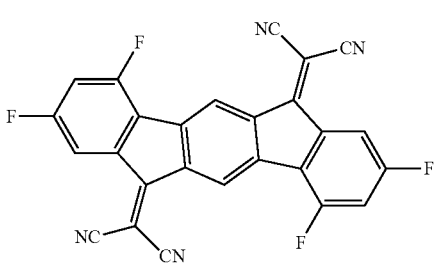
(A-21)
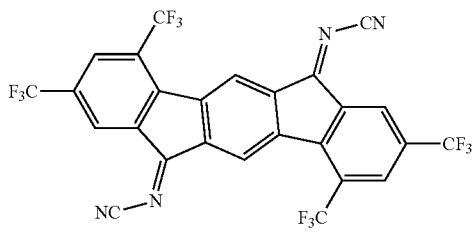
(A-22)
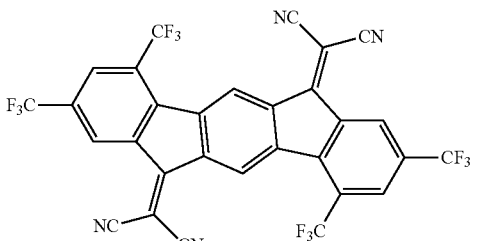
(A-23)
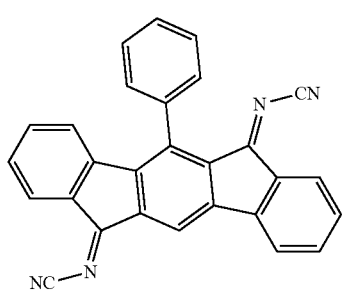
(A-24)
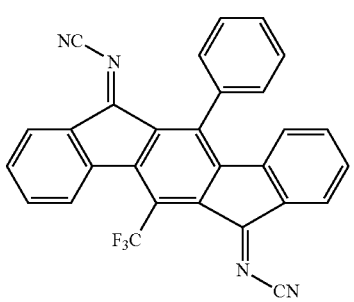

-continued
(A-25)
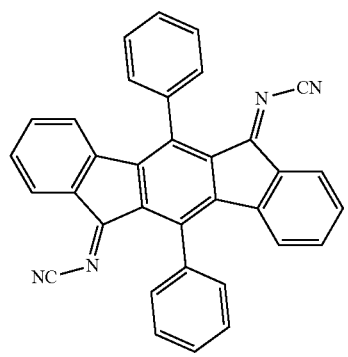
(A-26)
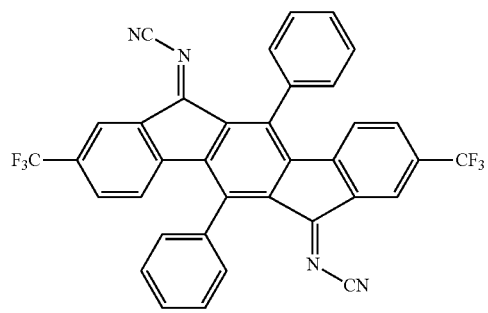
(A-27)
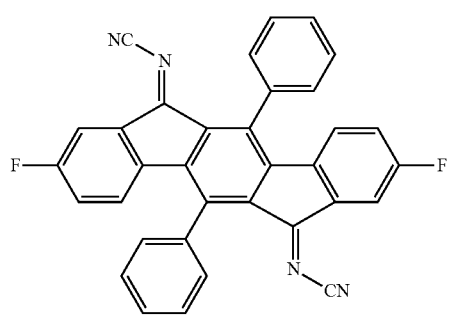
(A-28)
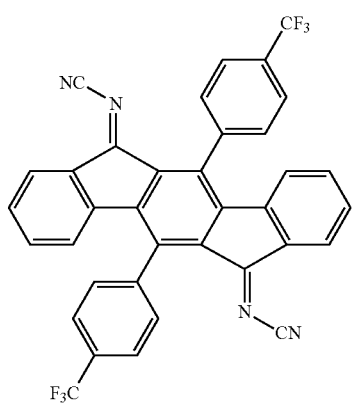
(A-29)
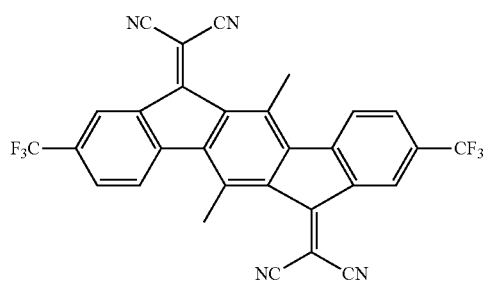
(A-30)
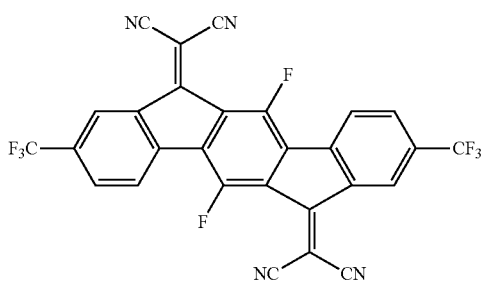
(A-31)
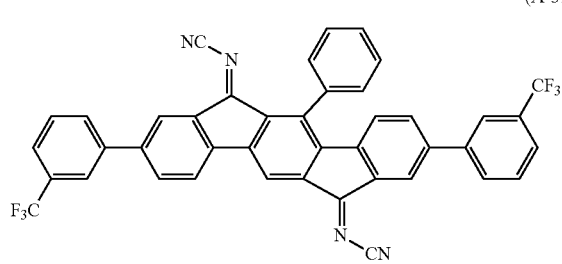
(A-32)
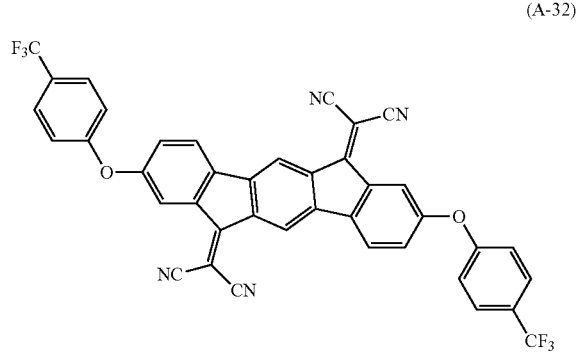

-continued
(A-33)
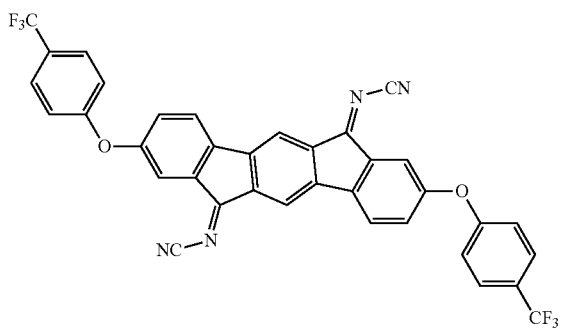
(A-34)
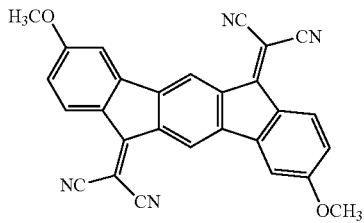
(A-35)
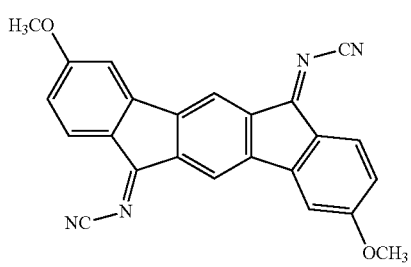
(A-36)
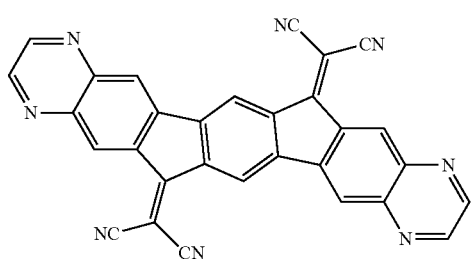
(A-37)
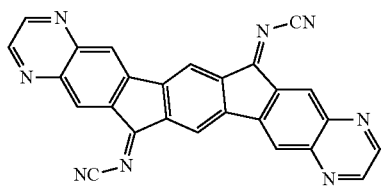
(A-38)
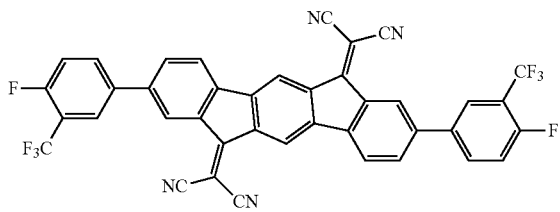
(A-39)
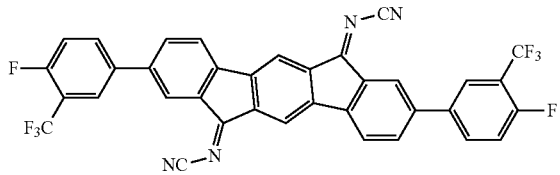
(A-40)
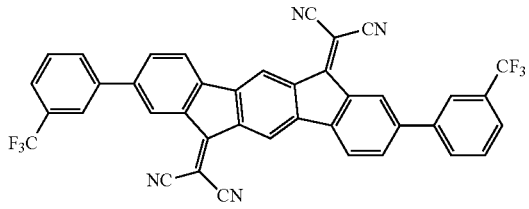
(A-41)
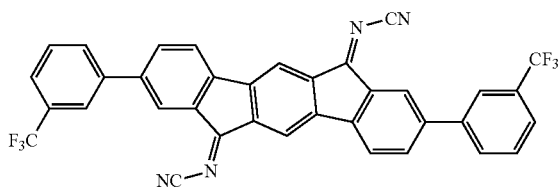
(A-42)
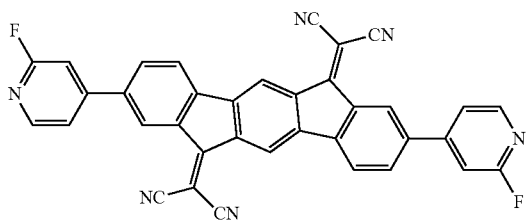
(A-43)
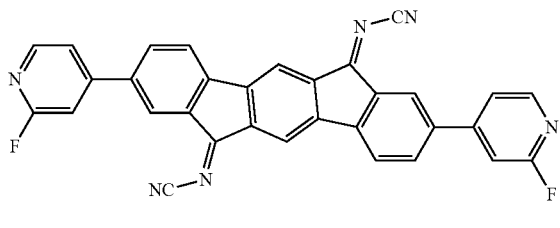
(A-44)
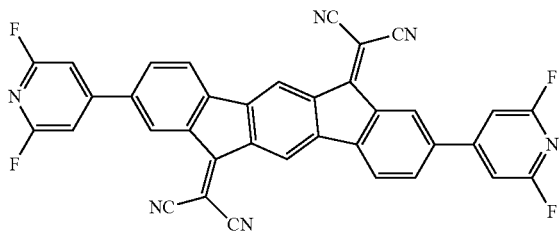

-continued
(A-45)
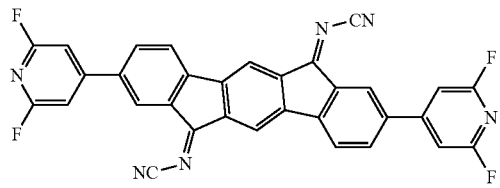
(A-46)
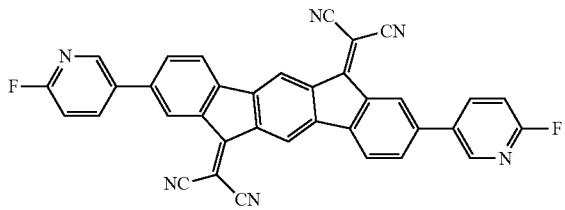
(A-47)
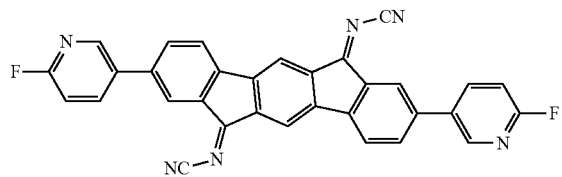
(A-48)
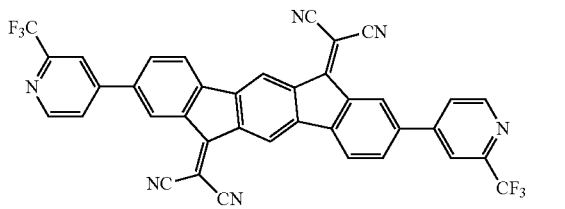
(A-49)
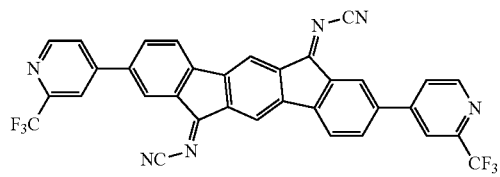
(A-50)
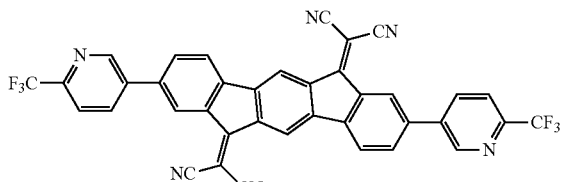
(A-51)
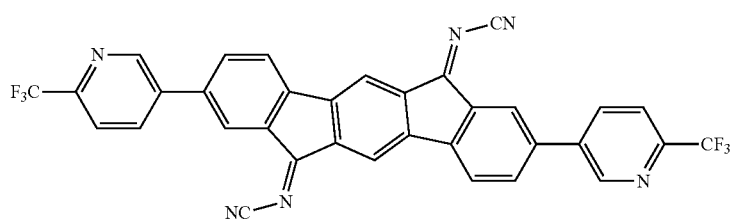
(A-52)
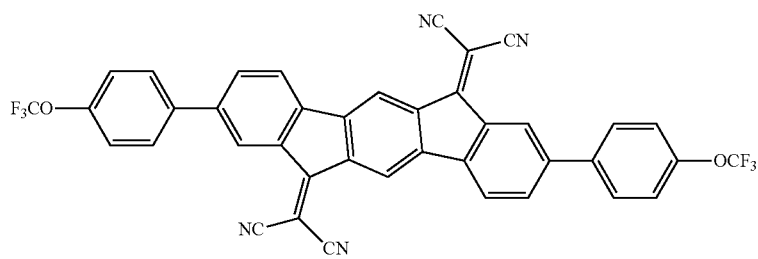
(A-53)
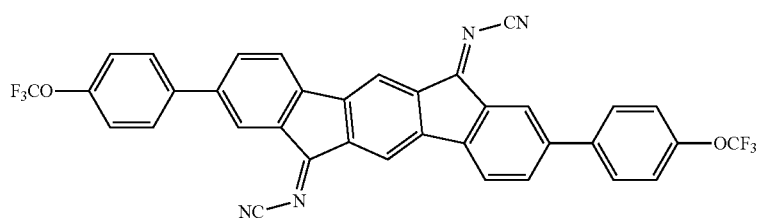
(A-54)
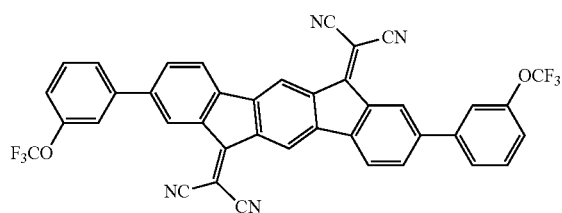
(A-55)
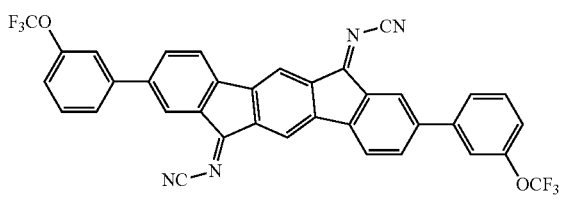

-continued
(A-56)
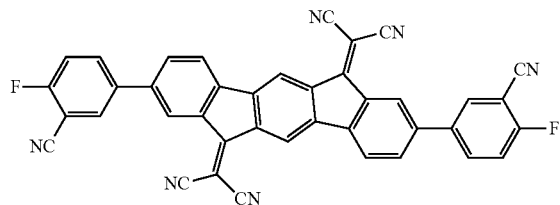
(A-57)
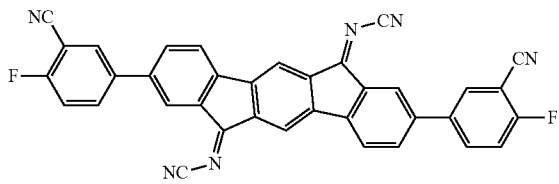
(A-58)
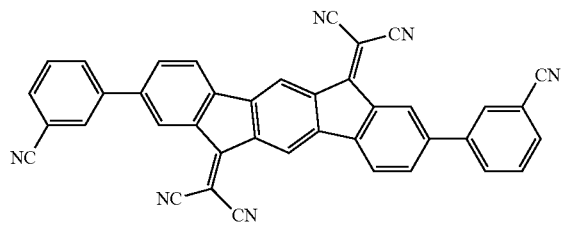
(A-59)
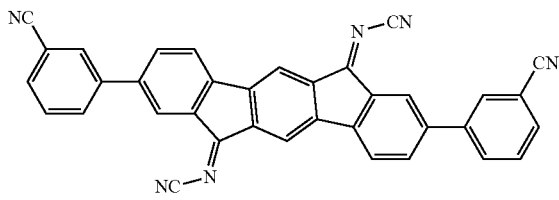
(A-60)
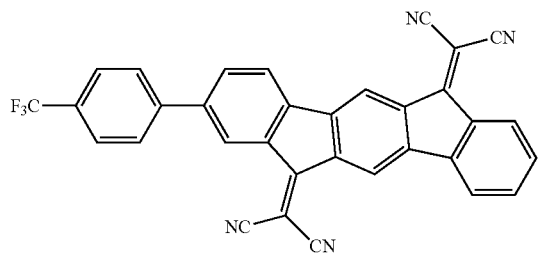
(A-61)
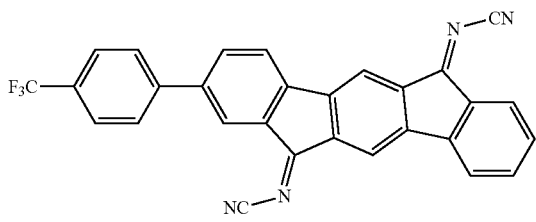
(A-62)
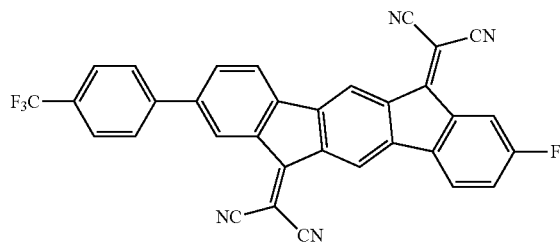
(A-63)
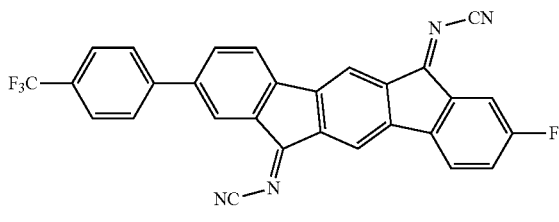
(A-64)
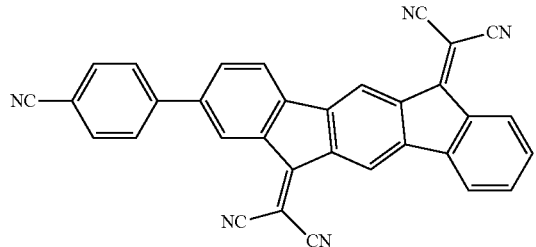
(A-65)
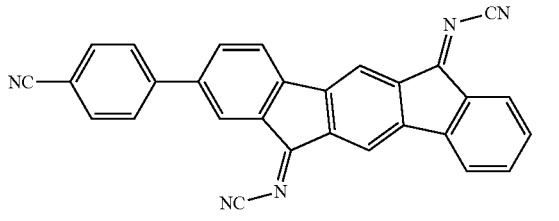
(A-66)
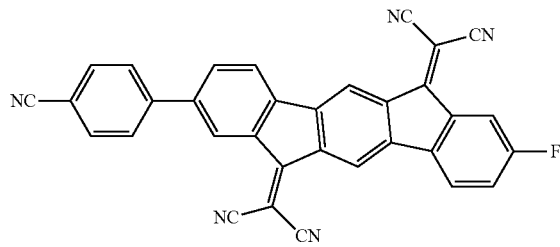

-continued
(A-68)
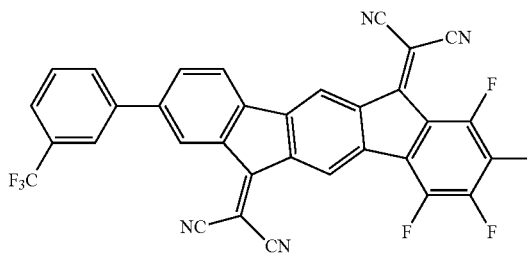
(A-69)
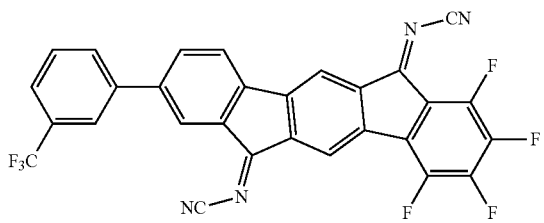
(A-70)
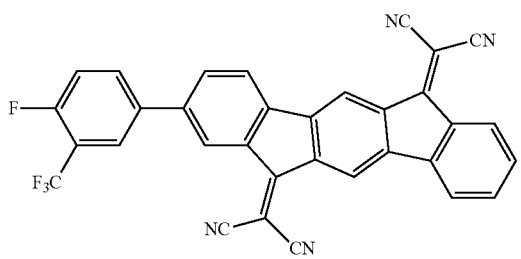
(A-71)
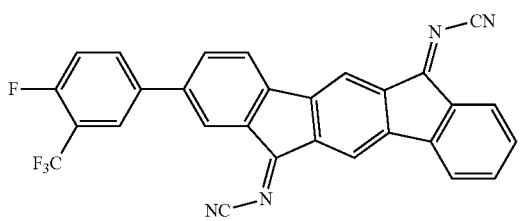
(A-72)
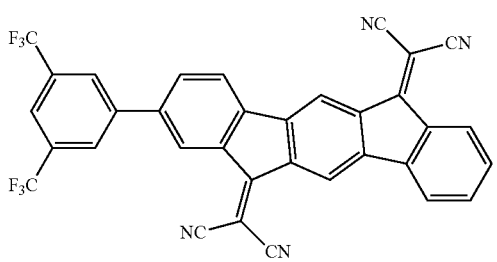
(A-73)
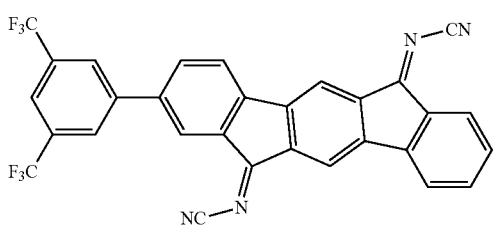
(A-74)
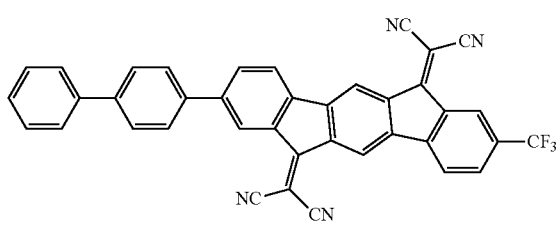
(A-75)
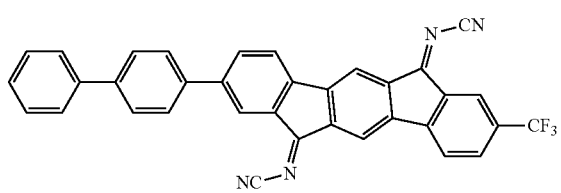
(A-76)
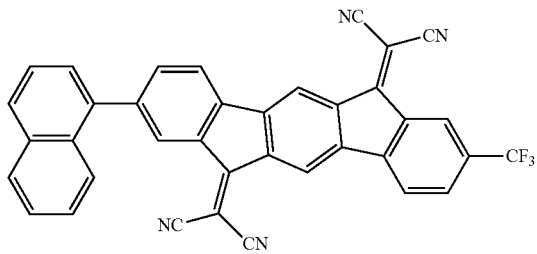
(A-77)
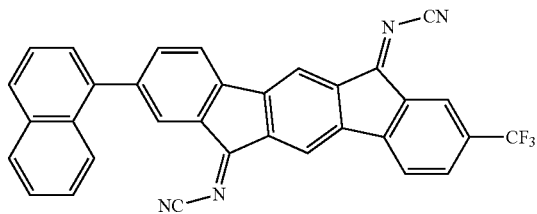
(A-78)
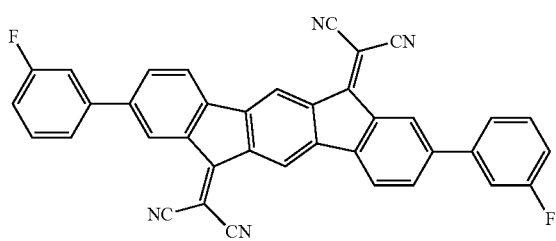
(A-79)
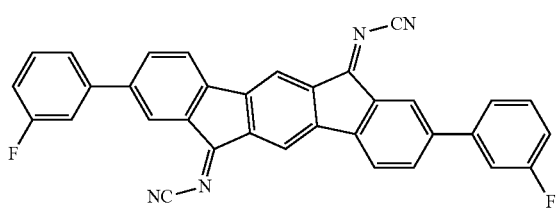

-continued
(A-80)
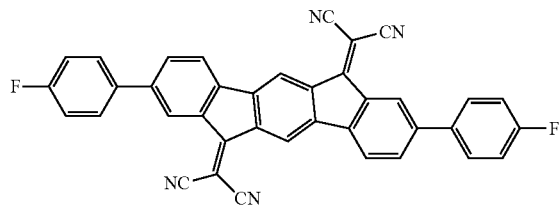
(A-81)
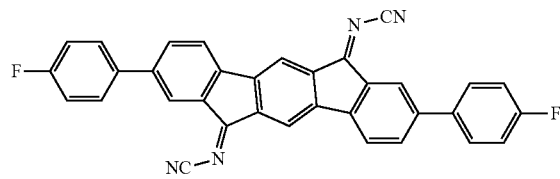
(A-82)
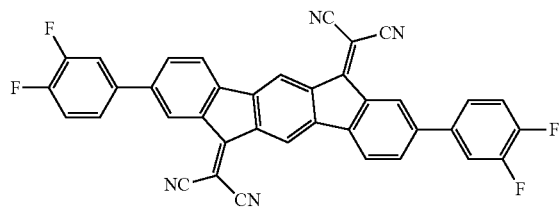
(A-83)
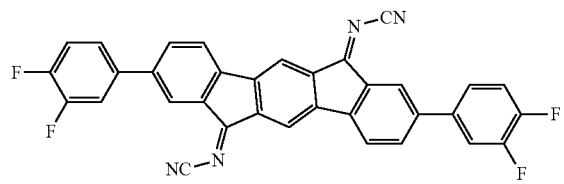
(A-84)
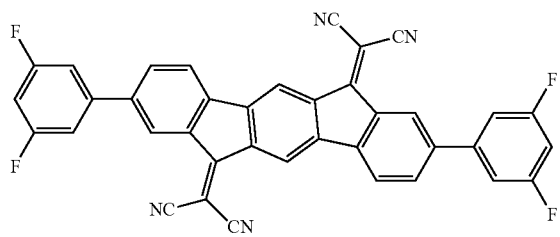
(A-85)
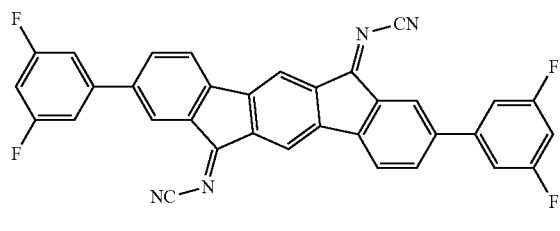
(A-86)
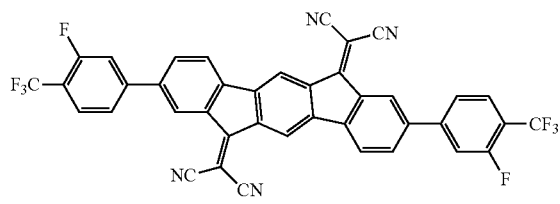
(A-87)
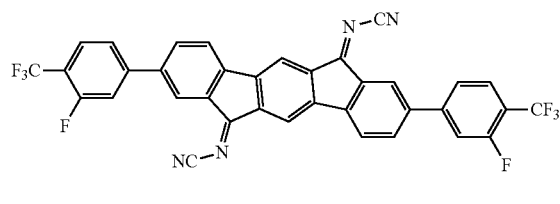
(A-88)
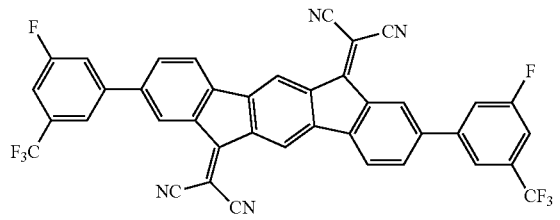
(A-89)
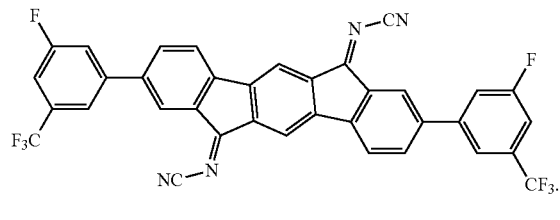
* * * * *